United States Patent
Shirude et al.

(10) Patent No.: US 9,163,020 B2
(45) Date of Patent: Oct. 20, 2015

(54) AZAINDOLE COMPOUNDS, SYNTHESIS THEREOF, AND METHODS OF USING THE SAME

(71) Applicants: Global Alliance for TB Drug Development, New York, NY (US); AstraZeneca AB, Sodertalje (SE)

(72) Inventors: Pravin S. Shirude, Bangalore (IN); Maruti N. Naik, Bangalore (IN); Vikas Narayan Shinde, Bangalore (IN); Shahul Hameed Peer Mohamed, Bangalore (IN); Monalisa Chatterji, Bangalore (IN); Radha K. Shindil, Bangalore (IN)

(73) Assignees: Global Alliance for TB Drug Development, New York, NY (US); Foundation for Neglected Disease Research, Bangalore (IN)

( * ) Notice: Subject to any disclaimer, the term of this patent is extended or adjusted under 35 U.S.C. 154(b) by 0 days.

(21) Appl. No.: 14/327,784

(22) Filed: Jul. 10, 2014

(65) Prior Publication Data

US 2015/0025087 A1    Jan. 22, 2015

(30) Foreign Application Priority Data

Jul. 17, 2013  (IN) .......................... 3196/CHE/2013

(51) Int. Cl.
*C07D 471/04* (2006.01)
*A61K 31/437* (2006.01)
*A61P 31/06* (2006.01)
*C07D 403/12* (2006.01)

(52) U.S. Cl.
CPC ............ *C07D 471/04* (2013.01); *A61K 31/437* (2013.01); *C07D 403/12* (2013.01)

(58) Field of Classification Search
USPC .......................................... 514/300; 546/113
See application file for complete search history.

(56) References Cited

FOREIGN PATENT DOCUMENTS

WO    2011/113606 A1    9/2011

OTHER PUBLICATIONS

Lechartier; Antimicrob. Agents Chemother., 2012, 56, 5790-5793.*
Nuermberger; American Journal of Respiratory and Critical Care Medicine, 2004, 169, 421-426.*
European Patent Office; International Search Report and Written Opinion; PCT Application No. PCT/US2014/046100; Oct. 13, 2014.
Zhang, Ying: The Magic Bullets and Tuberculosis Drug Targets; Annual Review of Pharmacology and Toxicology; vol. 45, pp. 529-564, 2005.
Ballell, Lluis et al: New Small-Molecule Synthetic Antimycobacterials; Antimicrobial Agents and Chemotherapy; vol. 49, No. 6, pp. 2153-2163, 2005.
Ananthan, Subramaniam et al: High-Throughput Screening for Inhibitors of *Mycobacterium tuberculosis* H37RV; Tuberculosis; vol. 89, pp. 334-353, 2009.
Nuermberger, Eric L.: Current Development and Future Prospects in Chemotherapy of Tuberculosis; Respirology; vol. 15, pp. 764-778, 2010.
Reynolds, Robert C.: High Throughput Screening of a Library Based on Kinase Inhibitor Scaffolds Against *Mycobacterium tuberculosis* H37RV; Tuberculosis; vol. 92, pp. 72-83, 2012.

(Continued)

*Primary Examiner* — John Mabry
*Assistant Examiner* — Daniel Carcanague
(74) *Attorney, Agent, or Firm* — Jackson Walker L.L.P.

(57) ABSTRACT

The invention provides compounds of formula (I) and methods of treating a *Mycobacterium* infection or tuberculosis, or inhibiting DprE1 with the same.

26 Claims, 26 Drawing Sheets

(56) References Cited

OTHER PUBLICATIONS

Ekins, Sean et al: Bayesian Models Leveraging Bioactivity and Cytotoxicity Information for Drug Discovery; Chemistry & Biology; Vol. 20, pp. 370-378, 2013.

Ballell, Lluis et al: Fueling Open-Source Drug Discovery: 177 Small-Molecule Leads Against Tuberculosis; ChemMedChem, vol. 8, pp. 313-321, 2013.

* cited by examiner

Scheme 1

Scheme 3

Scheme 4

Scheme 5

Scheme 6

Scheme 7

Scheme 8

Scheme 9

Scheme 10

Figure 25

Table 2

| Compounds | MIC (µM) | | | | | | | | | | | | | |
|---|---|---|---|---|---|---|---|---|---|---|---|---|---|---|
| | H37Rv ATCC 27294 | Msm ATCC | Msm mc2155 | Eco ARC 523 | Eco tolC | Hin ARC 446 | Hin ARC 158 | Pae ARC 545 | Pae ARC 546 | Kpn ARC 1865 | Sau ARC 517 | Spn ARC 548 | Spn ARC 546 | Cal ARC 527 |
| Compound 3 | 2 | 6.25 | 2 | >200 | >200 | >200 | >200 | >200 | >200 | >200 | >200 | >200 | >200 | >200 |
| Compound 4 | <0.39 | <0.39 | <0.39 | >200 | >200 | >200 | >200 | >200 | >200 | >200 | >200 | >200 | >300 | >200 |
| Compound 8 | <0.39 | <0.39 | <0.39 | >200 | >200 | >200 | >200 | >200 | >200 | >200 | >200 | >200 | >200 | >200 |
| Compound 17 | 2 | 3.125 | 2 | >200 | >200 | >200 | >200 | >200 | >200 | >200 | >200 | >200 | >200 | >200 |

Msm ATCC        Mycobacterium smegmatis 607
Msm mc²155      Mycobacterium smegmatis mc2155
Eco ARC523      Escherichia coli ARC523
Eco tolC        Escherichia coli tolC strain (tolC mutant)
Hin ARC 446     Haemophilus influenzae ARC446
Hin ARC 158     Haemophilus influenzae ARC158 (acrB mutant)
Pae ARC 545     Pseudomonas aeruginosa ARC545
Pae ARC 546     Pseudomonas aeruginosa ARC546 (MexABCDXY mutant)
Kpn ARC 1865    Klebsiella pneumoniae ARC1865
Sau ARC 517     Staphylococcus aureus ARC517
Spn ARC 548     Streptococcus pneumoniae ARC548
Spn ARC 546     Streptococcus pneumoniae ARC548
Cal ARC 527     Candida albicans ARC527

Figure 26

Table 3

| | M. tuberculosis Sensitive strains | | | | | | | | | | | | StrR | | | InhR | RifR |
|---|---|---|---|---|---|---|---|---|---|---|---|---|---|---|---|---|---|
| | | | | | | | | MIC (µM) | | | | | | | | | |
| Compound | H37Rv ATCC 27294 | Erdman | Beijing (E-47/94) | Harlingen | CDC1551 | TN14149 | SA161 | SA310 | DKU-76 | DKU-97A | DKU-211 | DKU-220 | ATCC 35811 | ATCC 35820 | 6570 | ATCC 35822 | Rif Res |
| Compound 3 | 3.125 | 3.125 | 1.56 | 1.56 | 1.56 | 1.56 | 3.125 | 1.56 | 3.125 | 3.125 | 3.125 | 1.56 | 1.56 | 3.125 | 3.125 | 3.125 | 3.125 |
| Compound 4 | 0.39 | 0.39 | 0.78 | 0.39 | 0.78 | 0.78 | 0.78 | 0.39 | 0.78 | 0.39 | 0.39 | 0.78 | 0.78 | 0.39 | 0.39 | 0.39 | 0.78 |
| Compound 8 | 0.78 | 0.39 | 0.39 | 0.78 | 0.39 | 1.56 | 0.78 | 0.39 | 0.78 | 0.78 | 0.39 | 0.78 | 0.78 | 0.39 | 0.39 | 0.39 | 0.39 |
| Compound 17 | 1.56 | 1.56 | 1.56 | 0.78 | 0.78 | 1.56 | 0.78 | 0.78 | 1.56 | 0.78 | 0.78 | 0.39 | 0.78 | 0.78 | 0.78 | 0.78 | 0.78 |
| Streptomycin | 0.34 | 0.34 | 0.17 | 0.17 | 0.34 | 0.34 | 0.34 | 0.34 | 0.17 | 0.17 | 0.17 | 0.68 | 0.34 | >5 | >5 | 0.17 | 0.17 |
| Isoniazid | 0.24 | 0.24 | 0.24 | 0.24 | 0.12 | 0.12 | 0.12 | 0.12 | 0.12 | 0.12 | 0.12 | 0.12 | 0.12 | 0.12 | 0.12 | >29 | 0.12 |
| Rifampicin | 0.015 | 0.007 | 0.003 | 0.003 | 0.003 | 0.003 | 0.003 | 0.003 | 0.003 | 0.003 | 0.003 | 0.003 | 0.003 | 0.003 | 0.003 | 0.003 | >4.8 |

StrR – streptomycin resistance
InhR – isoniazid resistance
RifR – rifampicin resistance

AZAINDOLE COMPOUNDS, SYNTHESIS THEREOF, AND METHODS OF USING THE SAME

BACKGROUND

This application claims benefit of Indian Provisional Patent Application No. 3196/CHE/2013, filed Jul. 17, 2013, entitled "Azaindole Compounds. Synthesis Thereof, and Methods of Using the Same," and also claims benefit of a second and updated provisional application having the same serial number (3196/CHE/2013) and a filing date of Apr. 30, 2014, the entire contents of both of which are hereby incorporated by reference.

Tuberculosis (TB) continues to cause considerable morbidity and mortality worldwide, despite having an effective and economical quadruple drug therapy regimen, put in place 40 years ago (Raviglione, M. et al. Lancet 379, 1902-1913 (2012); World Health Organization. Global Tuberculosis Report (2012)). It is gratifying to see US Food and Drug Administration (FDA)'s recent accelerated approval of Janssen's Sirturo (bedaquiline) for multidrug-resistant tuberculosis (MDR-TB), putting an end Co four-decade-long lull for a new TB drug with novel mechanism of action (Cohen, J. Science 339, 130-131 (2013)). However, the impact of Sirturo on disease landscape and patient's lives needs to be seen; in the context of associated safety risks and the burden of post marketing studies.

The nitro-benzothiazinones (BTZs) and related compounds are known to inhibit decaprenylphosphoryl-β-D-ribose2'-epimerase1 (DprE1) involved in the conversion of decaprenylphosphoryl-β-D-ribose (DPR) to decaprenylphosphoryl-β-D-arabinofuranose (DPA), a precursor of mycobacterial cell wall arabinan (Trefzer, C. et al. J. Am. Chem. Soc. 132, 13663-13665). This reaction is catalysed by a heteromeric enzyme decaprenyl-phospho-ribose 2'-epimerase (DprE), which occurs via a sequential oxidation-reduction mechanism involving an intermediate (decaprenylphosphoryl-2-keto-β-D-erythro-pentofuranose, DPX). This enzyme is composed of two proteins encoded by the dprE1 and dprE2 genes. DprE1 enzyme is the FAD-containing oxidoreductase, while DprE2 is the NADH-dependent reductase (Mikusova, K. et al. J. Bacteriol. 187, 8020-8025 (2005); Makarov, V. et al. Science 324, 801-804 (2009)).

The identification of BTZ043 as a covalent inhibitor of DprE1 with potent antimycobacterial activity confirms the validity of this target for a novel TB therapy (Science 324, 801-804 (2009)). However, it remains to be understood whether non-nitro inhibitors of DprE1 will lead to efficacy in vivo? Additionally, is nanomolar cellular activity essential for in vivo efficacy? Greater understanding in relation to these aspects of DprE1 inhibition will significantly influence future TB drug discovery efforts directed at this target. Thus, a need exists in the art for additional compounds that target DprE1.

SUMMARY OF THE INVENTION

In some aspects, the invention provides, at least in part, a compound of formula (I):

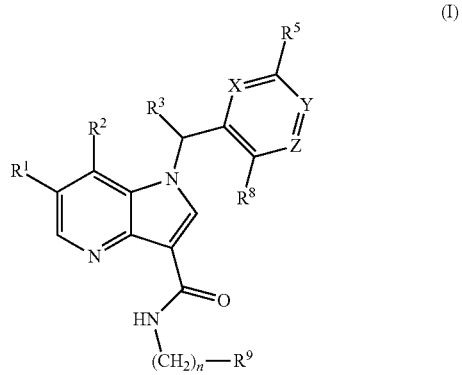

wherein
R$^1$ is selected from hydrogen, fluorine, bromine, —OCH$_3$ and methyl;
R$^2$ is hydrogen or methyl;
R$^3$ is hydrogen or methyl;
X is N or CR$^4$;
R$^4$ is selected from hydrogen, fluorine and —OCH$_3$;
R$^5$ is selected from hydrogen, fluorine, —CF$_3$ and —CN;
Y is N or CR$^6$;
R$^6$ is hydrogen or methyl;
Z is N or CR$^7$;
R$^7$ is selected from hydrogen, fluorine, —OCH$_3$, —OCHF$_2$, —OCH$_2$CF$_3$ and —N(CH$_3$)$_7$;
R$^8$ is selected from hydrogen, fluorine, methyl and —OCH$_3$;
n is 1 or 2;
R$^9$ is selected from fluorine, cyclopropyl, —OCH$_3$, —OH, —OCF$_3$, —CHF", —CH(F)CH$_3$ and —CH(OH)CH$_3$, or a pharmaceutically acceptable salt thereof.

In some aspects, the invention provides, at least in part, a pharmaceutical composition comprising a compound of formula (I), or a pharmaceutically acceptable salt thereof, and a pharmaceutically acceptable carrier or diluent.

In some aspects, the invention provides a compound of formula (I) or a pharmaceutically acceptable salt thereof, for use in the treatment of tuberculosis or a *Mycobacterium* infection.

In some aspects, the invention provides a compound of formula (I) for use in the manufacture of a medicament for the treatment of tuberculosis or a *Mycobacterium* infection.

In some aspects, the invention provides a method of treating tuberculosis or a *Mycobacterium* infection comprising administering to a subject in need thereof a therapeutically effective amount of a compound of formula (I) or a pharmaceutically acceptable salt thereof.

In some aspects, the invention provides a pharmaceutical composition comprising a compound of formula (I) or a pharmaceutically acceptable salt thereof, for use in the treatment of tuberculosis or a *Mycobacterium* infection.

In some aspects, the invention provides a compound of formula (I) or a pharmaceutically acceptable salt thereof, for use in the inhibition of DprE1.

In some aspects, the invention provides a compound of formula (I) for use in the manufacture of a medicament for inhibition of DprE1.

In some aspects, the invention provides a method of inhibiting DprE1 comprising administering to a therapeutically effective amount of a compound of formula (I) or a pharmaceutically acceptable salt thereof.

In some aspects, the invention provides a pharmaceutical composition comprising a compound of formula (I) or a pharmaceutically acceptable salt thereof, for inhibiting DprE1.

BRIEF DESCRIPTIONS OF THE DRAWINGS

Figure 4A:
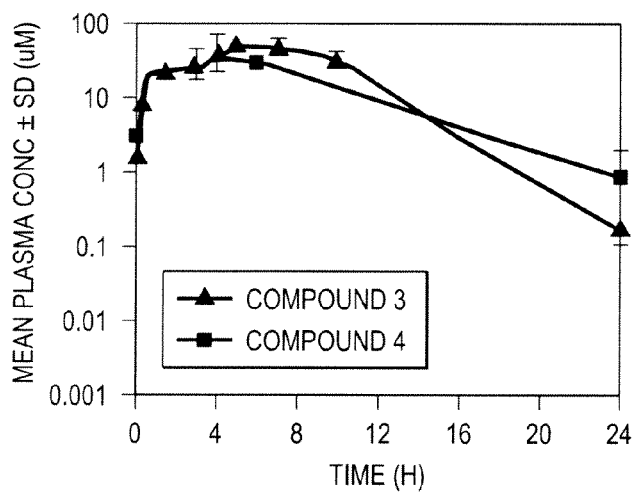
Figure 4B:
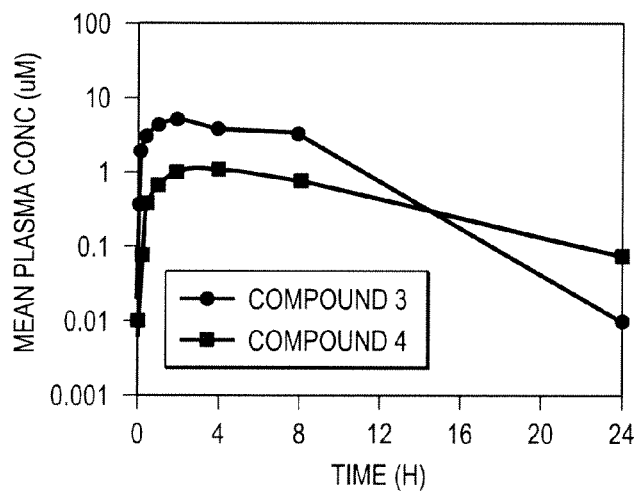
Figure 4C:
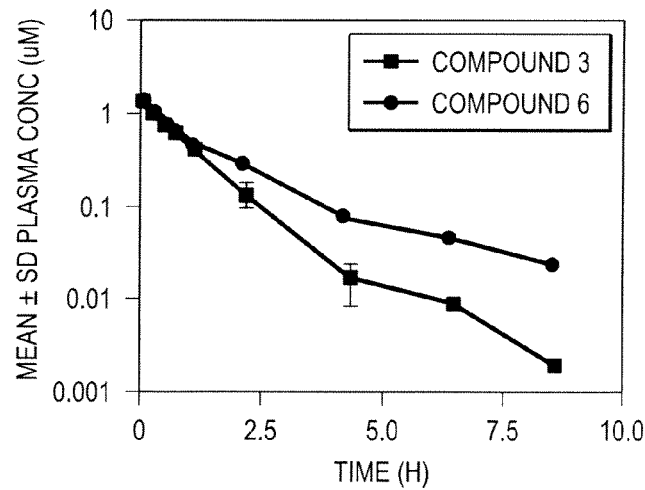

FIG. 4 illustrates (a) Time vs concentration profiles of compound 3 and 4 in mice following oral administration at 100mg/kg (with ABT), (b) Time vs concentration profiles of compound 3 and 4 in rat following oral administration at 30mg/kg (c) Time vs concentration profiles of compound 3 and 6 in rat following IV bolus at 0.5 and 2 mg/kg respectively.

Figure 5:
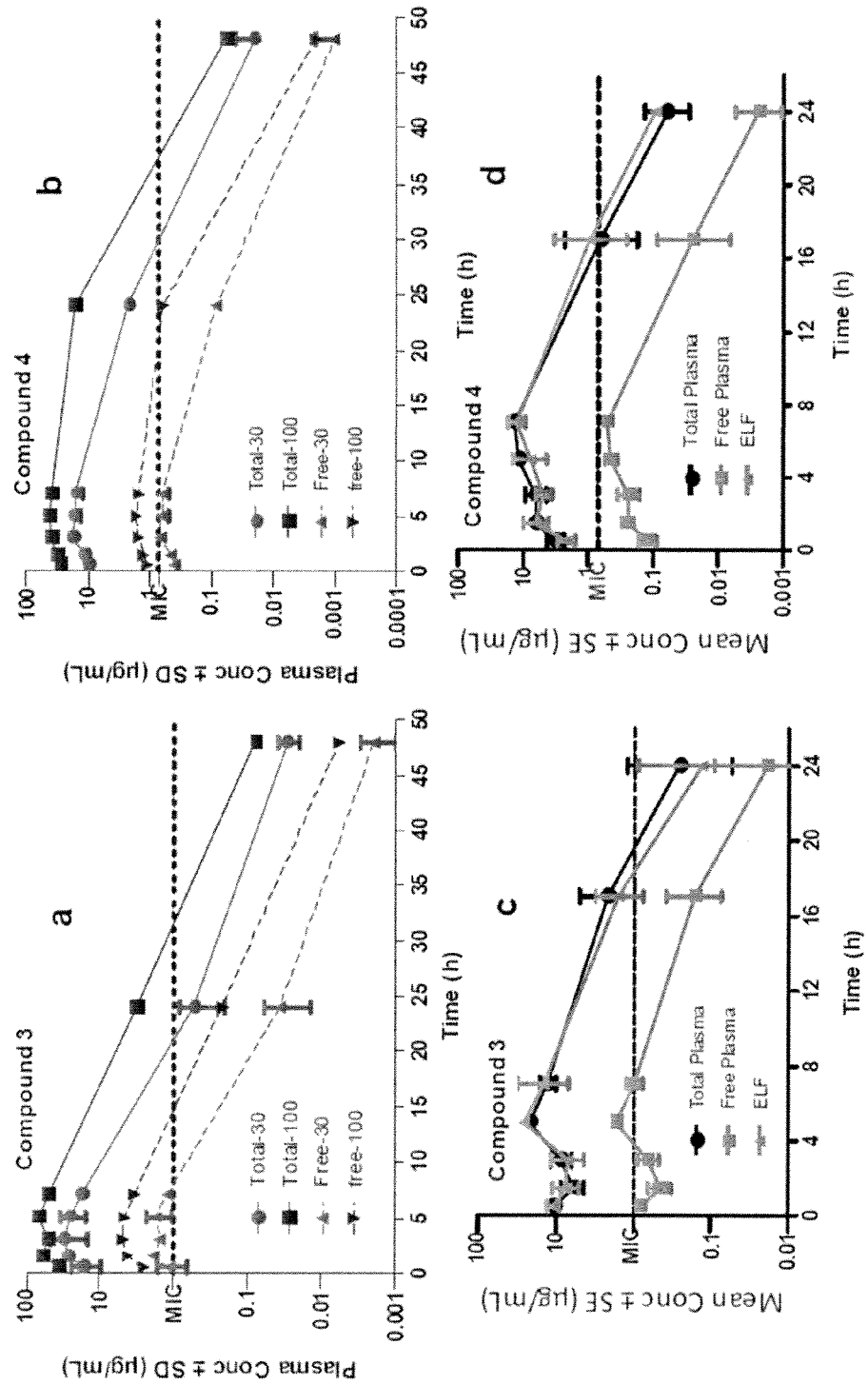

FIG. 5 illustrates (a) Time vs concentration profile of compound 3 in mice following multiple oral administration at 30 & 100mg/kg in chronically infected mice (with ABT), (b) Time vs concentration profile of compound 4 in mice following multiple oral administration at 30 & 100 mg/kg in chronically infected mice (with ABT), (c) ELF PK of compound 3 in healthy mice at 100 mg/kg, (d) ELF PK of compound 4 in healthy mice at 100 mg/kg.

Figure 6:
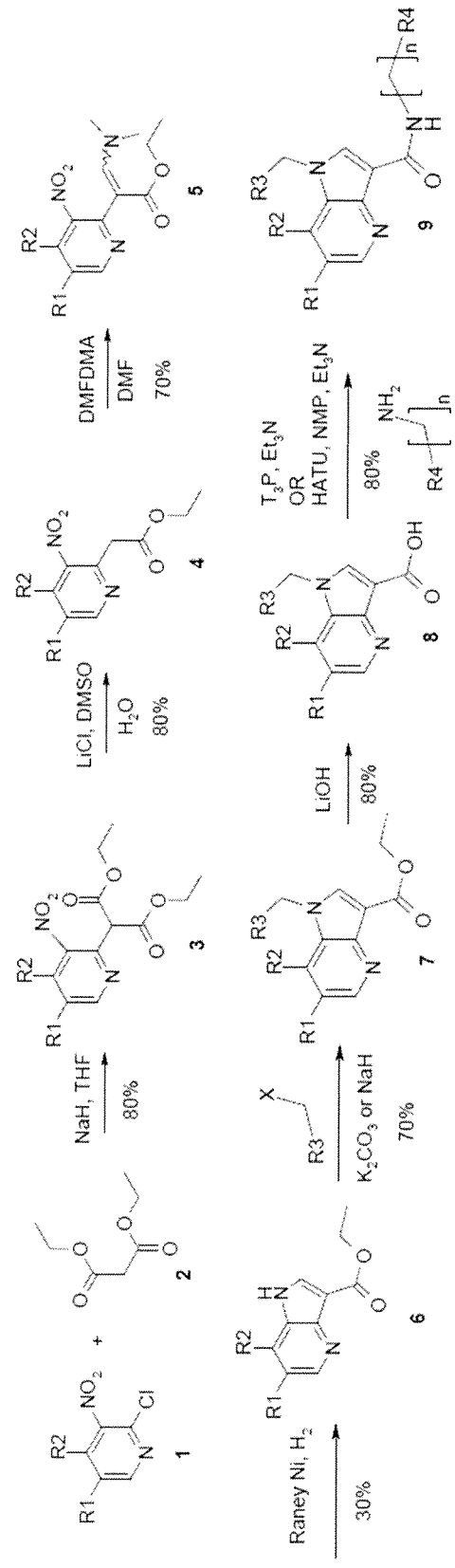

FIG. 6 illustrates Synthetic Scheme 1 for the synthesis of Intermediates 3-9.

Figure 7:
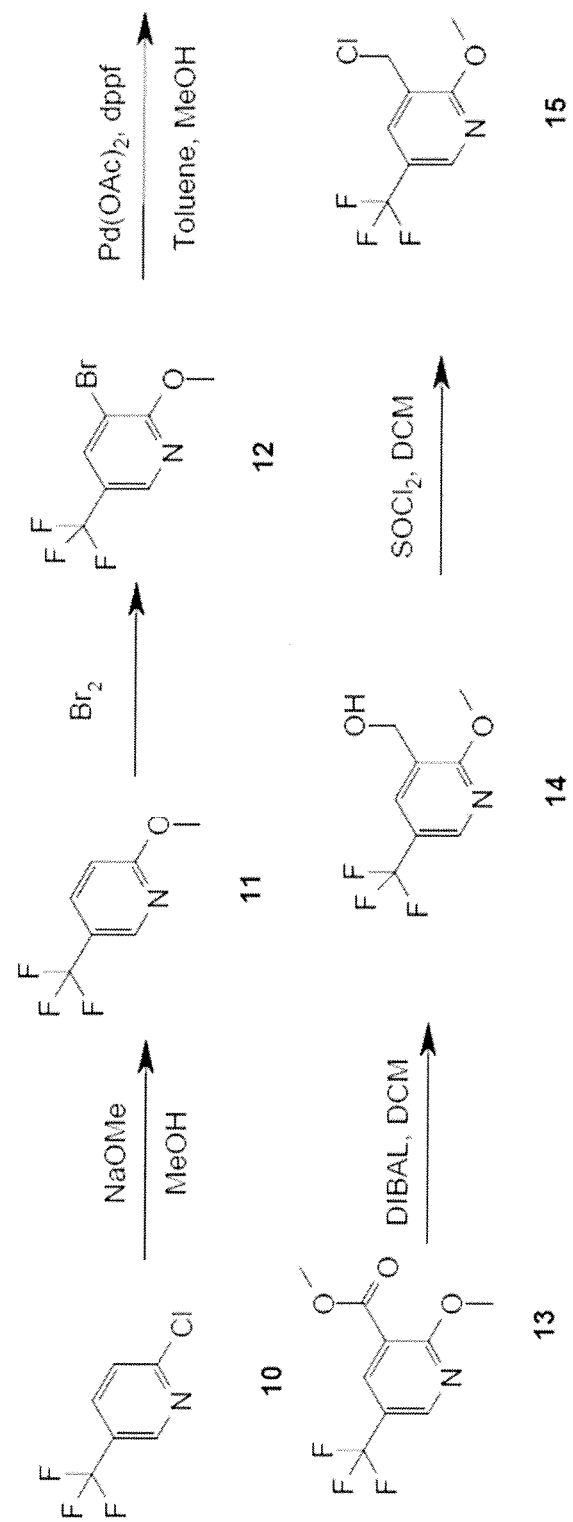

FIG. 7 illustrates Synthetic Scheme 2 for the synthesis of Intermediates 11-15.

Figure 8:
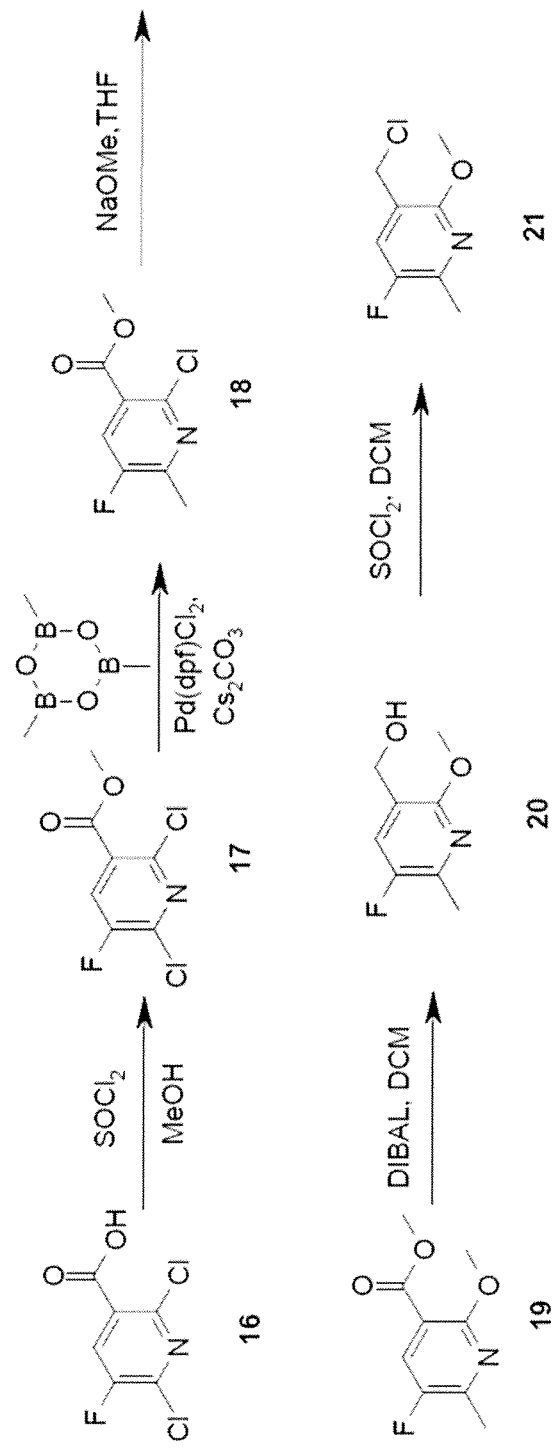

FIG. 8 illustrates Synthetic Scheme 3 for the synthesis of Intermediates 17-21.

Figure 9:
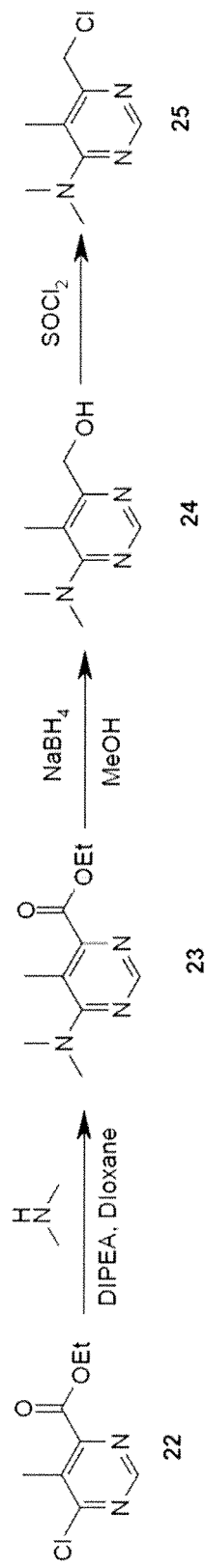

FIG. 9 illustrates Synthetic Scheme 4 for the synthesis of Intermediates 23-25.

Figure 10:
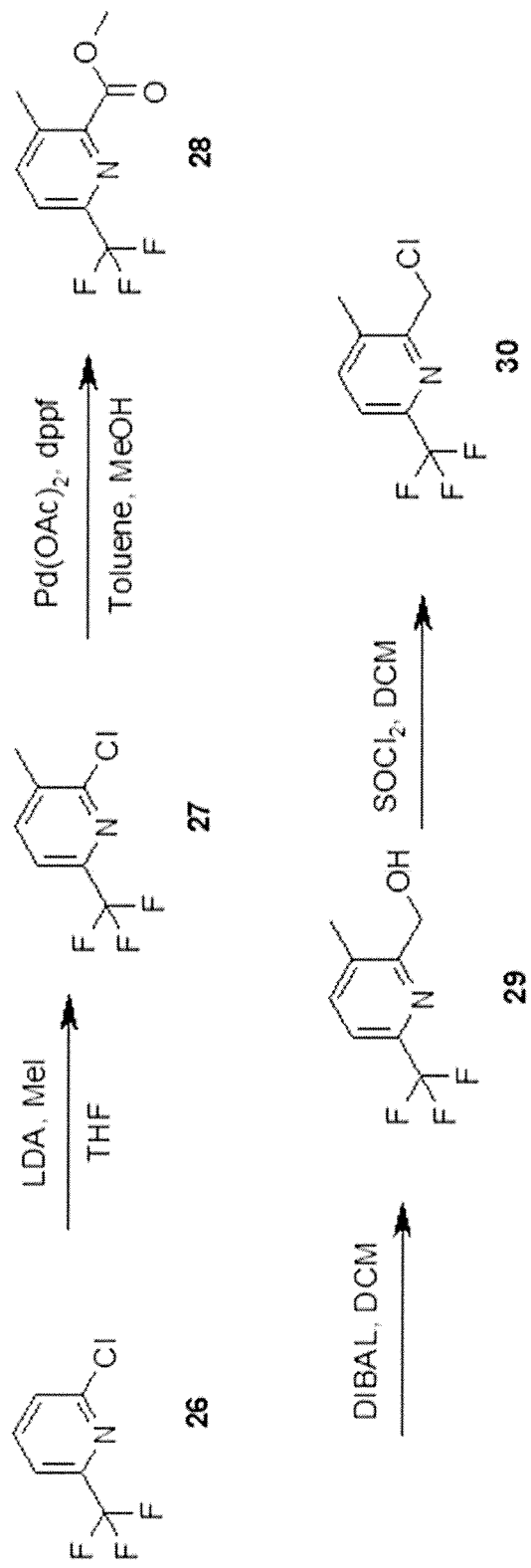

FIG. 10 illustrates Synthetic Scheme 5 for the synthesis of Intermediates 27-30.

Figure 11:
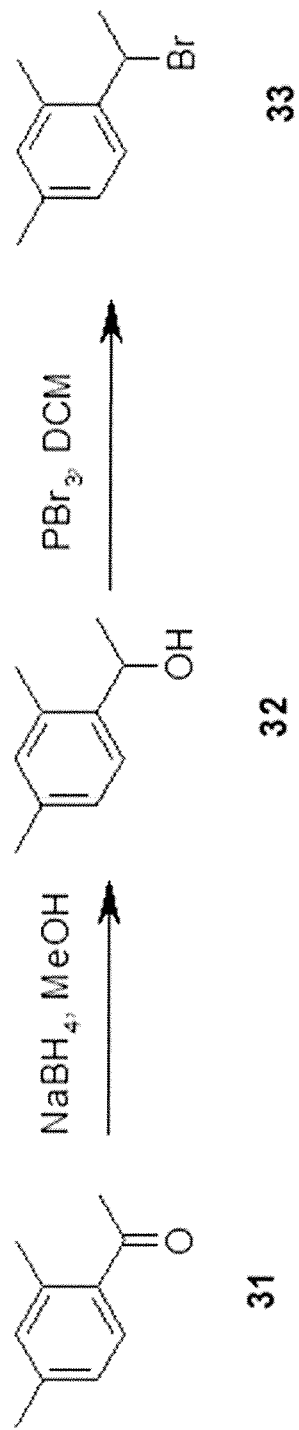

FIG. 11 illustrates Synthetic Scheme 6 for the synthesis of Intermediates 32-33.

Figure 12:
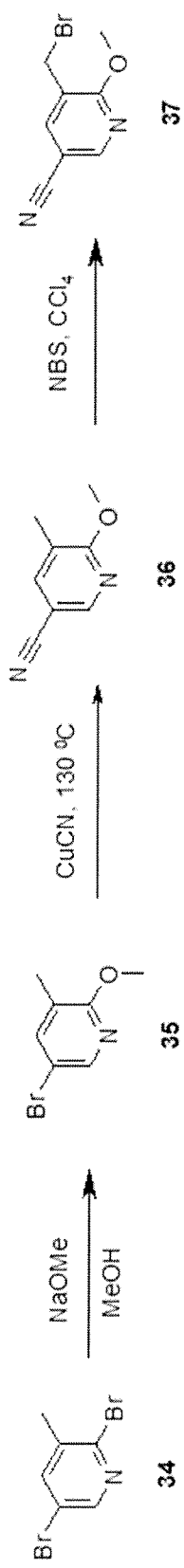

FIG. 12 illustrates Synthetic Scheme 7 for the synthesis of Intermediates 35-37.

Figure 13:
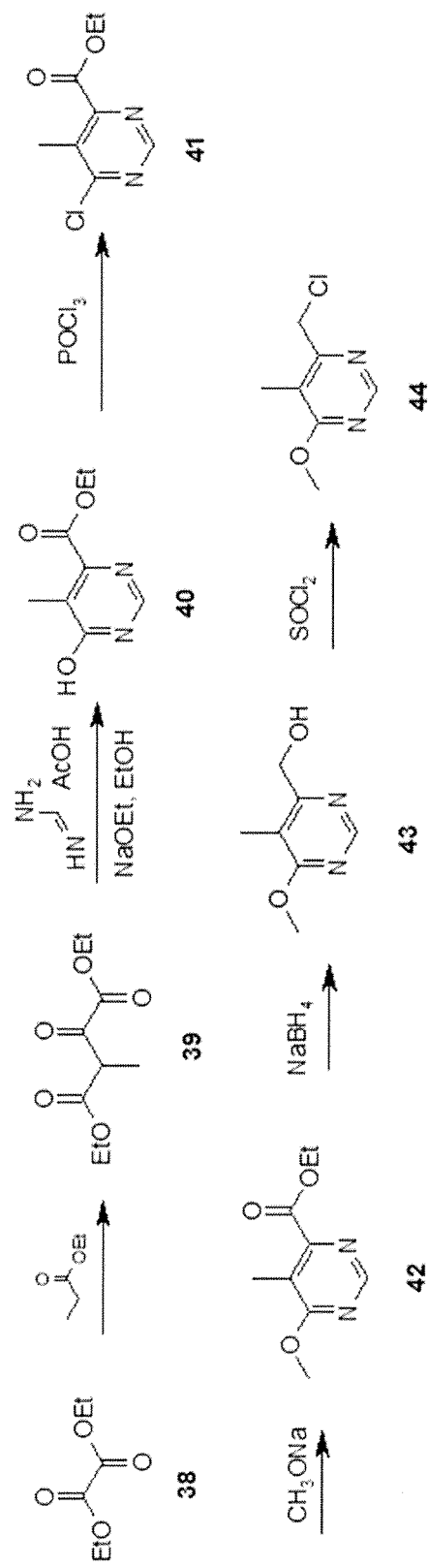

FIG. 13 illustrates Synthetic Scheme 8 for the synthesis of Intermediates 39-44.

Figure 14:
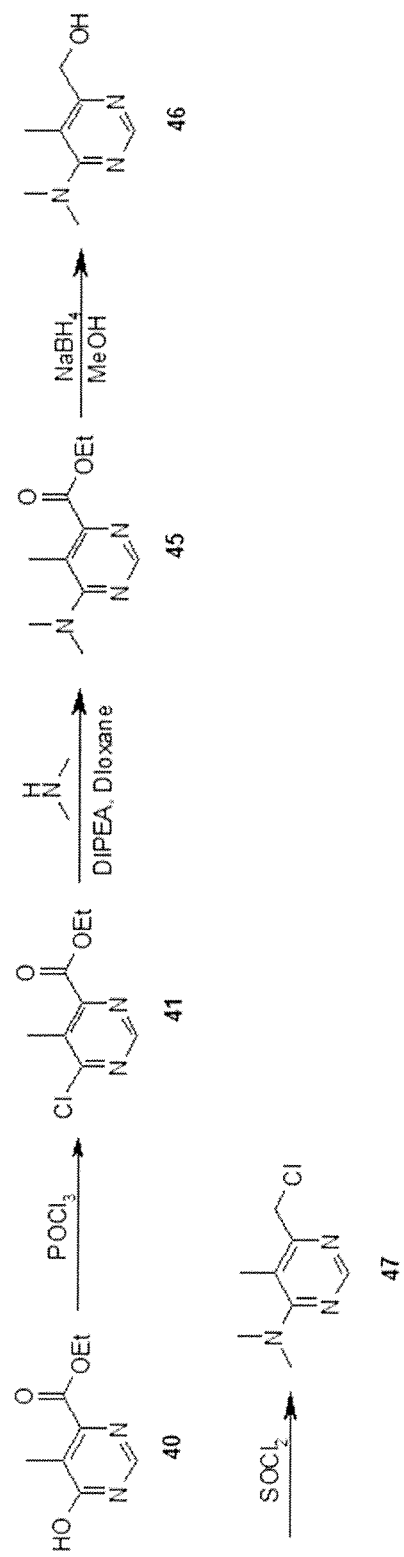

FIG. 14 illustrates Synthetic Scheme 9 for the synthesis of Intermediates 41-47.

Figure 15:
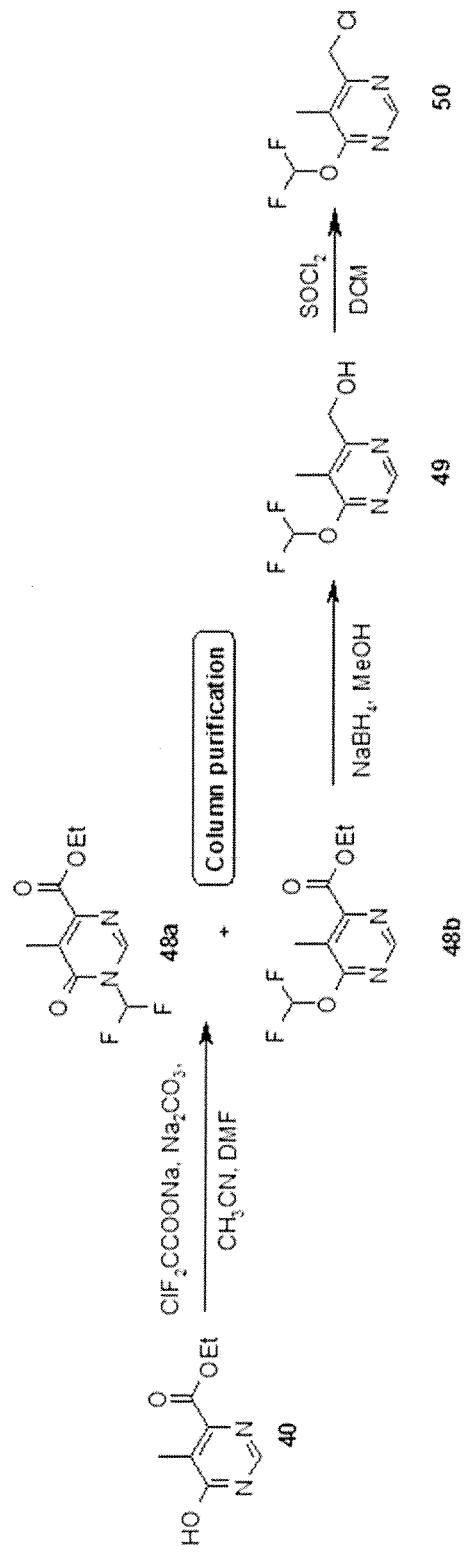

FIG. 15 illustrates Synthetic Scheme 10 for the synthesis of Intermediates 48a and 48b-50.

Figure 16:
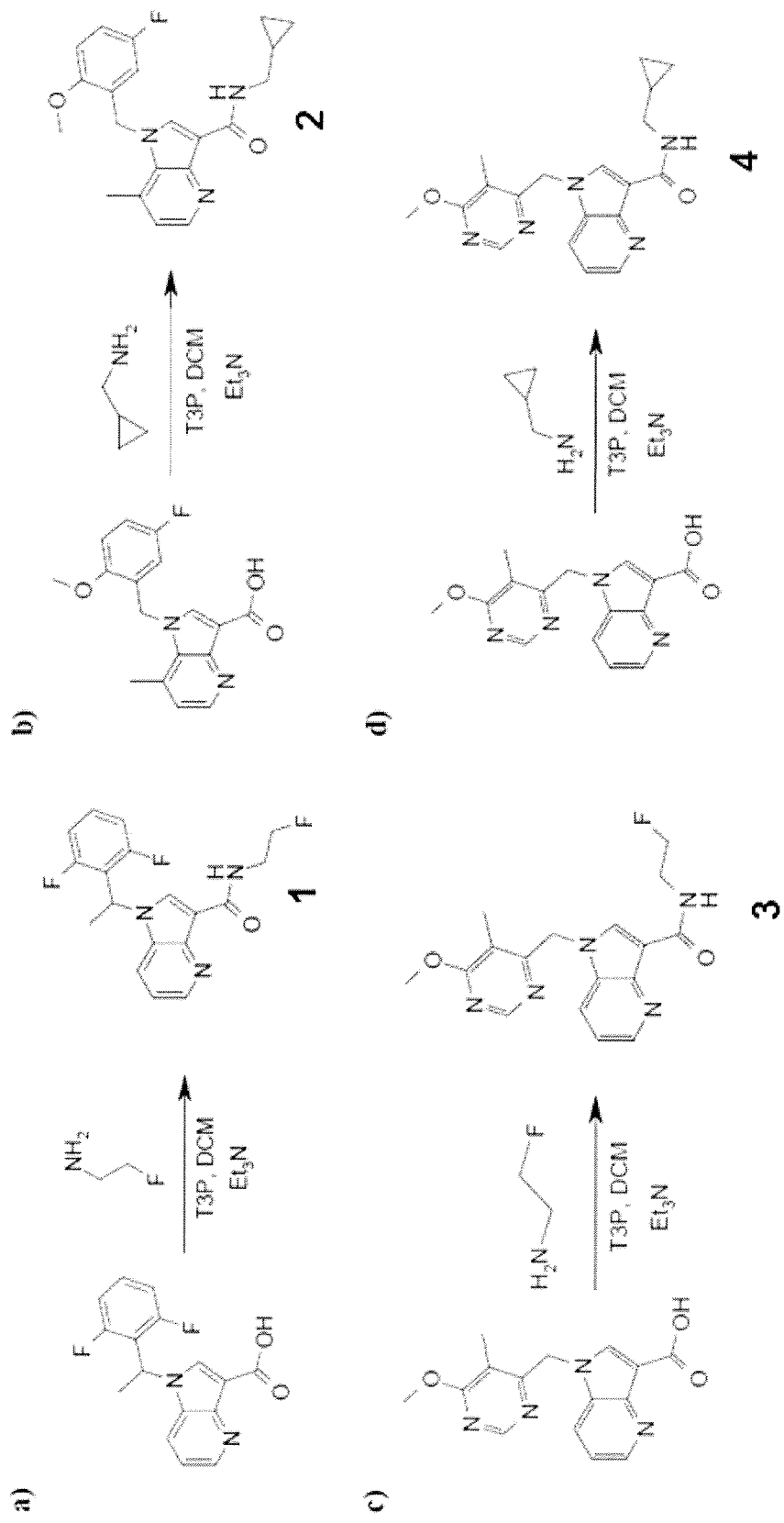

FIG. 16 illustrates the synthesis of compounds in (a)-(d) Examples 1-4.

Figure 17:
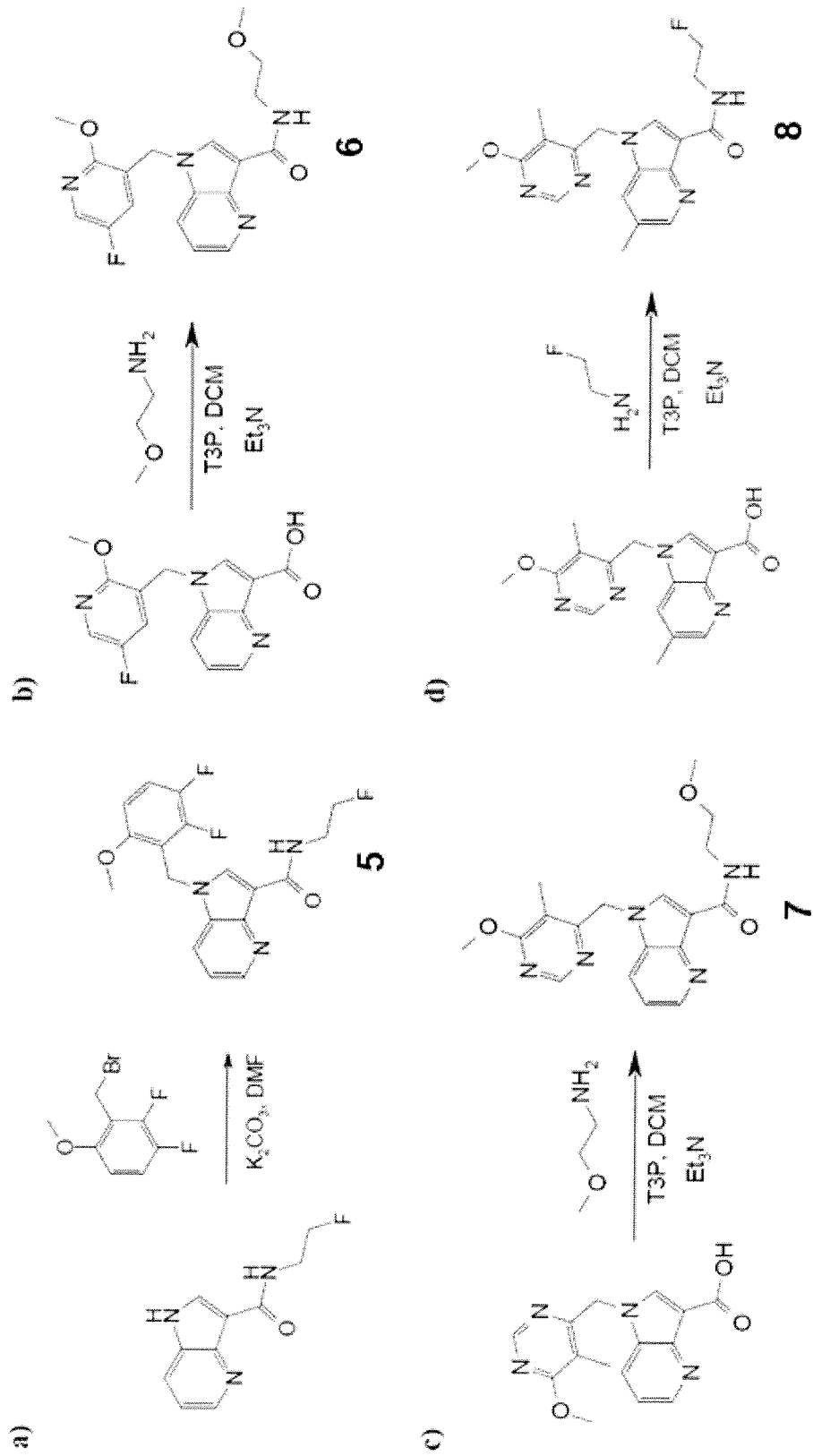

FIG. 17 illustrates the synthesis of compounds in (a)-(d) Examples 5-8.

Figure 18:
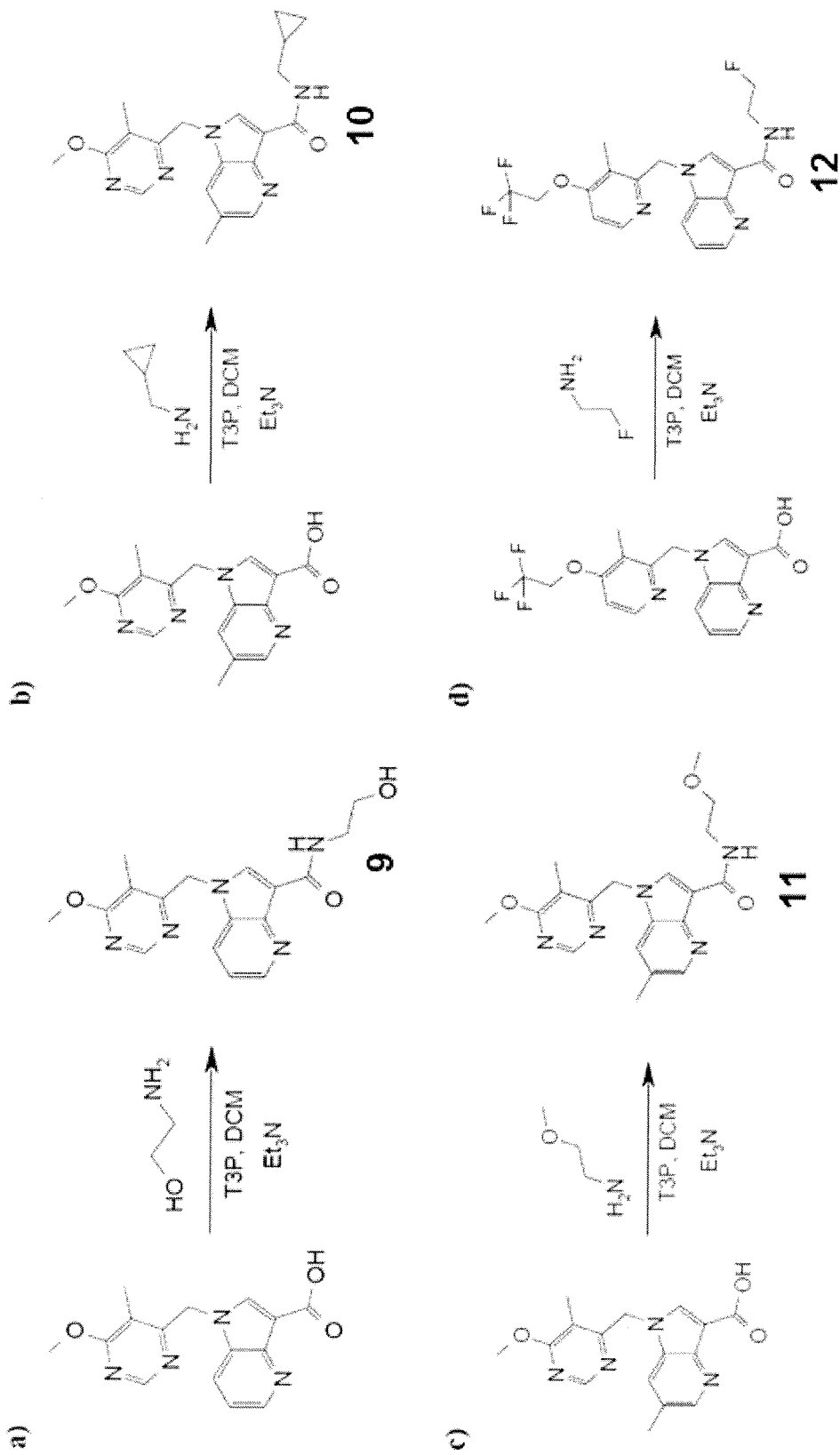

FIG. 18 illustrates the synthesis of compounds in (a)-(d) Examples 9-12.

Figure 19:
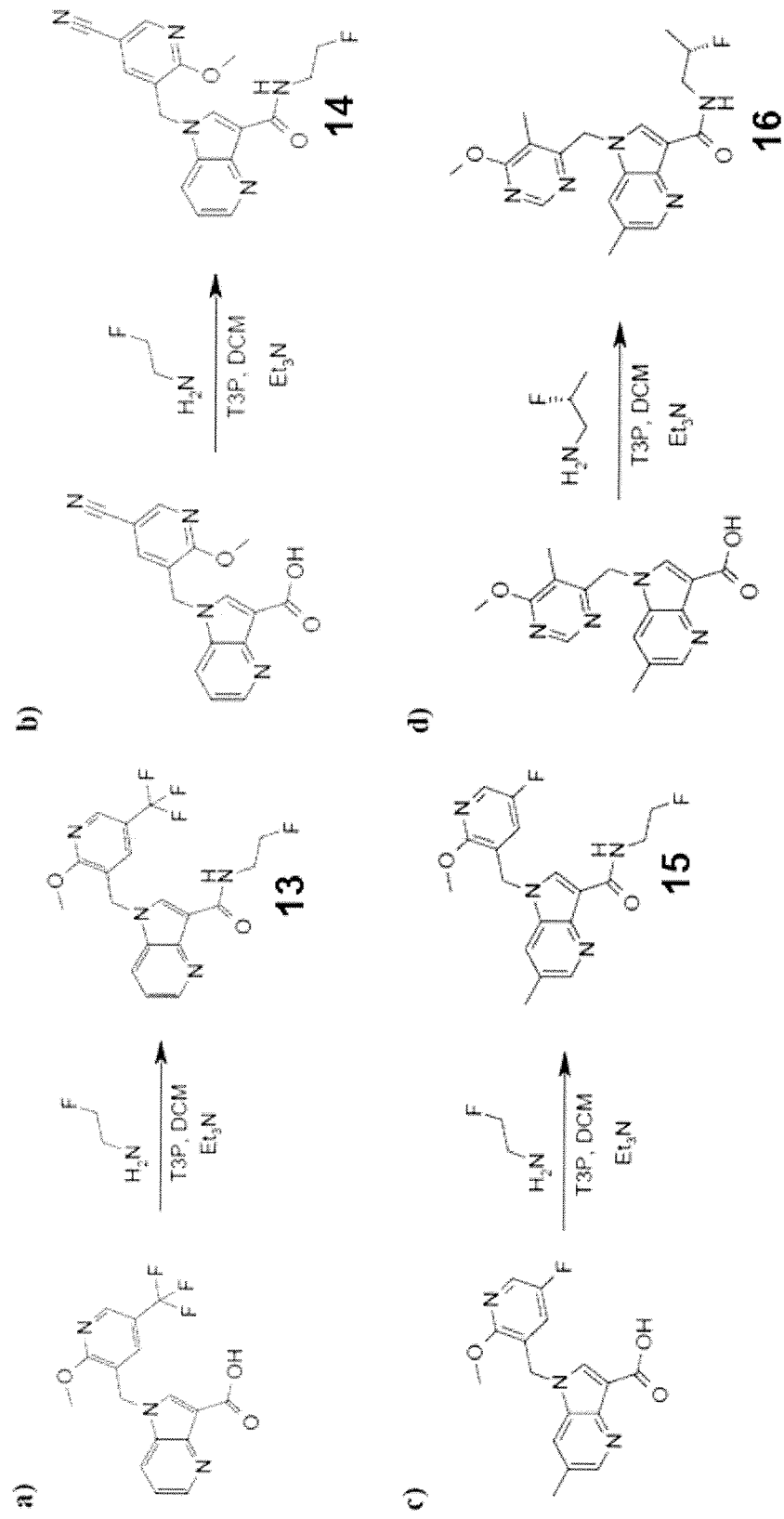

FIG. 19 illustrates the synthesis of compounds in (a)-(d) Examples 13-16.

Figure 20:
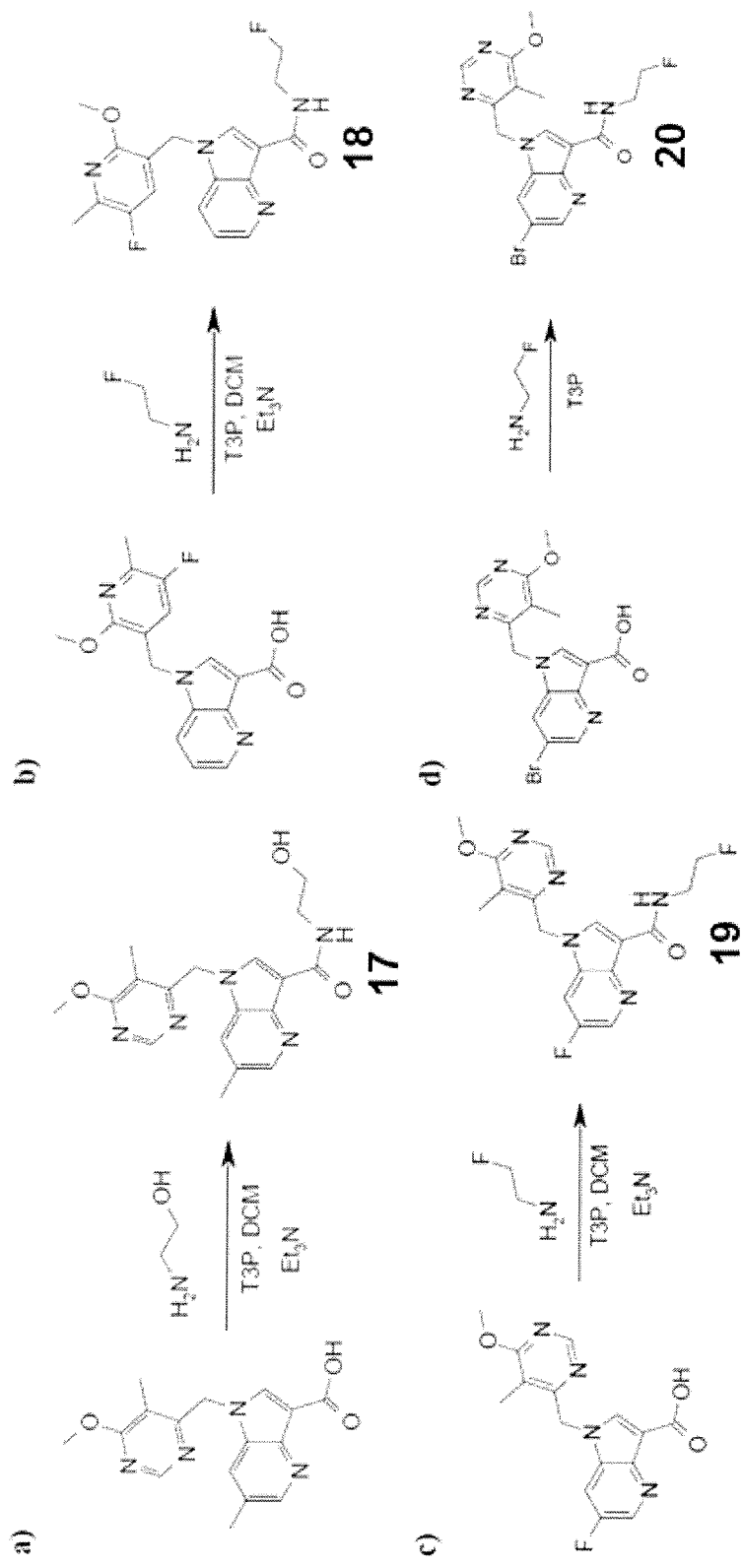

FIG. 20 illustrates the synthesis of compounds in (a)-(d) Examples 17-20.

Figure 21:
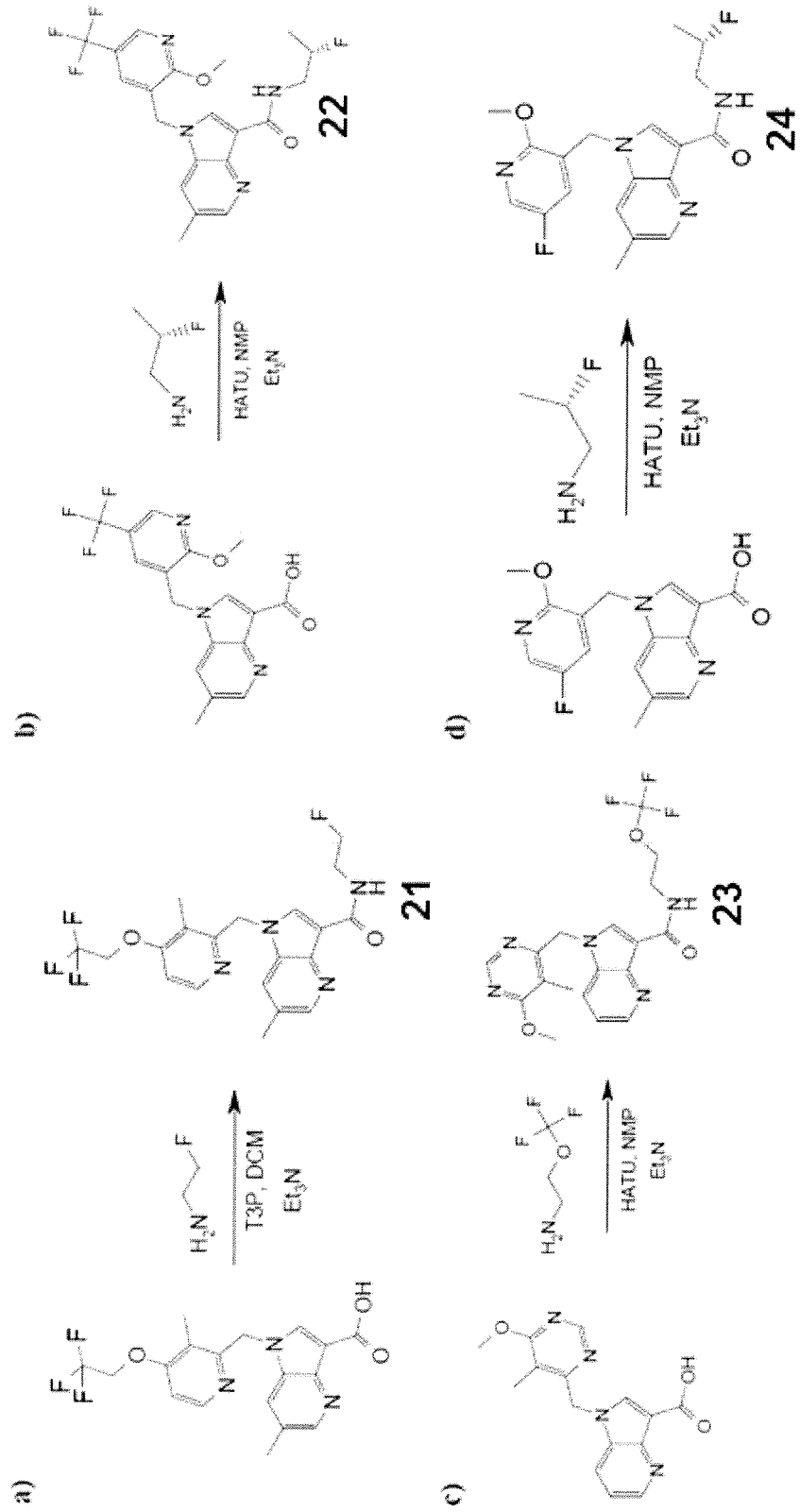

FIG. 21 illustrates the synthesis of compounds in (a)-(d) Examples 21-24.

Figure 22:
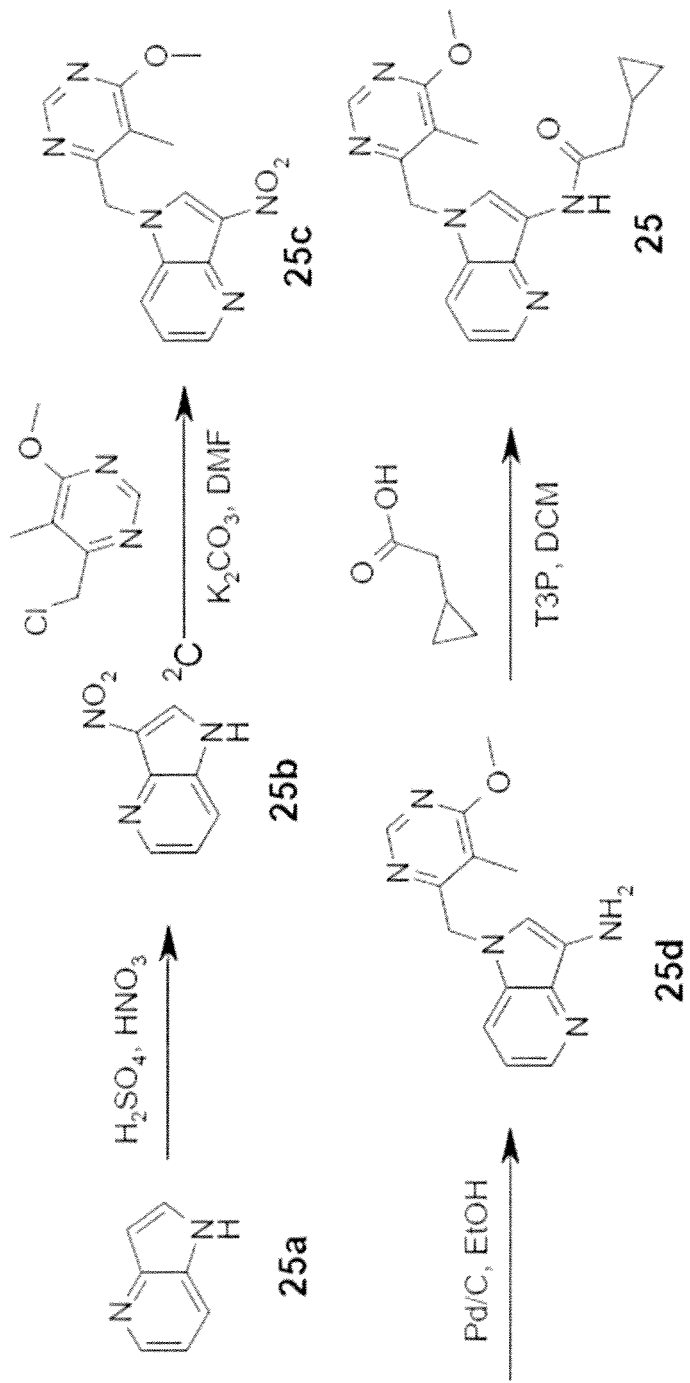

FIG. 22 illustrates the synthesis of compounds in Example 25.

Figure 23:
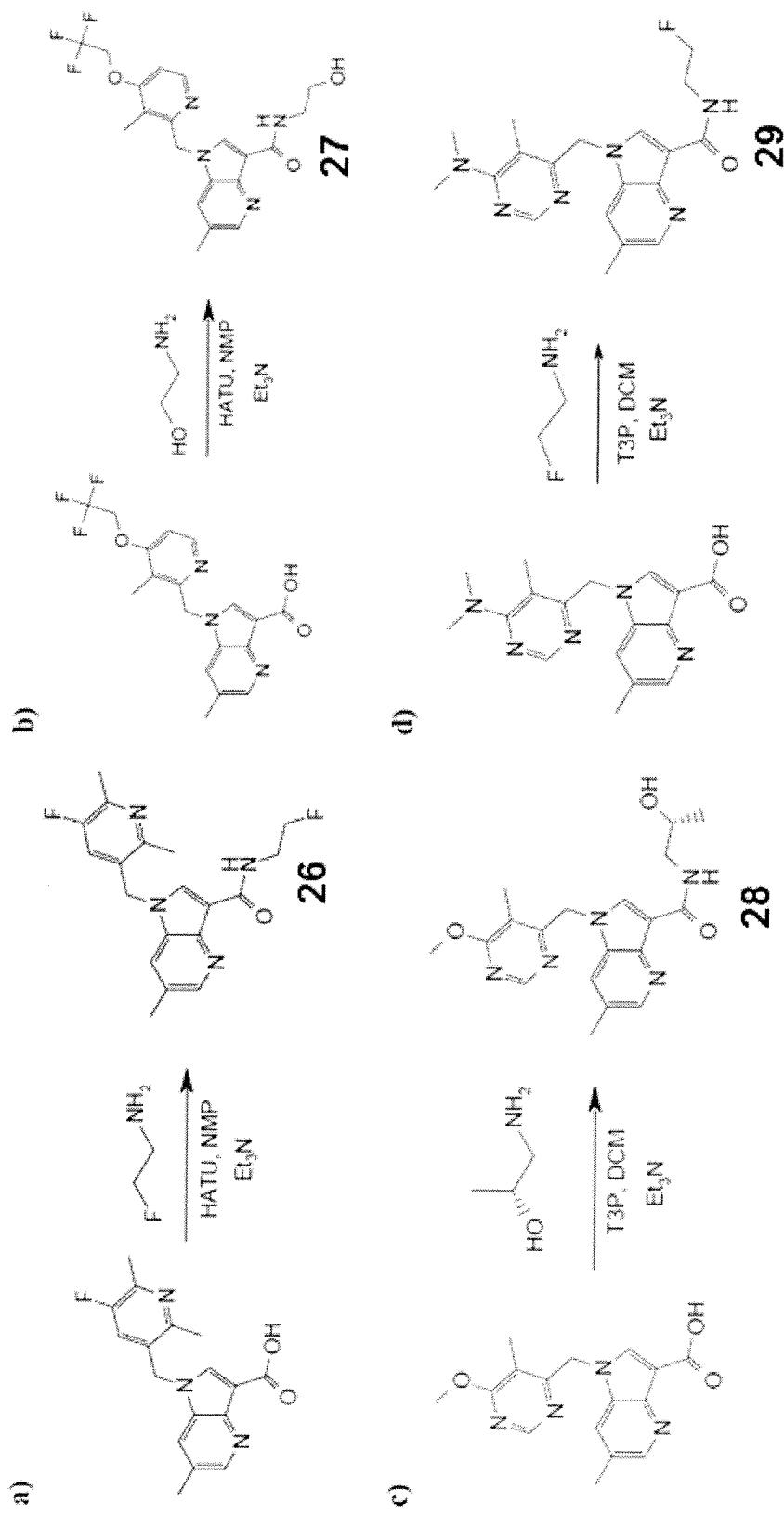

FIG. 23 illustrates the synthesis of compounds in (a)-(c) Examples 26-29.

Figure 24:
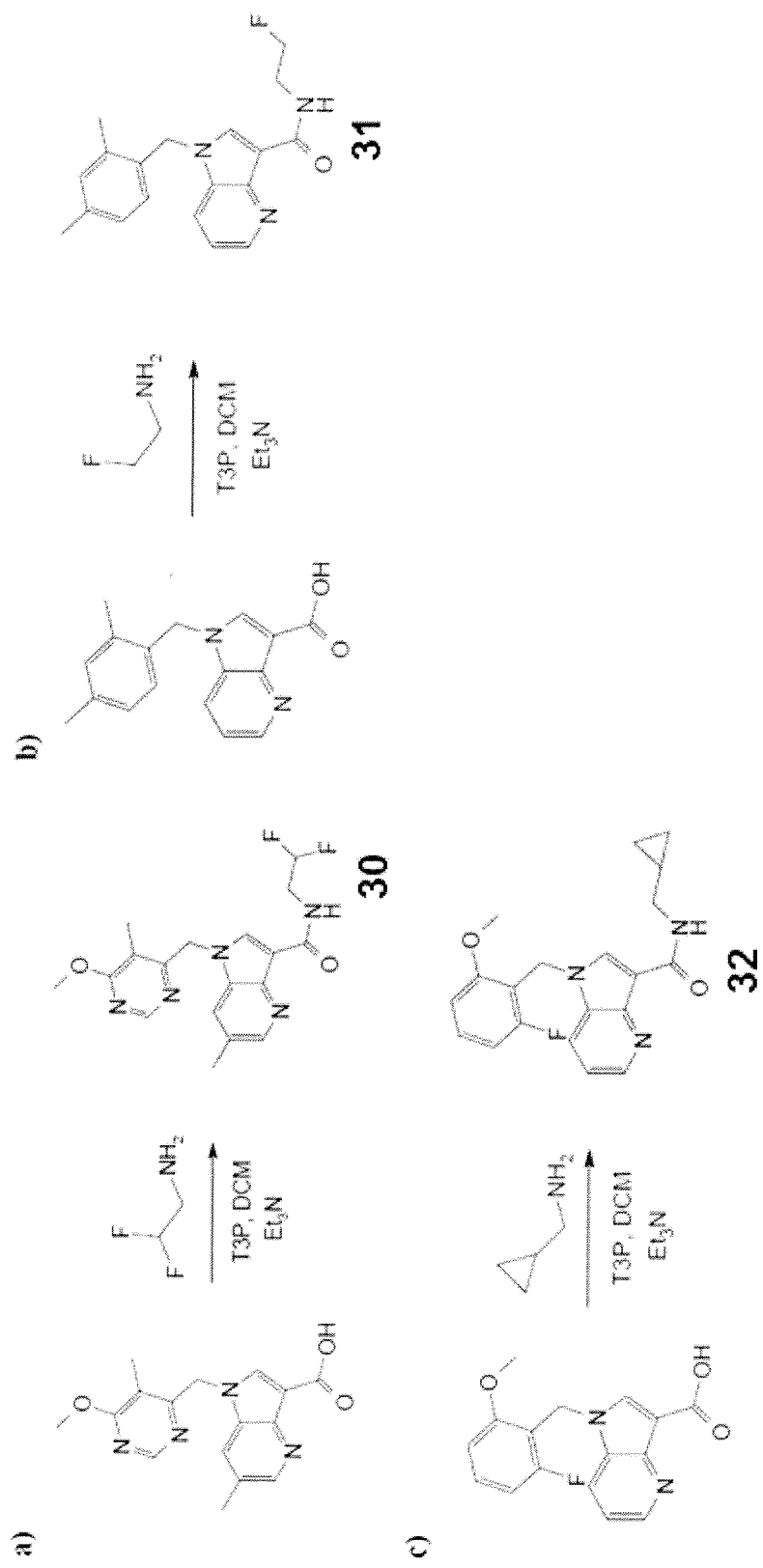

FIG. 24 illustrates the synthesis of compounds in (a)-(c) Examples 30-32.

FIG. 25 illustrates Table 2, Pathogen specificity.

FIG. 26 shows Table 3, Activity against drug sensitive and drug resistant Mtb.

DETAILED DESCRIPTION OF THE INVENTION

Compounds

In some aspects, the invention provides compounds of Formula (I), wherein

In some aspects, the invention provides, at least in part, a compound of formula (I):

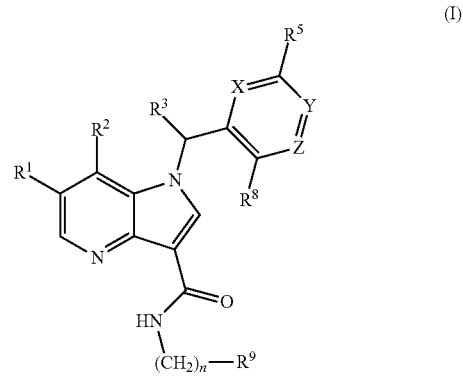

wherein
$R^1$ is selected from hydrogen, fluorine, bromine, —OCH$_3$ and methyl;
$R^2$ is hydrogen or methyl;
$R^3$ is hydrogen or methyl;
X is N or $CR^4$;
$R^4$ is selected from hydrogen, fluorine and —OCH$_3$;
$R^5$ is selected from hydrogen, fluorine, —CF$_3$ and —CN;
Y is N or $CR^6$;
$R^6$ is hydrogen or methyl;
Z is N or $CR^7$;
$R^7$ is selected from hydrogen, fluorine, —OCH$_3$, —OCHF$_7$, —OCH$_2$CF$_3$ and —N(CH$_3$)$_2$;
$R^8$ is selected from hydrogen, fluorine, methyl and —OCH$_3$;
n is 1 or 2;
$R^9$ is selected from fluorine, cyclopropyl, —OCH$_3$, —OH, —OCF$_3$, CHF$_2$, —CH(F)CH$_3$ and —CH(OH)CH$_3$, or a pharmaceutically acceptable salt thereof.

In some aspects, $R^1$ and $R^2$ are each hydrogen.
In some aspects, $R^1$ is hydrogen and $R^2$ is methyl.
In some aspects, $R^1$ is selected from fluorine, bromine and methyl and $R^2$ is hydrogen.
In some aspects, $R^1$, $R^2$ and $R^3$ are each hydrogen.
In some aspects, $R^1$ is methyl and $R^2$ and $R^3$ are each hydrogen.
In some aspects, n is 1 and $R^9$ is cyclopropyl.
In some aspects, n is 1 and $R^9$ is —CH(F)CH$_3$.
In some aspects, n is 1 and $R^9$ is —CHF$_2$.
In some aspects, n is 1 and $R^9$ is —CH(OH)CH$_3$.
In some aspects, n is 2 and $R^9$ is fluorine.
In some aspects, n is 2 and $R^9$ is —OMe.
In some aspects, n is 2 and $R^9$ is —OH.
In some aspects, n is 2 and $R^9$ is —OCF$_3$.
In some aspects, X is N, $R^5$ is hydrogen, Y is N, Z is $CR^7$, $R^7$ is —OMe and $R^8$ is methyl.

In some aspects, X is $CR^4$, $R^4$ is hydrogen, $R^5$ is selected from fluorine, —CN and —$CF_3$, Y is $CR^6$, $R^6$ is hydrogen, Z is N and $R^8$ is —OMe.

In some aspects, $R^1$ is hydrogen, $R^2$ is hydrogen, $R^3$ is hydrogen, X is N, $R^5$ is hydrogen, Y is N, Z is $CR^7$, $R^7$ is —OMe and $R^8$ is methyl.

In some aspects, $R^1$ is methyl, $R^2$ is hydrogen, $R^3$ is hydrogen, X is N, $R^5$ is hydrogen, Y is N, Z is $CR^7$, $R^7$ is —OMe and $R^8$ is methyl.

In some aspects, $R^1$ is fluorine, $R^2$ is hydrogen, $R^3$ is hydrogen, X is N. $R^5$ is hydrogen, Y is N, Z is $CR^7$, $R^7$ is —OMe and $R^8$ is methyl.

In some aspects, $R^1$ is bromine, $R^2$ is hydrogen, $R^3$ is hydrogen, X is N, $R^5$ is hydrogen, Y is N, Z is $CR^7$, $R^7$ is —OMe and $R^8$ is methyl.

In some aspects, $R^1$ is hydrogen, $R^2$ is hydrogen, $R^3$ is methyl, X is $CR^4$, $R^4$ is fluorine, $R^5$ is hydrogen, Y is $CR^6$, $R^6$ is hydrogen, Z is $CR^7$, $R^7$ is hydrogen, $R^8$ is fluorine, n is 2 and $R^9$ is fluorine.

In some aspects, $R^1$ is hydrogen, $R^2$ is methyl. $R^3$ is hydrogen, X is $CR^4$, $R^4$ is —OMe, $R^5$ is hydrogen, Y is $CR^6$, $R^6$ is hydrogen, Z is $CR^7$, $R^7$ is fluorine, $R^8$ is hydrogen, n is 1 and $R^9$ is cyclopropyl.

In some aspects, $R^1$ is hydrogen, $R^2$ is hydrogen, $R^3$ is hydrogen, X is N, $R^5$ is hydrogen, Y is N, Z is $CR^7$, $R^7$ is —OMe. $R^8$ is methyl, n is 2 and $R^9$ is fluorine.

In some aspects, $R^1$ is hydrogen, $R^2$ is hydrogen, $R^3$ is hydrogen, X is N, $R^5$ is hydrogen, Y is N, Z is $CR^7$, $R^7$ is —OMe, $R^8$ is methyl, n is 1 and $R^9$ is cyclopropyl.

In some aspects, $R^1$ is hydrogen, $R^2$ is hydrogen, $R^3$ is hydrogen, X is $CR^4$, $R^4$ is —OMe, $R^5$ is hydrogen, Y is $CR^6$, $R^6$ is hydrogen, Z is $CR^7$, $R^7$ is fluorine. $R^8$ is fluorine, n is 2 and $R^9$ is fluorine.

In some aspects, $R^1$ is hydrogen, $R^2$ is hydrogen, $R^3$ is hydrogen, X is $CR^4$, $R^4$ is hydrogen, $R^5$ is hydrogen. Y is $CR^6$, $R^6$ is hydrogen, Z is N, $R^8$ is —OMe, n is 2 and $R^9$ is —OMe.

In some aspects, $R^1$ is hydrogen, $R^2$ is hydrogen, $R^3$ is hydrogen, X is N, $R^5$ is hydrogen. Y is N, Z is $CR^7$, $R^7$ is —OMe, $R^8$ is methyl, n is 2 and $R^9$ is —OMe.

In some aspects, $R^1$ is methyl. $R^2$ is hydrogen, $R^3$ is hydrogen, X is N, $R^5$ is hydrogen, Y is N, Z is $CR^7$, $R^7$ is —OMe, $R^8$ is methyl, n is 2 and $R^9$ is fluorine.

In some aspects, $R^1$ is hydrogen, $R^2$ is hydrogen, $R^3$ is hydrogen, X is N, $R^5$ is hydrogen, Y is N, Z is $CR^7$, $R^7$ is —OMe, $R^8$ is methyl, n is 2 and $R^9$ is —OH.

In some aspects, $R^1$ is methyl, $R^2$ is hydrogen, $R^3$ is hydrogen, X is N, $R^5$ is hydrogen, Y is N, Z is $CR^7$, $R^7$ is —OMe, $R^8$ is methyl, n is 1 and $R^9$ is cyclopropyl.

In some aspects, $R^1$ is methyl, $R^2$ is hydrogen, $R^3$ is hydrogen, X is N, $R^5$ is hydrogen, Y is N, Z is $CR^7$, $R^7$ is —OMe, $R^8$ is methyl, n is 2 and $R^9$ is —OMe.

In some aspects, $R^1$ is methyl, $R^2$ is hydrogen, $R^3$ is hydrogen, X is N, $R^5$ is hydrogen, Y is $CR^6$, $R^6$ is hydrogen, Z is $CR^7$ and $R^7$ is —$OCH_2CF_3$, $R^8$ is methyl, n is 2 and $R^9$ is fluorine.

In some aspects, $R^1$ is hydrogen, $R^2$ is hydrogen, $R^3$ is hydrogen, X is $CR^4$, $R^4$ is hydrogen, $R^5$ is —$CF_3$, Y is $CR^6$, $R^6$ is hydrogen, Z is N, $R^8$ is —OMe, n is 2 and $R^9$ is fluorine.

In some aspects, $R^1$ is hydrogen, $R^2$ is hydrogen, $R^3$ is hydrogen, X is $CR^4$, $R^4$ is hydrogen, $R^5$ is —CN, Y is $CR^6$, $R^6$ is hydrogen, Z is N, $R^8$ is —OMe, n is 2 and $R^9$ is fluorine.

In some aspects, $R^1$ is methyl, $R^2$ is hydrogen, $R^3$ is hydrogen, X is $CR^4$, $R^4$ is hydrogen, $R^5$ is fluorine, Y is $CR^6$, $R^6$ is hydrogen, Z is N. $R^8$ is —OMe, n is 2 and $R^9$ is fluorine.

In some aspects, $R^1$ is methyl, $R^2$ is hydrogen, $R^3$ is hydrogen, X is N, $R^5$ is hydrogen, Y is N, Z is $CR^7$, $R^7$ is —OMe, $R^8$ is methyl, n is 1 and $R^9$ is $CH(F)CH_3$.

In some aspects, $R^1$ is methyl, $R^2$ is hydrogen, $R^3$ is hydrogen, X is N. $R^5$ is hydrogen, Y is N, Z is $CR^7$, $R^7$ is —OMe, $R^8$ is methyl, n is 2 and $R^9$ is —OH.

In some aspects, $R^1$ is hydrogen, $R^2$ is hydrogen, $R^3$ is hydrogen, X is $CR^4$, $R^4$ is hydrogen, $R^5$ is fluorine, Y is $CR^6$, $R^6$ is methyl, Z is N, $R^8$ is —OMe n is 2 and $R^9$ is fluorine.

In some aspects, $R^1$ is fluorine. $R^2$ is hydrogen, $R^3$ is hydrogen, X is N, $R^5$ is hydrogen, Y is N, Z is $CR^7$, $R^7$ is —OMe, $R^8$ is methyl, n is 2 and $R^9$ is fluorine.

In some aspects, $R^1$ is bromine, $R^2$ is hydrogen, $R^3$ is hydrogen, X is N, $R^5$ is hydrogen, Y is N, Z is $CR^7$, $R^7$ is —OMe, $R^8$ is methyl, n is 2 and $R^9$ is fluorine.

In some aspects, $R^1$ is methyl, $R^2$ is hydrogen, $R^3$ is hydrogen, X is N, $R^5$ is hydrogen, Y is $CR^6$, $R^6$ is hydrogen, Z is $CR^7$, $R^7$ is —$OCH_2CF_3$, $R^8$ is methyl, n is 2 and $R^9$ is fluorine.

In some aspects, $R^1$ is methyl, $R^2$ is hydrogen, $R^3$ is hydrogen, X is $CR^4$, $R^4$ is hydrogen, $R^5$ is —$CF_3$, Y is $CR^6$, $R^6$ is hydrogen, Z is N, $R^8$ is —OMe, n is 1 and $R^9$ is $CH(F)CH_3$.

In some aspects, $R^1$ is hydrogen, $R^2$ is hydrogen, $R^3$ is hydrogen, X is N, $R^5$ is hydrogen, Y is N, Z is $CR^7$, $R^7$ is —OMe, $R^8$ is methyl, n is 2 and $R^9$ is —$OCF_3$.

In some aspects, $R^1$ is methyl, $R^2$ is hydrogen, $R^3$ is hydrogen, X is $CR^4$, $R^4$ is hydrogen, $R^5$ is fluorine, Y is $CR^6$, $R^6$ is hydrogen, Z is N, $R^8$ is —OMe, n is 1 and $R^9$ is —$CH(F)CH_3$.

In some aspects, R1 is hydrogen, R2 is hydrogen, R3 is hydrogen, X is N, R5 is hydrogen, Y is N, Z is $CR^7$, $R^7$ is —OMe, $R^8$ is methyl, n is 1 and $R^9$ is cyclopropyl.

In some aspects, $R^1$ is methyl, $R^2$ is hydrogen, $R^3$ is hydrogen, X is $CR^4$, $R^4$ is hydrogen, $R^5$ is fluorine, Y is $CR^6$, $R^6$ is methyl, Z is N, $R^8$ is methyl, n is 2 and $R^9$ is fluorine.

In some aspects, $R^1$ is methyl, $R^2$ is hydrogen, $R^3$ is hydrogen, X is N, $R^5$ is hydrogen, Y is $CR^6$, $R^6$ is hydrogen, Z is $CR^7$, $R^7$ is —$OCH_2CF_3$, $R^8$ is methyl, n is 2 and $R^9$ is —OH.

In some aspects, $R^1$ is methyl, $R^2$ is hydrogen, $R^3$ is hydrogen, X is N, $R^5$ is hydrogen, Y is N, Z is $CR^7$, $R^7$ is —OMe, $R^8$ is methyl, n is 1 and $R^9$ is —$CH(OH)CH_3$.

In some aspects, $R^1$ is methyl, $R^2$ is hydrogen, $R^3$ is hydrogen, X is N, $R^5$ is hydrogen, Y is N, Z is $CR^7$, $R^7$ is —$N(CH_3)_2$, $R^8$ is methyl, n is 2 and $R^9$ is fluorine.

In some aspects, $R^1$ is methyl, $R^2$ is hydrogen, $R^3$ is hydrogen, X is N, $R^5$ is hydrogen, Y is N, Z is $CR^7$, $R^7$ is —OMe, $R^8$ is methyl, n is 1 and $R^9$ is $CH_2$.

In some aspects, $R^1$ is hydrogen, $R^2$ is hydrogen, $R^3$ is hydrogen, X is $CR^4$, $R^4$ is hydrogen, $R^5$ is hydrogen, Y is $CR^6$, $R^6$ is methyl, Z is $CR^7$, $R^7$ is hydrogen, $R^8$ is methyl, n is 2 and $R^9$ is fluorine.

In some aspects, $R^1$ is hydrogen, $R^2$ is hydrogen, $R^3$ is hydrogen, X is $CR^4$, $R^4$ is fluorine, $R^5$ is hydrogen. Y is $CR^6$, $R^6$ is hydrogen, Z is $CR^7$, $R^7$ is hydrogen, $R^8$ is —OMe, n is 1 and $R^9$ is cyclopropyl.

In some aspects, $R^1$ is methyl, $R^2$ is hydrogen, $R^3$ is hydrogen, X is N, $R^5$ is hydrogen, Y is N, Z is $CR^7$, $R^7$ is —$OCH_3$, $R^8$ is methyl, n is 1 and $R^9$ is —$CHF_2$.

In some aspects, $R^1$ is methyl, $R^2$ is hydrogen, $R^3$ is hydrogen, X is N, $R^5$ is hydrogen, Y is N, Z is $CR^7$, $R^7$ is —$N(CH_3)_2$, $R^8$ is methyl, n is 2 and $R^9$ is —OH.

In some aspects, $R^1$ is methyl, $R^2$ is hydrogen, $R^3$ is hydrogen, X is N, $R^5$ is hydrogen, Y is N, Z is $CR^7$, $R^7$ is —$OCHF_2$, $R^8$ is methyl, n is 2 and $R^9$ is —OH.

In some aspects, $R^1$ is —$OCH_3$, $R^2$ is hydrogen, $R^3$ is hydrogen, X is N, $R^5$ is hydrogen. Y is N, Z is $CR^7$, $R^7$ is —$OCH_3$, $R^8$ is methyl, n is 2 and $R^9$ is —OH.

In some aspects, $R^1$ is —$OCH_3$, $R^2$ is hydrogen, $R^3$ is hydrogen, X is N, $R^5$ is hydrogen, Y is N, Z is $CR^7$, $R^7$ is —$OCH_3$, $R^8$ is methyl, n is 1 and $R^9$ is —$CHF_2$.

In some aspects, $R^1$ is —$OCH_3$, $R^2$ is hydrogen, $R^3$ is hydrogen, X is N, $R^5$ is hydrogen, Y is N, Z is $CR^7$, $R^7$ is —OCH₃, R⁸ is methyl, n is 2 and R⁹ is —OH. In some aspects, R¹ is —OCH₃, R² is hydrogen, R³ is hydrogen, X is N, R⁵ is hydrogen, Y is N, Z is CR⁷, R⁷ is —N(CH₃)₂, R⁸ is methyl, n is 2 and R⁹ is F.

In some aspects, R1 is —OCH3, R2 is hydrogen, R3 is hydrogen, X is N, R5 is hydrogen, Y is N, Z is CR7, R7 is —N(CH3)2, R8 is methyl, n is 1 and R9 is —CHF2.

In some aspects, R¹ is —OCH₃, R² is hydrogen, R³ is hydrogen, X is N, R⁵ is hydrogen, Y is N, Z is CR⁷, R⁷ is —N(CH₃)₂, R⁸ is methyl, n is 2 and R⁹ is —OH.

In some aspects, R¹ is —OCH₃, R² is hydrogen, R³ is hydrogen, X is N, R⁵ is hydrogen, Y is N, Z is CR⁷, R⁷ is —OCHF₂, R⁸ is methyl, n is 2 and R⁹ is F.

In some aspects, R¹ is —OCH₃, R² is hydrogen, R³ is hydrogen, X is N, R⁵ is hydrogen, Y is N, Z is CR⁷, R⁷ is —OCHF₂, R⁸ is methyl, n is 1 and R⁹ is —CHF₂.

In some aspects, R¹ is —OCH₃, R² is hydrogen, R³ is hydrogen, X is N, R⁵ is hydrogen, Y is N, Z is CR⁷, R⁷ is —OCHF₂, R⁸ is methyl, n is 2 and R⁹ is —OH.

In some aspects, R¹ is —OCH₃, R² is hydrogen, R³ is hydrogen, X is N. R⁵ is hydrogen, Y is N, Z is CR⁷, R⁷ is —OCHF₂, R⁸ is methyl, n is 2 and R⁹ is F.

In some aspects, R¹ is methyl. R² is hydrogen, R³ is hydrogen, X is N, R⁵ is hydrogen, Y is CR⁶, R⁶ is methyl. Z is N. R⁸ is methyl, n is 2 and R⁹ is F.

In some aspects, R¹ is methyl, R² is hydrogen, R³ is hydrogen, X is N. R⁵ is hydrogen, Y is CR⁶, R⁶ is methyl, Z is N. R⁸ is methyl, n is 1 and R⁹ is CHF₂.

In some aspects, the compounds of formula (I) include the compounds in Table 1, or pharmaceutically acceptable salts thereof.

TABLE 1

| Compound No. | Compound | Mtb MIC (μM) |
|---|---|---|
| 1 | 1-(1-(2,6-difluorophenyl)ethyl)-N-(2-fluoroethyl)-1H-pyrrolo[3,2-b]pyridine-3-carboxamide | 12.5 |
| 2 | N-(Cyclopropylmethyl)-1-(5-fluoro-2-methoxybenzyl)-7-methyl-1H-pyrrolo[3,2-b]pyridine-3-carboxamide | 6.25 |
| 3 | N-(2-fluoroethyl)-1-((6-methoxy-5-methylpyrimidin-4-yl)methyl)-1H-pyrrolo[3,2-b]pyridine-3-carboxamide | 1.56 |
| 4 | N-(cyclopropylmethyl)-1-((6-methoxy-5-methylpyrimidin-4-yl)methyl)-1H-pyrrolo[3,2-b]pyridine-3-carboxamide | <0.781 |

TABLE 1-continued

| Compound No. | Compound | Mtb MIC (μM) |
|---|---|---|
| 5 | 1-(2,3-difluoro-6-methoxybenzyl)-N-(2-fluoroethyl)-1H-pyrrolo[3,2-b]pyridine-3-carboxamide | <0.66 |
| 6 | 1-((5-fluoro-2-methoxypyridin-3-yl)methyl)-N-(2-methoxyethyl)-1H-pyrrolo[3,2-b]pyridine-3-carboxamide | 1.3 |
| 7 | 1-((6-methoxy-5-methylpyrimidin-4-yl)methyl)-N-(2-methoxyethyl)-1H-pyrrolo[3,2-b]pyridine-3-carboxamide | <1.33 |
| 8 | N-(2-fluoroethyl)-1-((6-methoxy-5-methylpyrimidin-4-yl)methyl)-6-methyl-1H-pyrrolo[3,2-b]pyridine-3-carboxamide | <0.53 |
| 9 | N-(2-hydroxyethyl)-1-((6-methoxy-5-methylpyrimidin-4-yl)methyl)-1H-pyrrolo[3,2-b]pyridine-3-carboxamide | 13.9 |
| 10 | N-(cyclopropylmethyl)-1-((6-methoxy-5-methylpyrimidin-4-yl)methyl)-6-methyl-1H-pyrrolo[3,2-b]pyridine-3-carboxamide | 1.56 |

TABLE 1-continued

| Compound No. | Compound | Mtb MIC (µM) |
|---|---|---|
| 11 | 1-((6-methoxy-5-methylpyrimidin-4-yl)methyl)-N-(2-methoxyethyl)-6-methyl-1H-pyrrolo[3,2-b]pyridine-3-carboxamide | 0.781 |
| 12 | N-(2-fluoroethyl)-1-((3-methyl-4-(2,2,2-trifluoroethoxy)pyridin-2-yl)methyl)-1H-pyrrolo[3,2-b]pyridine-3-carboxamide | 6.25 |
| 13 | N-(2-fluoroethyl)-1-((2-methoxy-5-(trifluoromethyl)pyridin-3-yl)methyl)-1H-pyrrolo[3,2-b]pyridine-3-carboxamide | <0.53 |
| 14 | 1-((5-cyano-2-methoxypyridin-3-yl)methyl)-N-(2-fluoroethyl)-1H-pyrrolo[3,2-b]pyridine-3-carboxamide | 3.12 |
| 15 | 1-((5-fluoro-2-methoxypyridin-3-yl)methyl)-N-(2-fluoroethyl)-6-methyl-1H-pyrrolo[3,2-b]pyridine-3-carboxamide | 1.56 |
| 16 | (S)-N-(2-fluoropropyl)-1-((6-methoxy-5-methylpyrimidin-4-yl)methyl)-6-methyl-1H-pyrrolo[3,2-b]pyridine-3-carboxamide | 0.156 |

TABLE 1-continued

| Compound No. | Compound | Mtb MIC (μM) |
|---|---|---|
| 17 | N-(2-hydroxyethyl)-1-((6-methoxy-5-methylpyrimidin-4-yl)methyl)-6-methyl-1H-pyrrolo[3,2-b]pyridine-3-carboxamide | 1.56 |
| 18 | 1-((5-fluoro-2-methoxy-6-methylpyridin-3-yl)methyl)-N-(2-fluoroethyl)-1H-pyrrolo[3,2-b]pyridine-3-carboxamide | 0.781 |
| 19 | 6-fluoro-N-(2-fluoroethyl)-1-((6-methoxy-5-methylpyrimidin-4-yl)methyl)-1H-pyrrolo[3,2-b]pyridine-3-carboxamide | 6.25 |
| 20 | 6-bromo-N-(2-fluoroethyl)-1-((6-methoxy-5-methylpyrimidin-4-yl)methyl)-1H-pyrrolo[3,2-b]pyridine-3-carboxamide | 0.781 |
| 21 | N-(2-fluoroethyl)-6-methyl-1-((3-methyl-4-(2,2,2-trifluoroethoxy)pyridin-2-yl)methyl)-1H-pyrrolo[3,2-b]pyridine-3-carboxamide | 1.56 |
| 22 | (S)-N-(2-fluoropropyl)-1-((2-methoxy-5-(trifluoromethyl)pyridin-3-yl)methyl)-6-methyl-1H-pyrrolo[3,2-b]pyridine-3-carboxamide | <0.391 |

TABLE 1-continued

| Compound No. | Compound | Mtb MIC (μM) |
|---|---|---|
| 23 | 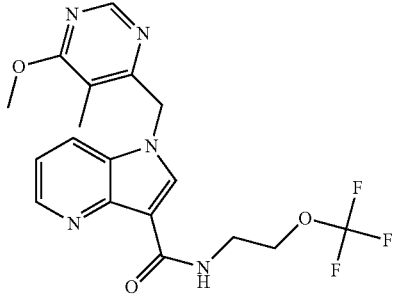 1-((6-methoxy-5-methylpyrimidin-4-yl)methyl)-N-(2-(trifluoromethoxy)ethyl)-1H-pyrrolo[3,2-b]pyridine-3-carboxamide | 3.12 |
| 24 | 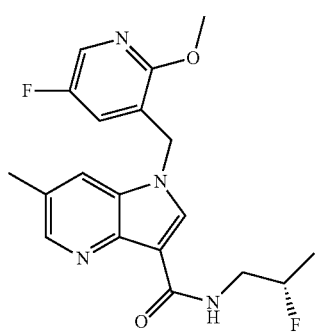 (S)-1-((5-fluoro-2-methoxypyridin-3-yl)methyl)-N-(2-fluoropropyl)-6-methyl-1H-pyrrolo[3,2-b]pyridine-3-carboxamide | <0.391 |
| 25 | 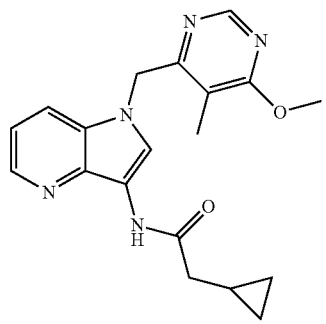 2-cyclopropyl-N-(1-((6-methoxy-5-methylpyrimidin-4-yl)methyl)-1H-pyrrolo[3,2-b]pyridin-3-yl)acetamide | 25 |
| 26 | 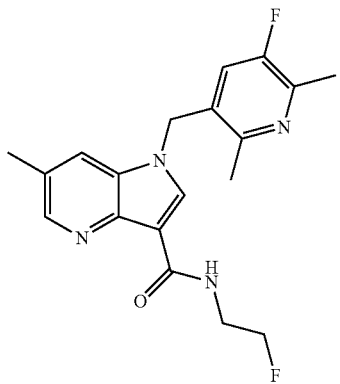 1-((5-fluoro-2,6-dimethylpyridin-3-yl)methyl)-N-(2-fluoroethyl)-6-methyl-1H-pyrrolo[3,2-b]pyridine-3-carboxamide | 3.12 |
| 27 | 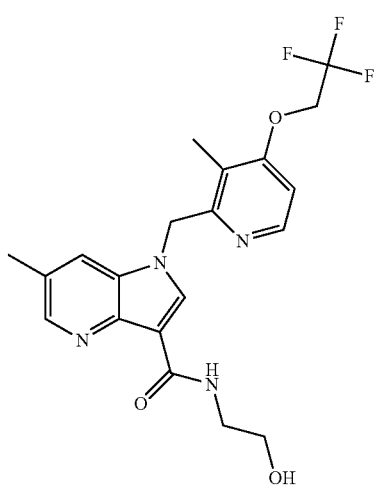 N-(2-hydroxyethyl)-6-methyl-1-((3-methyl-4-(2,2,2-trifluoroethoxy)pyridin-2-yl)methyl)-1H-pyrrolo[3,2-b]pyridine-3-carboxamide | 3.12 |
| 28 | 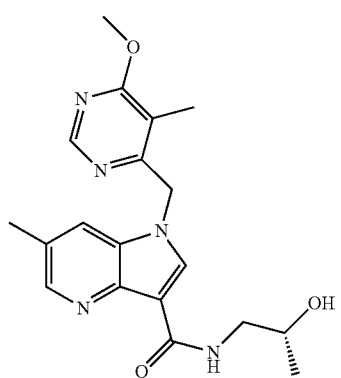 (R)-N-(2-hydroxypropyl)-1-((6-methoxy-5-methylpyrimidin-4-yl)methyl)-6-methyl-1H-pyrrolo[3,2-b]pyridine-3-carboxamide | 6.25 |

TABLE 1-continued

| Compound No. | Compound | Mtb MIC (μM) |
|---|---|---|
| 29 | 1-((6-(dimethylamino)-5-methyl-pyrimidin-4-yl)methyl)-N-(2-fluoroethyl)-6-methyl-1H-pyrrolo[3,2-b]pyridine-3-carboxamide | 1.56 |
| 30 | N-(2,2-difluoroethyl)-1-((6-methoxy-5-methylpyrimidin-4-yl)methyl)-6-methyl-1H-pyrrolo[3,2-b]pyridine-3-carboxamide | <0.391 |
| 31 | 1-(2,4-dimethylbenzyl)-N-(2-fluoroethyl)-1H-pyrrolo[3,2-b]pyridine-3-carboxamide | 1.56 |
| 32 | N-(cyclopropylmethyl)-1-(2-fluoro-6-methoxybenzyl)-1H-pyrrolo[3,2-b]pyridine-3-carboxamide | 1.56 |
| 33 | N-(2,2-difluoroethyl)-1-((6-methoxy-5-methylpyrimidin-4-yl)methyl)-6-methyl-1H-pyrrolo[3,2-b]pyridine-3-carboxamide | <0.39 |
| 34 | 1-((6-(dimethylamino)-5-methylpyrimidin-4-yl)methyl)-N-(2-hydroxyethyl)-6-methyl-1H-pyrrolo[3,2-b]pyridine-3-carboxamide | <0.39 |

TABLE 1-continued

| Compound No. | Compound | Mtb MIC (μM) |
|---|---|---|
| 35 | 1-((6-(difluoromethoxy)-5-methylpyrimidin-4-yl)methyl)-N-(2-hydroxyethyl)-6-methyl-1H-pyrrolo[3,2-b]pyridine-3-carboxamide | <0.39 |
| 36 | N-(2-fluoroethyl)-6-methoxy-1-((6-methoxy-5-methylpyrimidin-4-yl)methyl)-1H-pyrrolo[3,2-b]pyridine-3-carboxamide | <0.39 |
| 37 | N-(2,2-difluoroethyl)-6-methoxy-1-((6-methoxy-5-methylpyrimidin-4-yl)methyl)-1H-pyrrolo[3,2-b]pyridine-3-carboxamide | <0.39 |
| 38 | N-(2-hydroxyethyl)-6-methoxy-1-((6-methoxy-5-methylpyrimidin-4-yl)methyl)-1H-pyrrolo[3,2-b]pyridine-3-carboxamide | 0.78 |
| 39 | 1-((6-(dimethylamino)-5-methylpyrimidin-4-yl)methyl)-N-(2-fluoroethyl)-6-methoxy-1H-pyrrolo[3,2-b]pyridine-3-carboxamide | <0.39 |
| 40 | N-(2,2-difluoroethyl)-1-((6-(dimethylamino)-5-methylpyrimidin-4-yl)methyl)-6-methoxy-1H-pyrrolo[3,2-b]pyridine-3-carboxamide | <0.39 |

TABLE 1-continued

| Compound No. | Compound | Mtb MIC (µM) |
|---|---|---|
| 41 | 1-((6-(dimethylamino)-5-methylpyrimidin-4-yl)methyl)-N-(2-hydroxyethyl)-6-methoxy-1H-pyrrolo[3,2-b]pyridine-3-carboxamide | <0.39 |
| 42 | 1-((6-(difluoromethoxy)-5-methylpyrimidin-4-yl)methyl)-N-(2-fluoroethyl)-6-methoxy-1H-pyrrolo[3,2-b]pyridine-3-carboxamide | <0.39 |
| 43 | N-(2,2-difluoroethyl)-1-((6-(difluoromethoxy)-5-methylpyrimidin-4-yl)methyl)-6-methoxy-1H-pyrrolo[3,2-b]pyridine-3-carboxamide | <0.39 |
| 44 | 1-((6-(difluoromethoxy)-5-methylpyrimidin-4-yl)methyl)-N-(2-hydroxyethyl)-6-methoxy-1H-pyrrolo[3,2-b]pyridine-3-carboxamide | 0.78 |
| 45 | 1-((3,5-dimethylpyrazin-2-yl)methyl)-N-(2-fluoroethyl)-6-methyl-1H-pyrrolo[3,2-b]pyridine-3-carboxamide | <0.39 |
| 46 | N-(2,2-difluoroethyl)-1-((3,5-dimethylpyrazin-2-yl)methyl)-6-methyl-1H-pyrrolo[3,2-b]pyridine-3-carboxamide | <0.39 |

Pharmaceutical Compositions

In some aspects, the invention provides a pharmaceutical composition comprising a compound of formula (I), or a pharmaceutically acceptable salt thereof, and a pharmaceutically acceptable diluent or carrier.

The language "pharmaceutically acceptable" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Methods of Use

In some aspects, the invention provides a compound of formula (I) or a pharmaceutically acceptable salt thereof, for use in the treatment of tuberculosis or a *Mycobacterium* infection.

In some aspects, the invention provides a compound of formula (I) in the manufacture of a medicament for use in the treatment of tuberculosis or a *Mycobacterium* infection.

In some aspects, the invention provides a method of treating tuberculosis or a *Mycobacterium* infection comprising administering to a subject in need thereof a therapeutically effective amount of a compound of formula (I) or a pharmaceutically acceptable salt thereof.

The language "therapeutically effective amount" includes an amount of the co-crystals described herein that will elicit the biological or medical response of a subject, for example, the reduction or inhibition of enzyme or protein activity related to a *Mycobacterium* infection or tuberculosis, amelioration of symptoms of a *Mycobacterium* infection or tuberculosis, or the slowing or delaying of progression of a *Mycobacterium* infection or tuberculosis. In some embodiments, the language "therapeutically effective amount" includes the amount of a co-crystal described herein, that when administered to a subject, is effective to at least partially alleviate, inhibit, and/or ameliorate a *Mycobacterium* infection or tuberculosis, and/or reduce or inhibit the bacterial growth, replication or bacterial load of *Mycobacterium* in a subject.

The term "subject" includes warm blooded mammals, for example, primates, cows, sheep, dogs, cats, rabbits, rats, voles, seals and mice. In some embodiments, the subject is a primate, for example, a human. In some embodiments, the subject is suffering from a *Mycobacterium* infection or tuberculosis. In some embodiments, the subject is in need of treatment (e.g., the subject would benefit biologically or medically from treatment).

The language "inhibit," "inhibition" or "inhibiting" includes a decrease in the baseline activity of a biological activity or process.

The language "treat," "treating" and "treatment" includes the reduction or inhibition of enzyme or protein activity related to a *Mycobacterium* infection or tuberculosis in a subject, amelioration of one or more symptoms of a *Mycobacterium* infection or tuberculosis in a subject, or the slowing or delaying of progression of a *Mycobacterium* infection or tuberculosis in a subject. The language "treat," "treating" and "treatment" also includes the reduction or inhibition of the bacterial growth, replication or a reduction or inhibition of the bacterial load of *Mycobacterium* in a subject.

The language "*Mycobacterium* infection" includes infections caused by one or more of the species of the *Mycobacterium tuberculosis* complex, e.g., *Mycobacterium tuberculosis, Mycobacterium bovis, Mycobacterium africanum, Mycobacterium canetti, Mycobacterium caprae, Mycobacterium microti* or *Mycobacterium pinnipedii*. In some embodiments, the *Mycobacterium* infection is a *Mycobacterium tuberculosis* infection.

The term "tuberculosis" refers to the disease caused by an infection in a subject of one or more species of the *Mycobacterium tuberculosis* complex. The term "tuberculosis" includes latent tuberculosis (LTBI), non-drug resistant tuberculosis, multiple drug resistant tuberculosis (MDR-TB) and extensively drug resistant tuberculosis (XRD-TB). The language "latent tuberculosis" includes an infection of a subject caused by one or more species of *Mycobacterium tuberculosis* complex but where the subject does not necessarily exhibit symptoms a tuberculosis disease. The language "non-drug resistant tuberculosis" includes tuberculosis caused by an infection by one or more species of the *Mycobacterium* tuberculosis complex that exhibits no antibacterial resistance to standard tuberculosis therapy. The language "multiple drug resistant tuberculosis (MDR-TB)" includes tuberculosis caused by an infection by of one or more species of the *Mycobacterium tuberculosis* complex that is resistant to rifampicin and isoniazid. The language "extensively drug resistant tuberculosis (XRD-TB)" includes tuberculosis caused by an infection by one or more species of the *Mycobacterium tuberculosis* complex that is resistant to rifampicin and isoniazid, as well as any member of the quinolone family, and is also resistant to at least one of kanamycin, capreomycin and amikacin. In some embodiments, the tuberculosis infection is acute. In some embodiments, the tuberculosis infection is chronic.

In some aspects, the invention provides a compound of formula (I) or a pharmaceutically acceptable salt thereof, for inhibiting DprE1.

In some aspects, the invention provides a compound of formula (I) in the manufacture of a medicament for use in inhibiting DprE1.

In some aspects, the invention provides a method of inhibiting DprE1 comprising contacting a cell with a therapeutically effective amount of a compound of formula (I) or a pharmaceutically acceptable salt thereof.

Combinations

The compounds described herein may be applied as a sole therapy or may involve one or more other substances and/or treatments. Such co-treatment may be achieved by way of the simultaneous, sequential or separate administration of the individual components of the treatment. Where the administration is sequential or separate, the delay in administering the second component should not be such as to lose the beneficial effect of the combination. Suitable classes and substances include one or more antibacterial agents useful in the treatment of *Mycobacterium* infections and/or tuberculosis, such as, for example, rifampicin, isoniazid, pyrizinamide, ethambutol, quinolones (e.g., ciprofloxacin, levofloxacin, moxifloxacin and gatifloxacin), aminoglycosides (e.g., streptomycin, kanamycin, and amikacin), polypeptides (e.g., capreomycin, viomycin and enviomycin), rifabutin, clarithromycin, linezolid, thioacetazone, thioridazine, arginine, vitamin D and R207910.

EXAMPLES

All anhydrous solvents, reagent grade solvents for chromatography and starting materials were purchased from either Sigma Aldrich Chemical Co. or Fisher Scientific. Water was distilled and purified through a Milli-Q water system (Millipore Corp. Bedford, Mass.). General methods of purification of compounds involved the use of silica cartridges purchased from Grace Purification systems. The reactions were monitored by TLC on precoated Merck 60 F254 silica gel plates and visualized using UV light (254 nm). All compounds were analyzed for purity by HPLC and characterized by $^1$H NMR using Bruker 300 MHz NMR and/or Bruker 400 MHz NMR spectrometers. Chemical shifts are reported in ppm (δ) relative to the residual solvent peak in the corresponding spectra; chloroform 67.26, methanol 63.31, DMSO-$d_6$ δ 3.33 and coupling constants (J) are reported in hertz (Hz) (where s=singlet, bs=broad singlet, d=doublet, dd=double doublet, bd=broad doublet, ddd=double doublet of doublet, t=triplet, tt—triple triplet, q=quartet, m=multiplet) and analyzed using ACD NMR data processing software. Mass spectra values are reported as m/z. All reactions were conducted under Nitrogen unless otherwise noted. Solvents were removed in vacuo on a rotary evaporator.

Abbreviations: NMP=N-methyl Pyrrolidine; HCl=hydrochloric acid; DMF=N,N-imethylformamide; NaH=sodium hydride. EI=electrospray ionization; HRMS=high resolution mass spectrometry.

FIG. 6 shows Synthetic Scheme 1 for the synthesis of Intermediates 3-9.

Intermediate 3: To a stirred suspension of NaH (60%) in dry DMF, diethyl malonate was added drop wise over a period of 30 min. To this mixture substituted 2-chloro-3-nitropyridine was added portion wise over a period of 1 h and stirred the contents at r.t for 90 min. The contents were heated to 80° C. over a period of 30 min and maintained for 1 h. DMF was evaporated from the reaction mixture under vacuum and the residue was diluted with water. The reaction mixture pH was adjusted to 5-6 range and extracted with ethyl acetate. The organic layer was washed with water, brine, dried over anhydrous $Na_2SO_4$ and concentrated by rotary evaporation to get an orange oily liquid. The compound was used as such in next step without further purification.

Intermediate 4: To a stirred solution of intermediate 3 in DMSO:$H_2O$ was added LiCl and the reaction mixture was stirred at 80° C. for 16 h. Then the reaction mixture was poured in to water and extracted with ethyl acetate. The combine organic layer was washed with water, brine, dried over sodium sulfate, and concentrated at reduced pressure. The crude product was purified by silica gel column chromatography using ethyl acetate in hexane to afford intermediate 4.

Intermediate 5: To a stirred solution of intermediate 4 in DMF, was added DMF-DMA and the reaction mixture was stirred at 80° C. for 16 h. After completion of reaction the reaction mixture was poured in to ice-water and extracted with ethyl acetate. The combined organic layer was washed with water, brine, dried over sodium sulfate, and concentrated at reduced pressure to yield intermediate 5. The crude material was taken for next step without purification.

Intermediate 6: To the stirred solution of intermediate 5 in acetic acid was added Fe-powder at once and the mixture was stirred at 60° C. for 2 h. Then the reaction mixture was diluted with methanol and filter through celite. The filtrate was concentrated under reduced pressure. The crude product was purified by silica gel column chromatography using ethyl acetate to afford intermediate 6 as a solid.

Intermediate 7: To a stirred solution of intermediate 6 and $K_2CO_3$ in DMF was added aryl halide and the reaction mixture was stirred at RT for 16 h. The resulting mixture was poured in to water and extracted with dichloromethane. The combined organic layer was washed with water, brine, dried over sodium sulfate, and concentrated at reduced pressure to yield intermediate 7 as a solid or liquid.

OR

Intermediate 6 and $K_2CO_3$ was taken in dry DMF under nitrogen atmosphere. To this aryl halide was added. The resulting reaction was stirred at 80° C. for 3 h. DMF was evaporated to dryness, diluted with water and extracted with DCM. Purification was done on combiflash system to get intermediate 7 as a solid or liquid.

OR

Intermediate 6 was dissolved in DMF under nitrogen atmosphere. To this at 0° C. NaH was added. After 5 min aryl halide was added. The resulting reaction was stirred at it for 6 h. Reaction was poured on ice water, added ethyl acetate. Organic layer was separated and washed with brine and concentrated. Purification was done on combiflash system to obtain intermediate 7 as a solid or liquid.

Intermediate 8: To a solution of intermediate 7 in ethanol, was added lithium hydroxide in water. The reaction mixture was stirred for 5 h at RT. The solvent was evaporated under the reduced pressure to yield intermediate 8 as a off-white solid.

OR

To a solution of intermediate 7 in methanol was added lithium hydroxide in water. The reaction mixture was stirred at 60° C. for 3 h. The solvent was evaporated under the reduced pressure, nutralized with acetic acid to yield intermediate 8 as a off-white solid.

FIG. 7 shows Synthetic Scheme 2 for the synthesis of Intermediates 11-15.

Intermediate 11: To a solution of 2-chloro-5-(trifluoro ethyl)pyridine (5 g, 27.60 mmol) in methanol was added sodium methoxide (2.98 g, 55.20 mmol) at 0° C. The reaction mixture was stirred for 6 h at RT. Then the solvent was removed under vacuum. The resulting mixture was poured into water (100 mL) added water extracted with ethyl acetate (2×50 mL). The combined organic layer was washed with water, brine, dried over sodium sulfate, and concentrated at reduced pressure to yield 2-methoxy-5-(trifluoromethyl)pyridine (11) as a pale yellow liquid (4 g, 82.1%).

Intermediate 12: To a stirred solution of 2-methoxy 5-(trifluoromethyl) pyridine (4 g, 22.58 mmol) was dissolved in acetonitrile (50 ml) was added NBS (6 g, 33.87 mmol) portion wise at 0° C. The reaction mixture was stirred for overnight at RT. The solvent was removed under vacuum, quenched with water (100 mL) and extracted with ethyl acetate. The combined organic layer was washed with water, brine, dried over sodium sulfate, and concentrated at reduced pressure to yield 3-bromo-2-methoxy-5-(trifluoromethyl)pyridine (12) as a pale yellow liquid (2 g, 34.7%).

Intermediate 13: To a stirred solution of 3-bromo-2-methoxy-5-(trifluoromethyl)pyridine (23) (1.2 g, 4.68 mmol) dissolved in mixture of methanol (10 ml)/toluene (10 was added triethylamine (1 ml, 7.65 mmol), [1,1'-Bis(diphenylphosphino)ferrocene]palladium(II) dichloride (70 mg, 0.102 mmol). The reaction mixture was carbonylated under CO [5 kg] at 80° C. for 12 h. Then the solvent was filtered through celite and solvent was concentrated on vacuum, get crude. The crude compound was purified by using silica gel chromatography eluting 30% ethyl acetate in hexaen to afford methyl 2-methoxy-5-(trifluoromethyl)nicotinate (13) as a liquid (0.5 g, 45.4%).

Intermediate 14: To a solution of methyl 2-methoxy-5-(trifluoromethyl)nicotinate (13) (0.5 g, 2.12 mmol) dissolved in DCM was added DIBAL-H (6.38 ml, 1M in Toluene) at 0° C. The reaction mixture was stirred for 2 h at RT. Then the reaction mixture was quenched with saturated $NH_4Cl$ solution and extracted with ethyl acetate (2×25 mL). The combined organic layer was washed with water, brine, dried over sodium sulfate, and concentrated at reduced pressure to yield (2-methoxy-5-(trifluoromethyl)pyridin-3-yl)methanol (14) as a pale yellow liquid (0.4 g, 90%).

Intermediate 15: To a solution of 2-methoxy-5-(trifluoromethyl)pyridin-3-yl)methanol (14) (0.4 g, 1.93 mmol) dissolved in DCM was added thionyl chloride (0.38 ml, 3.86 mmol). The reaction mixture was stirred for 2 h at RT. The solvent was evaporated under the reduced pressure and the reaction mixture was poured in to water (50 mL) and extracted with DCM (2×50 mL). The combined organic layer was washed with water, brine, dried over sodium sulfate, and concentrated at reduced pressure to yield 3-(chloromethyl)-2-methoxy-5-(trifluoromethyl)pyridine (15) as a liquid. (Yield 0.3 g, 69.76%)

FIG. 8 shows Synthetic Scheme 3 for the synthesis of Intermediates 17-21.

Intermediate 17: To a solution of 2,6-dichloro-5-fluoronicotinic acid (16) (5 g, 23.8 mmol) in methanol (50 ml) was added thionyl chloride in dropwise (5.66 g, 47.62 mmol) at 0° C. and 2 drops of DMF [vigourous bubbling was observed]. The mixture was stirred at room temperature for 3 h. To this methanol was added and stirred the reaction mixture for 2 h at RT. The reaction mixture is concentrated under reduced pressure to and the mixture was poured in to ice cold water (20 mL) and extracted with dichloromethane (2×50 mL). The combined organic layer was washed with water, brine and solvent was evaporated under reduced pressure to yield methyl 2,6-dichloro-5-fluoronicotinate (17) (5 g, 93.8%).

Intermediate 18: A mixture of methyl 2,6-dichloro-5-fluoronicotinate (17) (3.5 g 15.62 mmol), trimethylboroxin (1.96 g, 15.62 mmol), 1,1'-Bis(diphenylphosphino)ferrocene-palladium(II)dichloride dichloromethane (1.276 g, 1.562 mmol) and cesium carbonate 15.27 g, 46.86 mmol) was heated at 110° C. overnight. The mixture is cooled to room temperature, diluted with water, and extracted with EtOAc. The combined organic phase is washed with water followed by brine, then dried over anhydrous sodium sulfate and concentrated under reduced pressure. The residue is purified by flash silica gel chromatography using a gradient of 0-30% EtOAc/heptanes to provide methyl 2-chloro-5-fluoro-6-methylnicotinate (18) 0.8 g as a colorless solid (0.8 g 25%).

Intermediate 19: To a stirred solution of methyl 2-chloro-5-fluoro-6-methylnicotinate (18) (0.8 g, 3.92 mmol,) in THF (35 mL) was added sodium methanolate (0.42 g, 7.85 mmol) at 0° C. The mixture was stirred at 60° C. for 6 hours and cooled to room temperature. Then the mixture was poured into water and extracted with dichloromethane (2×50 mL). The combined organic layer was washed with water, brine and solvent was evaporated under reduced pressure. The residue was purified by column chromatography on silica gel eluting with 10% ethyl acetate in hexane to give methyl 5-fluoro-2-methoxy-6-methylnicotinate (19) (250 mg, 32%) as a white solid.

Intermediate 20: To a solution of methyl 5-fluoro-2-methoxy-6-methylnicotinate (19) (0.25 g, mmol) in MDC was added DIBAL-H in dropwise (2.5 ml, 1M in Toluene) at 0° C. The reaction mixture was stirred for 2 h at RT. Reaction was quenched with saturated ammonium chloride solution and extracted with DCM (2×50 ml). The combined organic layer was washed with water, brine and solvent was evaporated under reduced pressure to yield (5-fluoro-2-methoxy-6-methylpyridin-3-yl)methanol (20) as a liquid (0.2 g 90%).

Intermediate 21: To a solution of (5-fluoro-2-methoxy-6-methylpyridin-3-yl)methanol (20) (0.2 g, 1.16 mmol) in DCM was added thionyl chloride (0.278 g, 2.33 mmol). The reaction mixture was stirred for 2 h at RT. The solvent was evaporated under the reduced pressure and the reaction mixture was poured in to water (50 mL) and extracted with DCM (2×50 mL). The combined organic layer was washed with water, brine, dried over sodium sulfate, and concentrated at reduced pressure to yield to afford 3-(chloromethyl)-5-fluoro-2-methoxy-6-methylpyridine (21) as a pale yellow liquid (0.2 g) 90%.

FIG. 9 shows Synthetic Scheme 4, for the synthesis of Intermediates 23-25.

Intermediate 23: To a solution of ethyl 6-chloro-5-methylpyrimidine-4-carboxylate (35) (0.9 g, 4.48 mmol) dissolved in dioxane (20 ml) were added dimethyl amine in THF (1M. 22.43 ml, 22.43 mmol) and diisopropyl ethylamine (3 ml, 22.43 mmol). The reaction mixture was heated to 80° C. for 16 h. Then the mixture is cooled to room temperature, diluted with water, and extracted with EtOAc (2×50 mL). The combined organic layer was washed with water, brine, dried over sodium sulfate, and concentrated at reduced pressure to yield ethyl 6-(dimethylamino)-5-methylpyrimidine-4-carboxylate (23) as a light yellow liquid; 0.4 g (43%).

Intermediate 24: To a stirred solution of ethyl 6-(dimethylamino)-5-methylpyrimidine-4-carboxylate (23) (0.4 g, 1.91 mmol) in MeOH (10 mL) was added in portionwise $NaBH_4$ (0.14 g, 3.82 mmol) at 0° C. and the mixture was stirred for 16 h at RT. The solvent was evaporated under the reduced pressure and the reaction mixture was poured in to water (20 mL) and extracted with ethyl acetate (3×30 mL). The combined organic layer was washed with water, brine, dried over sodium sulfate, and concentrated at reduced pressure to yield (6-(dimethylamino)-5-methylpyrimidin-4-yl)methanol (24); 0.1 g, (31.3%).

Intermediate 25: To a solution of (6-(dimethylamino)-5-methylpyrimidin-4-yl)methanol (24) (0.1 g, 0.60 mmol) in DCM was added thionyl chloride (0.14 g, 1.1961 mmol). The reaction mixture was stirred for 4 h at RT. The solvent was removed under reduced pressure to afford 6-(Chloromethyl)-N,N,5-trimethylpyrimidin-4-amine (25) as a white solid; 0.1 g 90.9%).

FIG. 10 shows Synthetic Scheme 5, for the synthesis of intermediates 27-30.

Intermediate 27: 2-Chloro-6-trifluoro methylpyridine (1.0 g, 5.5 mmol) in THF solution (10 ml) was added slowly to a cold (at −78° C.) solution of LDA (4.58 ml, 8.2 mmol) in dry THF (15 ml). The resulting mixture was stirred for 4 h at −78 OC, before the addition of methyl iodide (0.705 ml, 0.0082 mol) in THF (4 ml). Stirring was continued for 4 h at −75° C., before quenching with water (10 ml) at the same temperature, and further addition of water (15 ml) at 0° C. after 2 h. The crude product was extracted with ethyl acetate, washed with brine solution, and the combined organic layer was dried over $Na_2SO_4$, and solvent removed in vacuum to afford a crude solid, which was purified by flash column chromatography on silica (ethyl acetate/petrpleum ether (0-10%) to afford 27 as a off-white solid; (0.6 g, 33%).

Intermediate 28: In a tiny clave apparatus, 2-chloro-3-methyl-6-(trifluoro methyl)pyridine (27) (0.5 g, 2.5 mmol) was dissolved in MeOH (10 ml) and added TEA (0.5 ml, 3.7 mmol) which was degassed for 15 minutes with nitrogen before adding Pd(dppf)Cl$_2$.DCM complex (0.061 g, 0.075 mmol). Tiny clave was filled with CO gas (75 Psi, 5 kg) and heated at 75° C. for 16 h. The mixture was filtered through celite and washed with methanol. Combined filtrate was concentrated and the crude was purified flash column chromatography on silica (ethyl acetate/hexane (0-10%) to afford methyl 3-methyl-6-(trifluoromethyl)picolinate (28): off-white solid; (280 mg, 49.9%).

Intermediate 29: To a solution of methyl 3-methyl-6-(trifluoro methyl)picolinate (0.28 g) in DCM (10 ml) at −78° C. was added DIBAL-H (1.92 ml, 1.91 mmol) under nitrogen. The reaction mixture was allowed to reach rt and stirred for 1 h. The RM was quenched with ammonium chloride solution and extracted with ethyl acetate (3 30 mL). The combined organic layer was washed with brine, dried over Na$_2$SO$_4$ and concentrated to give 3-methyl-6-(trifluoromethyl)pyridin-2-yl)methanol (29). The crude alcohol was taken directly for next step (180 mg, 72%).

Intermediate 30: To a solution of (3-methyl-6-(trifluoromethyl)pyridin-2-yl)methanol (29) (0.18 g, 0.94 mmol) in DCM (5 ml) was added thionyl chloride (0.112 g, 0.95 mmol) and stirred at rt for 2 h. After completion of the reaction, mixture was concentrated and washed with hexane to afford 2-(chloromethyl)-3-methyl-6-(trifluoromethyl)pyridine (30). The crude solid was taken directly for the next step (180 mg, 91.8%).

FIG. 11 shows Synthetic Scheme 6, for the synthesis of Intermediates 32-33.

Intermediate 32: To a stirred solution of 1-(2,4-dimethylphenyl)ethan-1-one (1.0 g, 0.0067 mol) in MeOH (10 ml) was added NaBH$_4$ (0.77 g, 0.0.020 mol) portion-wise at 0° C. The resultant mixture was stirred at RT for 1 h. After completion of the reaction, the mixture was quenched with ice cold water (2.5 ml) and solvent was concentrated under reduced pressure. The reaction mixture was diluted with water and extracted with EtOAc (3×15 ml). The combined organic layer was washed with water, brine, dried over sodium sulfate, and concentrated at reduced pressure. The crude mixture was just passed through a pad of silica gel and washed with 3:1 hexanes:EtOAc to afford (0.9 g, 88.8%) to give the title compound 32 as a white solid.

Intermediate 33: To a stirred solution of 1-(2,4-dimethylphenyl)ethan-1-ol (32) (0.9 g, 0.006 mol) in CH$_2$Cl$_2$ (10 ml) was added phosphorus tribromide (0.85 ml, 0.009 mol) at room temperature. Stirring was continued for another 2 h at the same temperature. The mixture was quenched with water, and was extracted with CH$_2$Cl$_2$ (3×15 ml). The combined organic layer was washed with water, brine, dried over sodium sulfate, and concentrated at reduced pressure to give the title product (33) as a light orange solid (900 mg, 70.8% yield).

FIG. 12 shows Synthetic Scheme 7, for the synthesis of Intermediates 35-37.

Intermediate 35: A solution of 2,5-dibromo-3-methylpyridine (1) 3 g, 12.1 mmol) in methanol (20 ml) was added sodium methoxide (2M, 20 mL) and refluxed at 100° C. for 2 h. The reaction mixture was poured on ice water and neutralized with aqueous hydrochloric acid (1M) and extracted with dichloromethane(2×15 ml). The combined organic layer was washed with water, brine, dried over sodium sulfate, and concentrated at reduced pressure to give 5-Bromo-2-methoxy-3-methyl-pyridine (35), which was used without further purification (1.9 g, 77.8%).

Intermediate 36: To a solution of 5-bromo-2-methoxy-3-methyl-pyridine (1.0 g, 5.0 mmol) in DMF (10 ml) was added CuCN (0.534 g, 6.0 mmol) and the resulting mixture is heated at reflux for 28 h. After cooling to room temperature the mixture is diluted with EtOAc and washed with 10% ammonia solution followed by water and brine solution. The organic layer was separated, dried over MgSO$_4$ and evaporated under reduced pressure. The residue was purified by flash chromatography (5% EtOAc/Hexane) to give 5-cyano-2-methoxy-3-methyl-pyridine (36) (0.68 g, 93%).

Intermediate 37: To a solution of methyl 5-cyano-2-methoxy-3-methyl-pyridine (36) (0.25 g, 1.7 mmol) in CCl$_4$ (10 mL) was added N-bromosuccinimide (346 mg, 1.7 mmol) and 2',2-azobisisobutyronitrile (13.0 mg, 0.085 mmol). The reaction mixture was stirred at 80° C. for 1 h. The reaction mixture was filtered and the filtrate was concentrated to afford 5-(bromomethyl)-6-methoxy nicotinonitrile (37) as a yellow solid; (180 mg, 46.9%).

FIG. 13 shows Synthetic Scheme 8, for the synthesis of Intermediates 39-44.

Intermediate 39: To a solution of 38 (300 g, 2.94 mol) and ethyl propionate (429.4 g, 2.94 mol) in 1.8 L of anhydrous EtOH was added NaOEt (300 g, 4.41 mol) at room temperature. The mixture was stirred overnight. After cooling, the mixture was adjusted to pH=7 with 6N HCl. The mixture was concentrated in vacuum. The residue was diluted with water, and then extracted with EtOAc. The combined EtOAc layers were dried over Na$_2$SO$_4$ and concentrated in vacuo to furnish the product 39 (400 g, 67%) as a red liquid without further purification for the next step. $^1$H NMR: (400 MHz, CDCl$_3$) δ ppm 4.103-4.386 (m, 5H); 1.246-1.439 (m, 9H).

Intermediate 40: A mixture of 39 (300 g, 1.485 mol), formimidamide acetate (225 g, 2.12 mol) and NaOEt (160 g, 2.36 mol) in EtOH (2000 mL) was heated to reflux for 12 hours. After cooling, the mixture was adjusted to pH=7 with 6N HCl. The mixture was concentrated in vacuum. The residue was diluted with water, and then extracted with DCM. The combined DCM layers were washed with water, brine and concentrated in vacuo. The crude product was purified by chromatography on silica gel (PE: EtOAc=1:1-pure EtOAc) to afford the product as a white solid (80 g, 30% yield). ES+MS m/z: 183.0 (M+1). $^1$H NMR: (400 MHz, CDCl$_3$) δ ppm 8.126 (s, 1H); 4.345-4.399 (m, 2H); 2.242 (s, 3H); 1.337-1.373 (t, 3H).

Intermediate 41: A solution of 40 (80 g, 0.44 mol) in POCl$_3$ (800 g) was heated to reflux for 4 hours. After cooling, the excess POCl$_3$ was removed under reduced pressure to give 41 (88 g crude, 100% yield) as black oil. ES+MS m/z: 201.0 (M+1). $^1$H NMR: (400 MHz, CDCl$_3$) δ ppm 8.954 (s, 1H); 4.492-4.545 (m, 2H); 2.591 (s, 3H); 1.454-1.490 (t, 3H).

Intermediate 42: To a solution of 41 (88 g, 0.4 mol) in CH$_3$OH (1 L) was added CH$_3$ONa (40 g. 0.74 mol) at room temperature and the mixture was stirred at room temperature overnight. The mixture was adjusted to pH=7 with 6N HCl. The mixture was concentrated in vacuum. The residue was diluted with water, and then extracted with EtOAc. The combined EtOAc layers were dried over anhydrous Na$_2$SO$_4$ and concentrated in vacuum. The crude product was purified by chromatography on silica gel (PE: EtOAc=5:1) to afford 42 (10 g, 14% yield) as a yellow oil. ES+MS m/z: 197.0 (M+1). $^1$H NMR: (400 MHz, CDCl$_3$) δ ppm 8.626 (s, 1 H), 4.357-4.410 (m, 2 H), 3.969 (s. 3 H), 2.279 (s, 3 H), 1.344-1.380 (t, 3 H).

Intermediate 43: To solution of 42 (10 g, 0.057 mol) in CH₃OH (100 mL) was added NaBH₄ (10 g, 0.29 mol) at 0° C. and the resulting reaction was allowed warm to room temperature and stirred for 2 h. The mixture was concentrated in vacuum and partitioned between water and EtOAc. The water layer was extracted with EtOAc. The combined EtOAc layers were dried over Na₂SO₄, filtered and concentrated in vacuum to afford 43 (7.5 g, 85% yield) as a white solid. ES+MS m/z: 155.0 (M+1). ¹H NMR: (400 MHz, CDCl₃) δ ppm 8.629 (s, 1 H), 4.641 (s, 2 H), 4.007 (s, 3 H), 2.028 (s, 3 H).

Intermediate 44: To solution of 43 (7.5 g, 48.7 mmol) in DCM (150 mL) was added SOCl₂ (75 g, 0.64 mol) at 0° C. The resulting reaction was allowed warm to room temperature and stirred for 2 h. TLC showed the starting material was consumed. The mixture was concentrated in vacuum to provide 44 (8.3 g, 99% yield) as a yellow solid._ES+MS m/z: 173.0 (M+1). ¹H NMR: (400 MHz, CDCl₃) δ ppm 8.877 (s, 1 H), 4.992 (s, 2 H), 4.207 (s, 3 H), 2.317 (s, 3 H).

FIG. 14 shows Synthetic Scheme 9, for the synthesis of Intermediates 41-47.

Intermediate 41: A solution of ethyl 6-hydroxy-5-methylpyrimidine-4-carboxylate 40 (100 g, 549 mmol) in POCl₃ (1000 ml) was heated to reflux for 5 h at 100° C. in sealed tube. After cooling to RT, the excess POCl₃ was removed under reduced pressure, then quenched with ice water and extracted with EtOAc. The combined organic phase is washed with water, brine and concentrated under reduced pressure to afford ethyl 6-chloro-5-methylpyrimidine-4-carboxylate 41 as a black liquid. Yield: 80 (72%). This material was used as such for next step without purification.

Intermediate 45: To a solution of ethyl 6-chloro-5-methylpyrimidine-4-carboxylate (41) (80 g, 398.0 mmol) dissolved in dioxane (800 ml) were added dimethyl amine in THF (2M, 600 ml, 1196.0 mmol) and diisopropyl ethylamine (330 ml, 1990.0 mmol). The reaction mixture was heated to 80° C. for 16 h. Then the mixture is cooled to room temperature, diluted with water, and extracted with EtOAc (2×50 mL). The combined organic layer was washed with water, brine, dried over sodium sulfate, and concentrated at reduced pressure to yield ethyl 6-(dimethylamino)-5-methylpyrimidine-4-carboxylate (45) as a light yellow liquid; yield: 60 g (72%).

Intermediate 46: To a stirred solution of ethyl 6-(dimethylamino)-5-methylpyrimidine-4-carboxylate (45) (60.0 g, 287.0 mmol) in EtOH (600 mL) was added in portionwise NaBH₄ (21.82 g, 574.0 mmol) at 0° C. and the mixture was stirred for 16 h at RT. The solvent was evaporated under the reduced pressure and the reaction mixture was poured in to water (200 mL) and extracted with ethyl acetate (3×100 mL). The combined organic layer was washed with water, brine, dried over sodium sulfate and concentrated at reduced pressure to yield (6-(dimethylamino)-5-methylpyrimidin-4-yl) methanol (46); 47 g, (97%).

Intermediate 47: To a solution of (6-(dimethylamino)-5-methylpyrimidin-4-yl)methanol (46) (40 g, 239 mmol) in DCM was added thionyl chloride (35 ml, 478 mmol). The reaction mixture was stirred for 4 h at RT. The solvent was removed under reduced pressure to afford 6-(Chloromethyl)-N,N,5-trimethylpyrimidin-4-amine (47) as a brown solid; Yield: 40 g (90.9%); NMR (400 MHz, DMSO-d6) δ=8.69 (s, 1H), 4.86 (s, 2H), 3.27 (s, 6H), 2.35 (s, 3H).

FIG. 15 shows Synthetic Scheme 10, for the synthesis of Intermediates 48a and 48b-50.

Intermediate 48b: In a round bottom flask (5 litre) was taken Ethyl 6-hydroxy-5-methylpyrimidine-4-carboxylate 40 (85 g, 466 mmol), chlorodifluoroacetic acid sodium salt (106.7 g, 699 mmol), sodium carbonate (98.9 g, 933 mmol), acetonitrile (1500 ml) and DMF (425 ml). The reaction mixture was heated to 90° C. for 16 h. The Progress of the reaction was monitored by LCMS. The reaction mixture was cooled to room temperature and then neutralized with saturated ammonium chloride. The solvent was removed under vacuum and extracted with ethyl acetate. The combined organic layer was washed with water, brine and concentrated under reduced pressure. The crude compound was purified through silica gel chromatography eluting (3-4% ethyl acetate) to afford ethyl 6-(difluoromethoxy)-5-methylpyrimidine-4-carboxylate 48b as a pale yellow liquid. Yield: 14 g (13%).

Intermediate 49: To a stirred solution of 6-(difluoromethoxy)-5-methylpyrimidine-4-carboxylate 48b (14 g, 60.30 mmol) in ethanol (200 mL), NaBH₄ (4.58 g, 120.59 mmol) was added at 0° C. and the mixture was stirred for 16 h at RT. Then the solvent was evaporated under the reduced pressure and the reaction mixture was poured in to water and extracted with ethyl acetate. The organic layer was washed with water brine and concentrated under reduced pressure to afford (6-(difluoromethoxy)-5-methylpyrimidin-4-yl) methanol 39 as a yellow solid. Yield: 8.4 g (73.3%).

Intermediate 50: To a solution of (6-(difluoromethoxy)-5-methylpyrimidin-4-yl)methanol 49 (15 g, 78.94 mmol) dissolved in DCM (150 ml) added thionyl chloride (8.59 ml, 118.42 mmol). The reaction mixture was stirred for 4 h at RT. The solvent was removed under vacuum pump to afford 4-(chloromethyl)-6-(difluoromethoxy)-5-methylpyrimidine 50 as a brown solid. Yield: 14 g (85%); ¹H NMR (400 MHz, DMSO-d6) δ=8.74 (s, 1H), 7.77 (t, 1H, J=95.4 Hz), 4.81 (s, 2H), 2.24 (s, 3H).

Example 1

1-(1-(2,6-difluorophenyl)ethyl)-N-(2-fluoroethyl)-1H-pyrrolo[3,2-b]pyridine-3-carboxamide

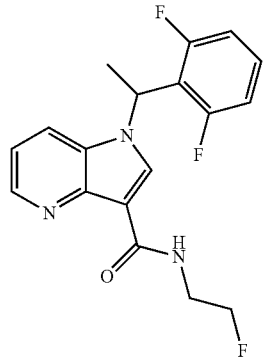 [SMILES: CC(c1c(F)cccc1F)n1cc(C(=O)NCCF)c2ncccc21]

See FIG. 16(a). 1-(1-(2,6-difluorophenyl)ethyl)-1H-pyrrolo[3,2-b]pyridine-3-carboxylic acid (0.090 g, 0.30 mmol), 2-fluoroethanamine (0.019 g, 0.30 mmol) and triethylamine (0.166 mL, 1.19 mmol) was taken in DCM (15 mL) under N2 and stirred. After 5 min, 1-Propanephosphonic acid cyclic anhydride (0.379 g, 1.19 mmol) was added. The resulting reaction was stirred at rt for 40 min. LCMS analysis showed formation of required product. Reaction was diluted with DCM and water. DCM layer was extracted and washed with brine and dried over sodium sulphate and concentrated. Purification was done on Waters RP system to get product 1-(1-(2,6-difluorophenyl)ethyl)-N-(2-fluoroethyl)-1H-pyrrolo[3,2-b]pyridine-3-carboxamide (0.040 g, 38.7%) as a solid. ES+MS m/z: 348.40. ¹H NMR (300 MHz, DMSO-d₆) δ ppm 2.05 (d, J=6.97 Hz, 3 H ) 3.67 (q, J=5.21 Hz, 1 H ) 3.71-3.82 (m, 1 H ) 4.49 (t, J=4.90 Hz, 1 H ) 4.65 (t, J=4.99 Hz, 1 H ) 6.22 (q, J=7.16 Hz, 1 H ) 7.13 (t, J=8.57 Hz, 2 H ) 7.29 (dd, J=8.48, 4.71 Hz, 1 H ) 7.34-7.52 (m, 1 H ) 7.80 (d, J=8.29 Hz, 1 H ) 8.41 (s, 1 H ) 8.50 (d, J=4.71 Hz, 1 H ) 8.92 (t, J=5.75 Hz, 1 H ).

Example 2

N-(Cyclopropylmethyl)-1-(5-fluoro-2-methoxybenzyl)-7-methyl-1H-pyrrolo[3,2-b]pyridine-3-carboxamide

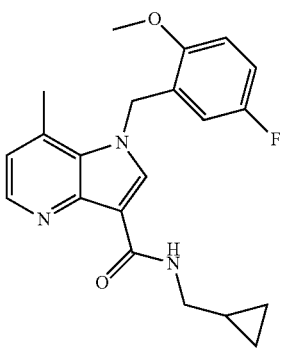 [SMILES: COc1ccc(F)cc1Cn1cc(C(=O)NCC2CC2)c2nccc(C)c21]

See FIG. 16(b). To a stirred solution of 1-(5-fluoro-2-methoxybenzyl)-7-methyl-1H-pyrrolo[3,2-b]pyridine-3-carboxylic acid (0.22 g, 0.000699 moles) in dichloromethane (10 mL) were added 2-fluoroethan-1-amine (0.06 g, 0.000836 moles), triethylamine (0.29 ml, 0.002 moles) and T3P (1.32 ml, 0.002 moles) and the mixture was stirred for 16 h at room temperature. The reaction mixture was poured in to water and extracted with dichloromethane. The combined organic layer was washed with water, brine and the solvent was evaporated under reduced pressure. The crude was purified by flash column chromatography using 50% ethyl acetate in hexane to afford N-(cyclopropylmethyl)-1-(5-fluoro-2-methoxybenzyl)-7-methyl-1H-pyrrolo[3,2-b]pyridine-3-carboxamide as a off-white solid. Yield-24%. ES+MS m/z: 368. $^1$H NMR (400 MHz, DMSO-$d_6$) δ ppm: 0.22-0.24 (m, 2H), 0.48-0.50 (m, 2H), 1.05-1.09 (m, 1H), 2.44 (s, 3H), 3.28 (t, 2H, J=6.2 Hz), 3.86 (s, 3H), 5.63 (s, 2H), 5.97-6.00 (m, 1H), 7.03-7.04 (m, 1H), 7.12-7.14 (m, 2H), 8.22 (s, 1H), 8.37 (d, 1H, J=4.8 Hz), 9.01 (t, 1H, J=5.6 Hz).

Example 3

N-(2-fluoroethyl)-1-((6-methoxy-5-methylpyrimidin-4-yl)methyl)-1H-pyrrolo[3,2-b]pyridine-3-carboxamide

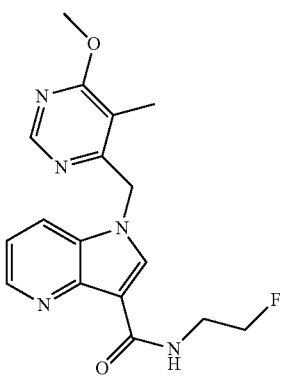 [SMILES: COc1ncnc(Cn2cc(C(=O)NCCF)c3ncccc32)c1C]

See FIG. 16(c). 1-((6-methoxy-5-methylpyrimidin-4-yl)methyl)-1H-pyrrolo[3,2-b]pyridine-3-carboxylic acid (250 mg, 0.84 mmol) was taken in a 100 ml single necked flask equipped with an air condenser connected to nitrogen source. DCM (10 mL) was added to get a suspension. Triethyl amine (1.162 mL, 8.38 mmol) was added to get a clear solution. 1-Propanephosphonic acid cyclic anhydride (1.497 mL, 2.51 mmol) was added followed by the addition of 2-fluoroethanamine hydrochloride (83 mg, 0.84 mmol). The reaction mass was stirred at RT for overnight, suspension was observed. After completion of the reaction, diluted with DCM, added water, and separated the DCM layer washed with brine solution. The DCM layer was dried over sodium sulphate, evaporated and purified the compound by column chromatography. Yield-52%. ES+MS m/z: 344 (M+1). $^1$H NMR (300 MHz, DMSO-d6) δ ppm 2.25 (s, 20 H) 3.67 (d, J=5.46 Hz, 7 H) 3.77 (d, J=5.46 Hz, 7 H) 4.50 (t, J=4.90 Hz, 7 H) 4.66 (t, J=4.99 Hz, 7 H) 5.69 (s, 13 H) 7.26 (dd, J=8.29, 4.71 Hz, 7 H) 7.94 (d, J=8.48 Hz, 7 H) 8.28 (s, 7 H) 8.41 (s, 6 H) 8.49 (d, J=4.52 Hz, 7 H) 8.95 (t, J=5.84 Hz, 7 H).

Example 4

N-(cyclopropylmethyl)-1-((6-methoxy-5-methylpyrimidin-4-yl)methyl)-1H-pyrrolo[3,2-b]pyridine-3-carboxamide

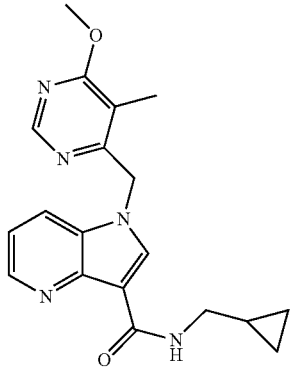 [SMILES: COc1ncnc(Cn2cc(C(=O)NCC3CC3)c3ncccc32)c1C]

See FIG. 16(b). 1-((6-methoxy-5-methylpyrimidin-4-yl)methyl)-1H-pyrrolo[3,2-b]pyridine-3-carboxylic acid (200 mg, 0.67 mmol) was taken in DCM (10 mL). Added 1-Propanephosphonic acid cyclic anhydride (427 mg, 1.34 mmol) followed by the addition of Triethyl amine (339 mg, 3.35 mmol) and cyclopropylmethanamine (95 mg, 1.34 mmol). The reaction mass was stirred at RT for overnight. After the completion of the reaction added water and extracted with DCM. The organic layer was washed with water and brine solution. The organic layer was separated, dried over sodium sulphate. Evaporated the organic layer to get the residue, which was purified by column chromatography to get the pure compound. Yield-74%. ES+MS m/z: 352.38 (M+1). $^1$H NMR (300 MHz, DMSO-$d_6$) δ ppm 0.02 (q, J=4.58 Hz, 2 H) 0.18-0.31 (m, 2 H) 0.83 (t, J=6.88 Hz, 1 H) 2.00 (s, 3 H) 2.98-3.11 (m, 3 H) 3.69 (s, 3 H) 5.43 (s, 2 H) 7.00 (dd, J=8.29, 4.71 Hz, 1 H) 7.68 (dd, J=8.29, 1.13 Hz, 1 H) 7.98 (s, 1 H) 8.17 (s, 1 H) 8.24 (dd, J=4.71, 1.13 Hz, 1 H) 8.55 (t, J=5.75 Hz, 1 H).

Example 5

1-(2,3-difluoro-6-methoxybenzyl)-N-(2-fluoroethyl)-1H-pyrrolo[3,2-b]pyridine-3-carboxamide

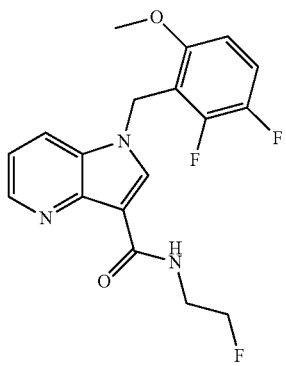 [SMILES: COc1ccc(F)c(F)c1Cn1cc(C(=O)NCCF)c2ncccc21]

See FIG. 17(a). In a 50 mL round-bottomed flask N-(2-fluoroethyl)-1H-pyrrolo[3,2-b]pyridine-3-carboxamide (0.1 g, 0.48 mmol) was DMF (10 mL) to give a colourless suspension. the reaction mixture was cooled to 0° C. and potassium carbonate (0.200 g, 1.45 mmol) and 2-(bromomethyl)-3,4-difluoro-1-methoxybenzene (0.114 g, 0.48 mmol) was added then the RM was stirred at 80° C. for 4 h. The reaction was monitored by LCMS. DMF was concentrated under vacuao, added water and extracted with DCM. The combined organic layer was washed with brine, dried over sodium sulphate, filtered and evaporated to give crude product. The crude material was purified on reverse phase preparative HPLC system to get 1-(2,3-difluoro-6-methoxybenzyl)-N-(2-fluoroethyl)-1H-pyrrolo[3,2-b]pyridine-3-carboxamide (0.060 g, 34.2%). ES+MS m/z: 364 (M+1) $^1$H NMR (DMSO-d6, 300 MHZ): δ ppm 8.90 (br. s., 1 H ), 8.50 (d, J=4.3 Hz, 1 H ), 8.02-8.15 (m, 2 H ), 7.30-7.52 (m, 2 H ), 6.92 (d, J=8.7 Hz, 1 H ), 5.53 (s, 2 H ), 4.63 (t, J=4.4 Hz, 1 H ), 4.47 (t, J=4.8 Hz, 1 H ), 3.86 (s, 3 H ), 3.74 (d, J=5.3 Hz, 1 H ), 3.65 (d, J=5.3 Hz, 1 H ).

Example 6

1-((5-fluoro-2-methoxypyridin-3-yl)methyl)-N-(2-methoxyethyl)-1H-pyrrolo[3,2-bipyridine-3-carboxamide

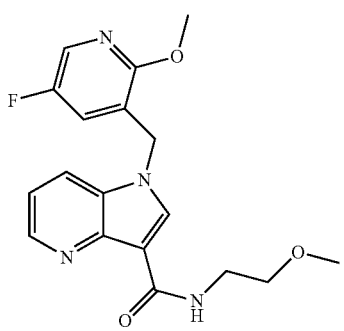 [SMILES: COCCNC(=O)c1cn(Cc2cc(F)cnc2OC)c2cccnc12]

See FIG. 17(b). 1-((5-fluoro-2-methoxypyridin-3-yl)methyl)-1H-pyrrolo[3,2-b]pyridine-3-carboxylic acid (100 mg, 0.33 mmol) was taken in dichloromethane (15 mL) to get a suspension. Triethyl amine (230 mL, 1.66 mmol) was added to get clear solution. Added 1-Propanephosphonic acid cyclic anhydride (198 mL, 0.66 mmol) and stirred at RT for 5 minutes. 2-methoxyethanamine (74.8 mg, 1.00 mmol) was added and stirred the reaction mass at RT for 2 hr. After the completion of the reaction diluted the reaction mass with DCM, washed with water, brine solution. The DCM layer was separated, dried over sodium sulphate and evaporated to get the crude compound. The compound was purified by silica gel chromatography using methanol and dichloromethane as eluent. Yield-63%. ES+MS m/z: 359.1 (M+1). $^1$H NMR (500 MHz, DMSO-d$_6$) δ ppm 3.44-3.52 (m, 2 H ) 3.56 (q, J=5.46 Hz, 2 H ) 3.89 (s, 3 H ) 5.47 (s, 2 H ) 7.31 (dd, J=8.20, 4.73 Hz, 1 H ) 7.46 (dd, J=8.20, 2.84 Hz, 1 H ) 8.09-8.22 (m, 2 H ) 8.31 (s, 1 H ) 8.51 (dd, J=4.73, 0.95 Hz, 1 H ) 8.85 (t, J=5.52 Hz, 1 H ).

Example 7

1-((6-methoxy-5-methylpyrimidin-4-yl)methyl)-N-(2-m ethyl)-1H-pyrrolo[3,2-b]pyridine-3-carboxamide

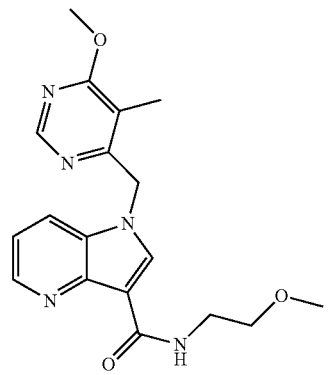 [SMILES: COCCNC(=O)c1cn(Cc2ncnc(OC)c2C)c2cccnc12]

See FIG. 17(c). 1-((6-methoxy-5-methylpyrimidin-4-yl)methyl)-1H-pyrrolo[3,2-b]pyridine-3-carboxylic acid (200 mg, 0.67 mmol) was taken in DCM (10 mL) to get a suspension. Triethyl amine (0.929 mL, 6.70 mmol) was added to get a clear solution. 1-Propanephosphonic acid cyclic anhydride (1.197 mL, 2.01 mmol) was added and stirred at RT for 5 minutes. 2-methoxyethanamine (151 mg, 2.01 mmol) was added and stirred at RT for overnight. After the completion of the reaction, diluted the reaction mass with DCM, washed with water, brine solution and then evaporated to get the crude compound. The compound was purified by silica gel chromatography. Yield-90%. ES+MS m/z: 356.2 (M+1). $^1$H NMR (300 MHz, DMSO-d$_6$) δ ppm 2.24 (s, 3 H ) 3.30 (s, 3 H ) 3.43-3.63 (m, 4 H ) 3.93 (s, 3 H ) 5.68 (s, 2H) 7.24 (dd, J=8.29, 4.71 Hz, 1 H ) 7.92 (dd, J=8.38, 1.22 Hz, 1 H ) 8.25 (s, 1 H ) 8.41 (s, 1 H ) 8.48 (dd, J=4.71, 1.13 Hz, 1 H ) 8.85 (t, J=5.65 Hz, 1 H ).

Example 8

N-(2-fluoroethyl)-1-((6-methoxy-5-methylpyrimidin-4-yl)methyl)-6-methyl-1H-pyrrolo[3,2-b]pyridine-3-carboxamide

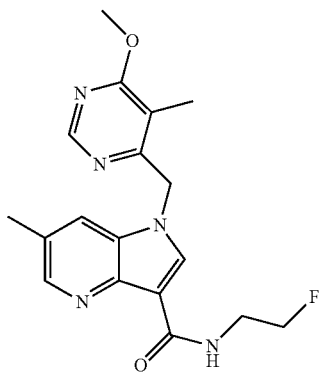 [SMILES: COc1ncnc(Cn2cc(C(=O)NCCF)c3ncc(C)cc32)c1C]

See FIG. 17(*d*). 1-((6-methoxy-5-methylpyrimidin-4-yl)methyl)-6-methyl-1H-pyrrolo[3,2-b]pyridine-3-carboxylic acid (0.190 gm, 0.61 mmol) and 2-fluoroethanamine (0.077 g, 1.22 mmol), TEA (0.254 mL, 1.83 mmol) was added. After 3 min 1-Propanephosphonic acid cyclic anhydride (0.484 g, 1.52 mmol) was added. The resulting reaction mixture was stirred at rt for 50 min. LCMS analysis confirmed the formation of required product. Reaction was diluted with DCM and water. DCM layer was extracted and washed with brine and dried over sodium sulphate and concentrated. Purification was performed on Waters RP system to get product N-(2-fluoroethyl)-1-((6-methoxy-5-methylpyrimidin-4-yl)methyl)-6-methyl-1H-pyrrolo[3,2-b]pyridine-3-carboxamide (0.090 g, 41.4%). ES+MS m/z: 358.36. $^1$H NMR (300 MHz, DMSO-$d_6$) δ ppm 2.17-2.30 (3, 3 H) 2.40 (s, 3 H) 3.59-3.73 (m, 1 H) 3.73-3.83 (m, 1 H) 3.94 (s, 3 H) 4.50 (t, J=4.99 Hz, 1 H) 4.66 (t, J=4.99 Hz, 1 H) 5.64 (s, 2 H) 7.76 (s, 1 H) 8.15 (s, 1 H) 8.35 (s, 1 H) 8.42 (s, 1 H) 8.87 (t, J=5.84 Hz, 1 H).

Example 9

N-(2-hydroxyethyl)-1-((6-methoxy-5-methylpyrimidin-4-yl)methyl)-1H-pyrrolo[3,2-b]pyridine-3-carboxamide

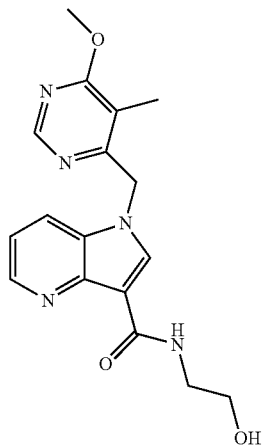 [SMILES: COc1ncnc(Cn2cc(C(=O)NCCO)c3ncccc32)c1C]

See FIG. 18(*a*). 1-((6-methoxy-5-methylpyrimidin-4-yl)methyl)-1H-pyrrolo[3,2-b]pyridine-3-carboxylic acid (1 g, 3.35 mmol) was taken in DCM (20 mL) to get a suspension. Triethyl amine (1.394 mL, 10.06 mmol) was added followed by the addition of 1-Propanephosphonic acid cyclic anhydride (3.991 mL, 6.70 mmol). The reaction mass was stirred at RT for 5 minutes. Ethanol amine (6.02 mL, 10.06 mmol) was added and stirred at RT for 2 h. After completion of the reaction, diluted with DCM and then washed with water and brine solution. The organic layer was separated, dried, evaporated and the crude compound was purified by silica gel chromatography. Yield-45%. ES+MS m/z: 342 (M+1). $^1$H NMR (300 MHz, DMSO-$d_6$) δ ppm 2.24 (s. 3 H) 3.37-3.64 (m, 4 H) 3.94 (s, 3 H) 4.80 (t, J=4.99 Hz, 1 H) 5.67 (s, 2 H) 7.24 (dd, J=8.29, 4.52 Hz, 1 H) 7.92 (d, J=8.10 Hz, 1 H) 8.23 (s, 1 H) 8.41 (s, 1 H) 8.47 (d, J=4.52 Hz, 1 H) 8.85 (t, J=5.37 Hz, 1 H).

Example 10

N-(cyclopropylmethyl)-1-((6-methoxy-5-methylpyrimidin-4-yl)methyl)-6-methyl-1H-pyrrolo[3,2-b]pyridine-3-carboxamide

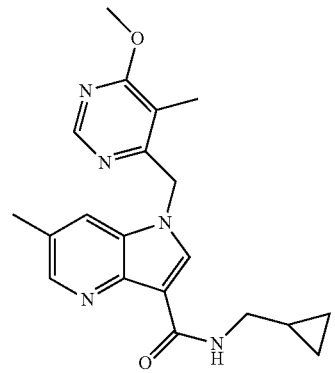 [SMILES: COc1ncnc(Cn2cc(C(=O)NCC3CC3)c3ncc(C)cc32)c1C]

See FIG. 18(*b*). 1-((6-methoxy-5-methylpyrimidin-4-yl)methyl)-6-methyl-1H-pyrrolo[3,2-b]pyridine-3-carboxylic acid (0.100 g, 0.32 mmol) and cyclopropylmethanamine (0.046 g, 0.64 mmol), TEA (0.134 mL, 0.96 mmol) was added. After 3 min 1-Propanephosphonic acid cyclic anhydride (0.255 g, 0.80 mmol) was added. The resulting reaction mixture was stirred at rt for 50 min. LCMS analysis showed formation of required product. Reaction was diluted with DCM and water. DCM layer was extracted and washed with brine and dried over sodium sulphate and concentrated. Purification was done on Waters RP system to get product N-(cyclopropylmethyl)-1-((6-methoxy-5-methylpyrimidin-4-yl)methyl)-6-methyl-H-pyrrolo[3,2-b]pyridine-3-carboxamide (0.045 g, 38.5%). ES+MS m/z: 366.44. $^1$H NMR (300 MHz, DMSO-$d_6$) δ ppm 0.21-0.33 (m, 2H) 0.41-0.56 (m, 2 H) 1.08 (m, J=6.97 Hz, 1 H) 2.24 (s, 3 H) 2.40 (s, 3 H) 3.26 (d., 2 H) 3.94 (s, 3 H) 5.63 (s, 2 H) 7.75 (s, 1 H) 8.11 (s, 1 H) 8.35 (s, 1 H) 8.42 (s, 1H) 8.74 (t, J=5.65 Hz, 1 H).

Example 11

1-((6-methoxy-5-methylpyrimidin-4-yl)methyl)-N-(2-methoxyethyl)-6-methyl-1H-pyrrolo[3,2-b]pyridine-3-carboxamide

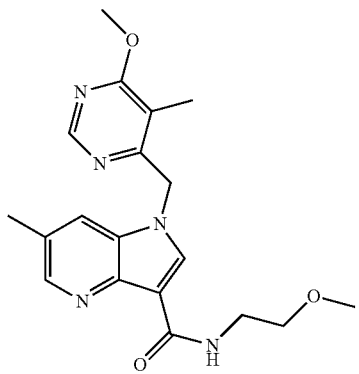

See FIG. 18(c). 1-((6-methoxy-5-methylpyrimidin-4-yl)methyl)-6-methyl-1H-pyrrolo[3,2-b]pyridine-3-carboxylic acid (0.100 g, 0.32 mmol) and 2-methoxyethanamine (0.048 g, 0.64 mmol), TEA (0.134 mL, 0.96 mmol) was added. After 3 min, 1-Propanephosphonic acid cyclic anhydride (0.255 g, 0.80 mmol) was added. The resulting reaction mixture was stirred at rt for 50 min. LCMS analysis showed formation of required product. Reaction was diluted with DCM and water. DCM layer was extracted and washed with brine and dried over sodium sulphate and concentrated. Purification was done on Waters RP system to get product 1-((6-methoxy-5-methylpyrimidin-4-yl)methyl)-N-(2-methoxyethyl)-6-methyl-1H-pyrrolo[3,2-b]pyridine-3-carboxamide (0.045 g, 38.0%). ES+MS m/z: 370.21. $^1$H NMR (300 MHz, DMSO-d6) δ ppm 2.17-2.28 (s, 3H) 2.40 (s, 3 H) 3.30 (s, 13 H) 3.50 (d, J=4.52 Hz, 2 H) 3.55 (t, J=5.18 Hz, 2 H) 3.94 (s, 3 H) 5.63 (s, 2 H) 7.74 (s, 1 H) 8.12 (s, 1 H) 8.34 (s, 1 H) 8.42 (s, 1 H) 8.78 (t, J=5.46 Hz, 1H).

Example 12

N-(2-fluoroethyl)-1-((3-methyl-4-(2,2,2-trifluoroethoxy)pyridin-2-yl)methyl)-1H-pyrrolo[3,2-b]pyridine-3-carboxamide

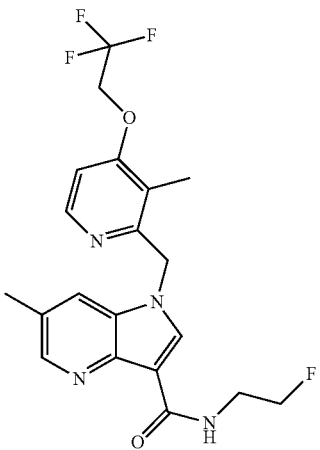 [SMILES: Cc1cnc2c(C(=O)NCCF)cn(Cc3nccc(OCC(F)(F)F)c3C)c2c1]

See FIG. 18(d). 1-((3-methyl-4-(2,2,2-trifluoroethoxy)pyridin-2-yl)methyl)-1H-pyrrolo[3,2-b]pyridine-3-carboxylic acid (100 mg, 0.27 mmol) was taken in DCM (10 mL) to get a clear solution. Triethyl amine (0.190 mL, 1.37 mmol) was added followed by the addition of 1-Propanephosphonic acid cyclic anhydride solution in ethyl acetate (0.326 mL, 0.55 mmol) and stirred the reaction mass for 5 minutes. 2-Fluoroethylamine hydrochloride (54.5 mg, 0.55 mmol) was added and stirred the reaction mass for 3 h. After completion of the reaction, diluted with DCM and then washed with water and brine solution. The organic layer was separated, dried, evaporated and the crude compound was purified by silica gel chromatography using methanol and dichloromethane as eluent. Yield-49%. ES+MS m/z: 411 (M+1). $^1$H NMR (300 MHz, DMSO-d$_6$) δ ppm 2.25 (s, 3 H) 3.67 (q, J=5.21 Hz, 1 H) 3.76 (q, J=5.21 Hz, 1 H) 4.50 (t, J=4.99 Hz, 1 H) 4.66 (t, J=4.90 Hz, 1 H) 4.90 (q, J=8.85 Hz, 2 H) 5.68 (s, 2 H) 7.06 (d, J=5.84 Hz, 1 H) 7.24 (dd, J=8.38, 4.62 Hz, 1 H) 7.93 (d, J=7.35 Hz, 1 H) 8.17 (d, J=5.65 Hz, 1 H) 8.24 (s, 1 H) 8.48 (d, J=3.77 Hz, 1 H) 8.94 (t, J=5.75 Hz, 1 H).

Example 13

N-(2-fluoroethyl)-1-((2-methoxy-5-(trifluoromethyl)pyridin-3-yl)methyl)-1H-pyrrolo[3,2-b]pyridine-3-carboxamide

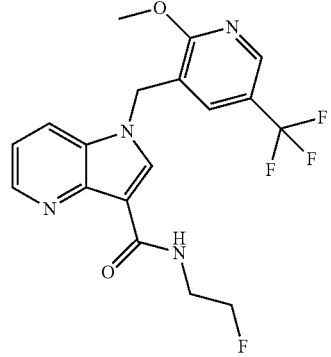 [SMILES: COc1ncc(C(F)(F)F)cc1Cn1cc(C(=O)NCCF)c2ncccc21]

See FIG. 19(a). To a stirred solution of 1-((2-methoxy-5-(trifluoromethyl)pyridin-3-yl)methyl)-1H-pyrrolo[3,2-b]pyridine-3-carboxylic acid (60 mg, 0.177 mmol) in dichloromethane (5 mL) were added 2-fluoroethan-1-amine hydrochloride (26 mg, 0.26 mmol), triethylamine (0.053 g, 0.531 mmol) and T3P (0.33 g, 0.531 mmol) and reaction mixture was stirred for 16 h at room temperature. Then the reaction mixture was poured in to water and extracted with dichloromethane. The reaction mixture was poured into water and extracted with dichloromethane. The combined organic layer was washed with water,brine and solvent was evaporated under reduced pressure. The crude product was purified by silica gel column chromatography using silica gel column chromatography to afford N-(2-fluoroethyl)-1-((2-methoxy-5-(trifluoromethyl)pyridin-3-yl)methyl)-1H-pyrrolo[3,2-b]pyridine-3-carboxamide as a white solid. Yield: 15 mg. (22.3%). ES+MS m/z: 397. $^1$H NMR (400 MHz, DMSO-d$_6$): δ ppm 3.66-3.70 (m, 2H), 3.72-3.76 (m, 2H), 4.00 (s, 3H), 4.50-4.52 (m, 2H), 4.62-4.64 (m, 2H), 5.76 (s, 2H), 7.30-7.33 (m, 1H), 7.92 (s, 1H), 8.11 (d, 1H, J=8.3 Hz), 8.32 (s, 1H), 8.50-8.52 (m, 1H), 8.66-8.67 (m, 1H), 8.94 (t, 1H, J=5.6 Hz).

Example 14

1-((5-cyano-2-methoxypyridin-3-yl)methyl)-N-(2-fluoroethyl)-1H-pyrrolo[3,2-b]pyridine-3-carboxamide

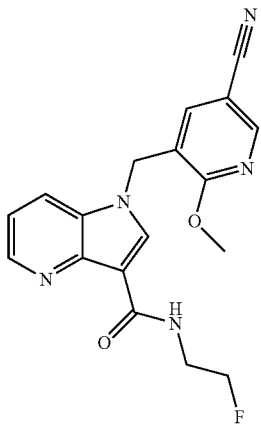 [SMILES: COc1ncc(C#N)cc1Cn1cc(C(=O)NCCF)c2ncccc21]

See FIG. 19(b). To a solution of 1-((5-cyano-2-methoxy pyridin-3-yl)methyl)-1H-pyrrolo[3,2-b]pyridine-3-carboxylic acid (0.10 gm, 0.32 mmol) in DCM, were added TEA (0.0.98 g, 0.135 ml, 0.97 mmol), 2-fluoroethan-1-amine hydrochloride (0.095 g, 0.97 mmol) and T3P (0.308 g, 0.97 mmol). The reaction mixture was stirred at RT for 12 h. Water was added to the reaction mixture and extracted with DCM. The combined organic layer was washed with water, brine, dried over sodium sulfate, and concentrated at reduced pressure. The crude product was purified by flash column chromatography to afford 1-((5-yano-2-methoxypyridin-3-yl)methyl)-N-(2-fluoroethyl)-1H-pyrrolo[3,2-b]pyridine-3-carboxamide- the product as a solid (17 mg, 14.9%). ES+MS m/z: 354. $^1$H NMR (400 MHz, DMSO-d6): δ 8.95 (t, J=5.80 Hz, 1H), 8.66 (d, J=2.04 Hz, 1H), 8.51 (d, J=4.08 Hz, 1H), 8.32 (s, 1H), 8.11 (d, J=8.40 Hz, 1H), 7.93 (d, J=1.92 Hz, 1H), 7.30-7.33 (m, 1H), 5.49 (s, 2H), 5.30 (t, J=5.00 Hz, 1H), 4.51 (t, J=4.96 Hz, 1H), 3.91 (s, 3H), 3.72-3.76 (m, 1H), 3.66-3.70 (m, 1H).

Example 15

1-((5-fluoro-2-methoxypyridin-3-yl)methyl)-N-(2-fluoroethyl)-6-methyl-1H-pyrrolo[3,2-b]pyridine-3-carboxamide

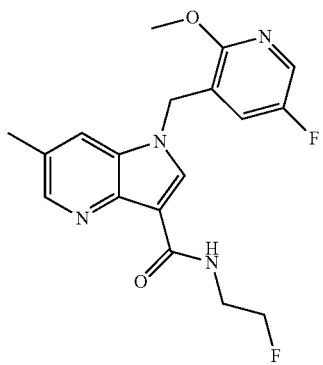 [SMILES: COc1ncc(F)cc1Cn1cc(C(=O)NCCF)c2ncc(C)cc21]

See FIG. 19(c). 1-((5-fluoro-2-methoxypyridin-3-yl)methyl)-6-methyl-1H-pyrrolo[3,2-b]pyridine-3-carboxylic acid (60 mg, 0.19 mmol) and 2-fluoroethanamine (21.60 mg, 0.34 mmol), TEA (0.080 mL, 0.57 mmol) was added. After 3 min 1-Propanephosphonic acid cyclic anhydride (151 mg, 0.48 mmol) was added. The resulting reaction mixture was stirred at rt for 50 min. LCMS analysis showed formation of required product. Reaction was diluted with DCM and water. DCM layer was extracted and washed with brine and dried over sodium sulphate and concentrated. Purification was done on Waters RP system to get product 1-((5-fluoro-2-methoxypyridin-3-yl)methyl)-N-(2-fluoroethyl)-6-methyl-1H-pyrrolo[3,2-b]pyridine-3-carboxamide (25.00 mg, 36.5%). ES+MS m/z: 361.33. $^1$H NMR (300 MHz, DMSO-d$_6$) δ ppm 2.44 (s, 3 H) 3.65 (d, J=5.27 Hz, 1 H) 3.75 (d, J=5.27 Hz, 1 H) 3.90 (s, 3 H) 4.49 (t, J=4.99 Hz, 1H) 4.64 (t, J=4.99 Hz, 1 H) 5.42 (s, 2 H) 7.36 (dd, J=8.29, 3.01 Hz, 1 H) 7.93 (s, 1H) 8.12 (d, J=3.01 Hz, 1 H) 8.23 (s, 1H) 8.38 (s, 5 H) 8.88 (t, J=5.65 Hz, 1 H).

Example 16

(S)—N-(2-fluoropropyl)-1-((6-methoxy-5-methylpyrimidin-4-yl)methyl)-6-methyl-1H-pyrrolo[3,2-b]pyridine-3-carboxamide

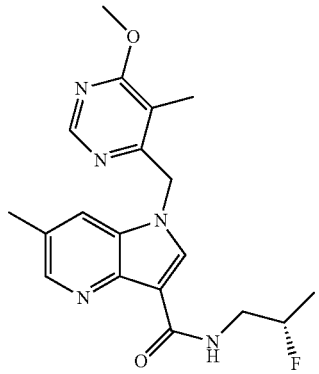 [SMILES: COc1ncnc(Cn2cc(C(=O)NC[C@H](C)F)c3ncc(C)cc32)c1C]

See FIG. 19(d). 1-((6-methoxy-5-methylpyrimidin-4-yl)methyl)-6-methyl-1H-pyrrolo[3,2-b]pyridine-3-carboxylic acid (100 mg, 0.32 mmol) was taken in dichloromethane (10 mL) to get a suspension. Added triethyl amine (0.133 mL, 0.96 mmol) followed by the addition of 1-Propanephosphonic acid cyclic anhydride (0.381 mL, 0.64 mmol). The reaction mass was stirred at RT for 5 minutes. (R)-2-fluoropropan-1-amine (49.4 mg, 0.64 mmol) was added and stirred at RT for overnight. After the completion of the reaction, diluted the reaction mass with DCM, washed ith water, and brine solution. The organic layer was dried over sodium sulphate, evaporated and the crude compound was purified by silica gel chromatography. Yield-75%. ES+MS m/z: 373.2 (M+1). $^1$H NMR (300 MHz, DMSO-d$_6$) δ ppm 1.25-1.42 (m, 4 H) 2.24 (s, 3H) 2.40 (s, 3 H) 3.42-3.81 (m, 2 H) 3.94 (s, 3 H) 4.65-4.85 (m, 1 H) 4.93 (td, J=6.50, 3.39 Hz, 1 H) 5.64 (s, 2 H) 7.76 (s, 1 H) 8.16 (s, 1 H) 8.29-8.47 (m, 2 H) 8.91 (t, J=6.03 Hz, 1 H).

Example 17

N-(2-hydroxyethyl)-1-((6-methoxy-5-methylpyrimidin-4-yl)methyl)-6-methyl-1H-pyrrolo[3,2-b]pyridine-3-carboxamide

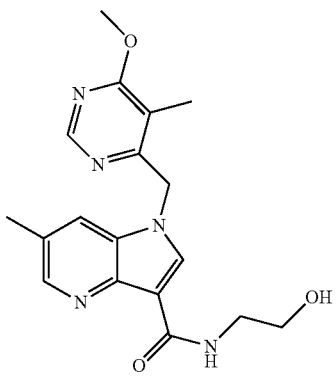 [SMILES: COc1ncnc(Cn2cc(C(=O)NCCO)c3ncc(C)cc32)c1C]

See FIG. 20(*a*). 1-((6-methoxy-5-methylpyrimidin-4-yl)methyl)-6-methyl-1H-pyrrolo[3,2-b]pyridine-3-carboxylic acid (75 mg, 0.24 mmol) was taken in dichloromethane (10 mL) to get a suspension. Added triethyl amine (0.0669 mL, 0.48 mmol) followed by the addition of 1-Propanephosphonic acid cyclic anhydride (0.286 mL, 0.48 mmol). The reaction mass was stirred at RT for 5 minutes. Ethanol amine (0.029 mL, 0.48 mmol) was added and stirred at RT for overnight. After the completion of the reaction, diluted the reaction mass with DCM, washed with water and brine solution. The DCM layer was dried over sodium sulphate, evaporated to get the crude compound which was purified by column chromatography. Yield-52.7%. ES+MS m/z: 356.4 (M+1). $^1$H NMR (300 MHz, DMSO-d$_6$) δ ppm 2.23 (s, 3 H) 2.39 (s, 3 H) 3.39-3.65 (m, 4 H) 3.93 (s, 3 H) 4.84 (t, J=5.09 Hz, 1 H) 5.63 (s, 2 H) 7.74 (s, 1 H) 8.12 (s, 1 H) 8.33 (s, 1 H) 8.41 (s, 1 H) 8.80 (t, J=5.65 Hz, 1 H).

Example 18

1-((5-fluoro-2-methoxy-6-methylpyridin-3-yl)methyl)-N-(2-fluoroethyl)-1H-pyrrolo[3,2-b]pyridine-3-carboxamide

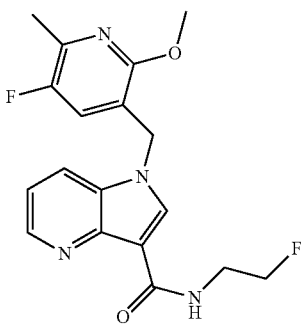 [SMILES: COc1nc(C)c(F)cc1Cn1cc(C(=O)NCCF)c2ncccc21]

See FIG. 20(*b*). To the stirred solution of methyl 1-((5-fluoro-2-methoxy-6-methylpyridin-3-yl)methyl)-1H-pyrrolo[3,2-b]pyridine-3-carboxylic acid (0.15 g, 0.47 mmol) in dichloromethane (10 mL), were added 2-fluoroethan-1-amine hydrochloride (71 mg, 0.71 mmol), triethylamine (0.142 g, 1.41 mmol) and T3P (0.9 g, 1.41 mmol) and the mixture was stirred for 16 h at room temperature. Then the reaction mixture was poured into water and extracted with dichloromethane. The combined organic layer was washed with water, brine, dried over sodium sulfate, and concentrated at reduced pressure. The residue was purified by silica gel column chromatography to yield 1-((5-fluoro-2-methoxy-6-methylpyridin-3-yl)methyl)-N-(2-fluoroethyl)-1H-pyrrolo[3,2-b]pyridine-3-carboxamide as a white solid. Yield: 30 mg (18%). ES+MS m/z: 361 (M+1). $^1$H NMR (400 MHz, DMSO-d$_6$): δ ppm 2.31 (d, 3H, J=2.9 Hz), 3.64-3.68 (m, 2H), 3.71-3.75 (m, 2H), 3.85 (s, 3H), 4.49-4.51 (m, 2H), 4.61-4.63 (m, 2H), 5.41 (s, 2H), 7.28-7.32 (m, 1H), 7.45 (d, 1H, J=9.0 Hz), 8.08-8.11 (m, 1H), 8.29 (s, 1H), 8.49-8.50 (m, 1H), 8.92 (t, 1H, J=5.8 Hz).

Example 19

6-fluoro-N-(2-fluoroethyl)-1-((6-methoxy-5-methylpyrimidin-4-yl)methyl)-1H-pyrrolo[3,2-b]pyridine-3-carboxamide

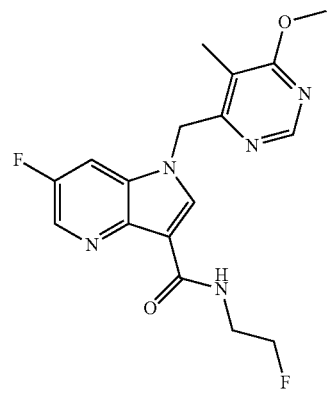 [SMILES: COc1ncnc(Cn2cc(C(=O)NCCF)c3ncc(F)cc32)c1C]

See FIG. 20(*c*). 6-fluoro-1-((6-methoxy-5-methylpyrimidin-4-yl)methyl)-1H-pyrrolo[3,2-b]pyridine-3-carboxylic acid (20 mg, 0.06 mmol) and 2-fluoroethanamine (7.18 mg, 0.11 mmol), TEA (0.026 mL, 0.19 mmol) was added. After 3 min, 1-Propanephosphonic acid cyclic anhydride (50.3 mg, 0.16 mmol) was added. The resulting reaction mixture was stirred at rt for 50 min. LCMS analysis showed formation of required product. Reaction was diluted with DCM and water. DCM layer was extracted and washed with brine and dried over sodium sulphate and concentrated. Purification was done on Waters RP system to get product 6-fluoro-N-(2-fluoroethyl)-1-((6-methoxy-5-methylpyrimidin-4-yl)methyl)-1H-pyrrolo[3,2-b]pyridine-3-carboxamide (20.00 mg, 88%). ES+MS m/z: 362. $^1$H NMR (300 MHz, DMSO-d$_6$) δ ppm 2.24 (s, 3 H) 3.57-3.70 (q, 1 H) 3.70-3.80 (q, 1 H) 3.94 (s, 3 H) 4.43-4.58 (t, 1 H) 4.66 (t, J=4.99 Hz, 1 H) 5.68 (s, 2 H) 8.03 (dd, J=9.89, 2.54 Hz, 1 H) 8.29 (s, 6 H) 8.40 (s, 1 H) 8.53 (t, J=2.07 Hz, 1 H) 8.71 (t, J=5.84 Hz, 1 H).

Example 20

6-bromo-N-(2-fluoroethyl)-1-((6-methoxy-5-methylpyrimidin-4-yl)methyl)-1H-pyrrolo[3,2-b]pyridine-3-carboxamide

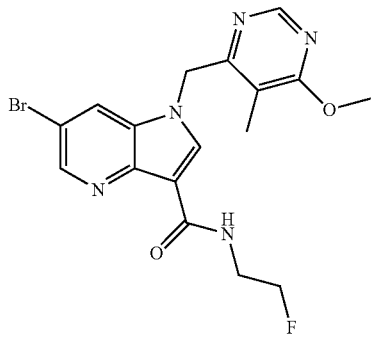 [SMILES: COc1ncnc(Cn2cc(C(=O)NCCF)c3ncc(Br)cc32)c1C]

See FIG. 20(d). To a stirred solution of 6-bromo-1-((6-methoxy-5-methylpyrimidin-4-yl)methyl)-1H-pyrrolo[3,2-b]pyridine-3-carboxylic acid (0.13 g, 0.34 mmol) in dichloromethane (10 mL), were added 2-fluoroethan-1-amine (0.06 g, 0.68 mmol), triethylamine (0.1 g, 1.02 mmol) and T3P (0.32 g, 1.02 mmol) and the mixture was stirred at RT for 16 h. Then the reaction mixture was poured into water and extracted with dichloromethane. The organic layer was washed with brine and concentrated. The crude product was purified by silica gel column chromatography and subsequent PREP purification to afford 6-bromo-N-(2-fluoroethyl)-1-((6-methoxy-5-methylpyrimidin-4-yl)methyl)-1H-pyrrolo[3,2-b]pyridine-3-carboxamide as a white solid. Yield: 25 mg (17%). ES+MS m/z: 424.2 (M+1). $^1$H NMR (400 MHz, DMSO-$d_6$): δ ppm 2.24 (s, 3H), 3.68 (bs, 1H), 3.75 (bs, 1H), 4.51 (bs, 1H), 4.64 (bs, 1H), 5.70 (s, 2H), 8.28 (s, 1H), 8.39 (d, 1H, J=10.9 Hz), 8.58 (s, 1H), 8.64 (bs, 2H)

Example 21

N-(2-fluoroethyl)-6-methyl-1-((3-methyl-4-(2,2,2-trifluoroethoxy)pyridin-2-yl)methyl)-1H-pyrrolo[3,2-b]pyridine-3-carboxamide

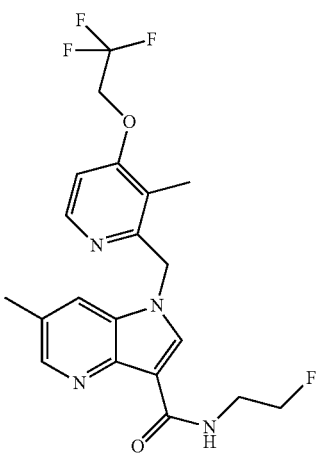 [SMILES: Cc1cnc2c(C(=O)NCCF)cn(Cc3nccc(OCC(F)(F)F)c3C)c2c1]

See FIG. 21(a). 6-methyl-1-((3-methyl-4-(2,2,2-trifluoroethoxy)pyridin-2-yl)methyl)-1H-pyrrolo[3,2-b]pyridine-3-carboxylic acid (111 mg, 0.29 mmol) was taken dichloromethane (10 mL). Triethyl amine (0.204 mL, 1.46 mmol) was added to get a clear solution. 1-Propanephosphonic acid cyclic anhydride (0.348 mL, 0.59 mmol) was added and stirred at RT for 5 minutes. Added 2-Fluoroethylamine hydrochloride (87 mg, 0.88 mmol) and stirred at RT for overnight. After the completion of the reaction, diluted the reaction mass with dichloromethane, washed with water, brine solution. The organic layer was separated, dried over sodium sulphate, evaporated to get the crude compound. The compound was purified by silica gel chromatography using methanol and dichloromethane as eluent. Yield-44.3%. ES+MS m/z: 425.2 (M+1). $^1$H NMR (300 MHz, DMSO-$d_6$) δ ppm 2.24 (s, 3H) 2.39 (s, 3H) 3.66 (q, J=5.21 Hz, 1H) 3.75 (q, J=5.15 Hz, 1H) 4.49 (t, J=4.99 Hz, 1H) 4.65 (t, J=4.99 Hz, 1H) 4.90 (q, J=8.85 Hz, 2H) 5.63 (s, 2H) 7.07 (d, J=5.65 Hz, 1H) 7.76 (s, 1H) 8.11 (s, 1H) 8.17 (d, J=5.65 Hz, 1H) 8.34 (s, 1H) 8.88 (t, J=5.84 Hz, 1H).

Example 22

(S)—N-(2-fluoropropyl)-1-((2-methoxy-5-(trifluoromethyl)pyridin-3-yl)methyl)-6-methyl-1H-pyrrolo[3,2-b]pyridine-3-carboxamide

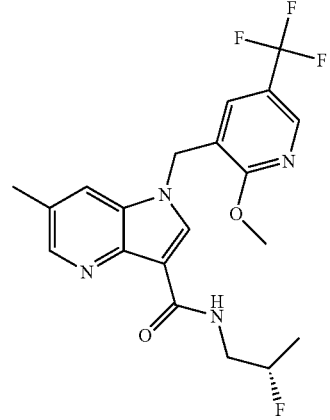 [SMILES: COc1ncc(C(F)(F)F)cc1Cn1cc(C(=O)NC[C@H](C)F)c2ncc(C)cc21]

See FIG. 21(b). In a 25 mL thermal vial was charged with 1-((2-methoxy-5-(trifluoromethyl)pyridin-3-yl)methyl)-6-methyl-1H-pyrrolo[3,2-b]pyridine-3-carboxylic acid (100 mg, 0.27 mmol) and HATU (125 mg, 0.33 mmol) were taken in NMP (4 mL) and stirred for 10 min at rt. Then (S)-2-fluoropropan-1-amine hydrochloride (37.3 mg, 0.33 mmol) and triethyl amine (0.114 mL, 0.82 mmol) were added and stirred for 1 h at RT. The LCMS showed completion of the reaction. The reaction mixture was poured into water and extracted with chloroform. The organic layer was dried and concentrated and crude was submitted to reverse phase purification. The pure fractions were concentrated to get (S)—N-(2-fluoropropyl)-1-((2-methoxy-5-(trifluoromethyl)pyridin-3-yl)methyl)-6-methyl-1H-pyrrolo[3,2-b]pyridine-3-carboxamide (82 mg, 70.6%) a solid. ES+MS m/z: 425 (M+1). $^1$H NMR (300 MHz, DMSO-$d_6$) δ ppm 1.15-1.44 (m, 3H) 2.44 (s, 3H) 3.39-3.79 (m, 2H) 3.98 (s, 3H) 4.75 (td, J=6.50, 3.39 Hz, 1H) 4.92 (td, J=6.50, 3.20 Hz, 1H) 5.48 (s, 2 H ) 7.81 (d, J=2.26 Hz, 1 H ) 7.91-8.03 (m, 1H) 8.25 (s, 1 H ) 8.34-8.42 (m, 1 H ) 8.53-8.62 (m, 1 H ) 8.90 (t, J=5.93 Hz, 1 H ).

Example 23

1-((6-methoxy-5-methylpyrimidin-4-yl)methyl)-N-(2-(trifluoromethoxy)ethyl)-1H-pyrrolo[3,2-b]pyridine-3-carboxamide

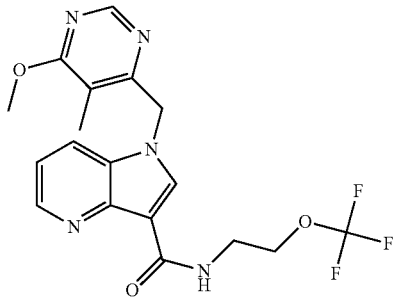 [SMILES: COc1ncnc(Cn2cc(C(=O)NCCOC(F)(F)F)c3ncccc32)c1C]

See FIG. 21(c). 1-((6-methoxy-5-methylpyrimidin-4-yl)methyl)-1H-pyrrolo[3,2-b]pyridine-3-carboxylic acid (40 mg, 0.13 mmol) was taken in a 50 ml single necked flask equipped with an air condenser connected to nitrogen source. NMP (3 ml, 31.17 mmol) was added to get a solution. Triethyl amine (0.056 ml, 0.40 mmol) was added followed by the addition of 2-(trifluoromethoxy)ethanamine hydrochloride (44.4 mg, 0.27 mmol). The reaction mass was stirred at RT for 5 minutes. HATU (61.2 mg, 0.16 mmol) was added and stirred at RT for 30 min. After the completion of the reaction, few drops of methanol was added and clear solution was subjected for reverse phase HPLC purification to get 1-((6-methoxy-5-methylpyrimidin-4-yl)methyl)-N-(2-(trifluoromethoxy)ethyl)-1H-pyrrolo[3,2-b]pyridine-3-carboxamide (15.00 mg, 27.3%). ES+MS m/z: 410 (M+1). $^1$H NMR (300 MHz, DMSO-d6) δ ppm 2.25 (s, 3 H ) 3.68-3.80 (m, 2 H ) 3.93 (s, 3 H ) 4.24 (t, J=5.27 Hz, 2 H ) 5.69 (s, 2 H ) 7.26 (dd, J=8.29, 4.71 Hz, 1 H ) 7.94 (d, J=7.35 Hz, 1 H ) 8.28 (s, 1 H ) 8.38-8.54 (m, 2 H ) 8.96 (s, 1 H).

Example 24

(S)-1-((5-fluoro-2-methoxypyridin-3-yl)methyl)-N-(2-fluoropropyl)-6-methyl-1H-pyrrolo[3,2-b]pyridine-3-carboxamide

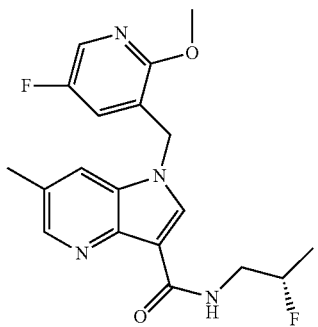 [SMILES: COc1ncc(F)cc1Cn1cc(C(=O)NC[C@H](C)F)c2ncc(C)cc21]

See FIG. 21(d). 1-((5-fluoro-2-methoxypyridin-3-yl)methyl)-6-methyl-1H-pyrrolo[3,2-b]pyridine-3-carboxylic acid (147 mg, 0.47 mmol) was taken in a 50 ml single necked flask equipped with an air condenser connected to nitrogen source. NMP (3 ml, 31.17 mmol) was added to get a suspension. HATU (213 mg, 0.56 mmol) was added followed by the addition of (S)-2-fluoropropan-1-amine (71.9 mg, 0.93 mmol). The reaction mass was stirred at RT for 5 minutes. Triethyl amine (0.195 ml, 1.40 mmol) was added and stirred at RT for 10 minutes.

After the completion of the reaction added water, and extracted with ethyl acetate. The organic layer was dried over sodium sulphate, evaporated to get the crude compound. The crude compound was purified by Gilson prep HPLC to get (S)-1-((5-fluoro-2-methoxypyridin-3-yl)methyl)-N-(2-fluoropropyl)-6-methyl-1H-pyrrolo[3,2-b]pyridine-3-carboxamide (110 mg, 63.0%). ES+MS m/z: 375 (M+1). $^1$H NMR (300 MHz, DMSO-d6) δ ppm 1.24-1.37 (m, 3 H ) 2.44 (s, 3 H ) 3.47 (s, 1 H ) 3.64 (br. s., 1 H ) 3.75 (s, 1 H ) 3.90 (s, 3 H ) 4.76 (br. s., 1 H ) 4.90 (br. s., 1 H ) 5.42 (s, 2 H ) 7.38 (s, 1 H ) 7.93 (s, 1 H ) 8.12 (d, J=3.01 Hz, 1 H ) 8.23 (s, 1 H ) 8.38 (s, 1 H) 8.90 (s, 1 H ).

Example 25

2-cyclopropyl-N-(1-((6-methoxy-5-methylpyrimidin-4-yl)methyl)-1H-pyrrolo[3,2-b]pyridin-3-yl)acetamide

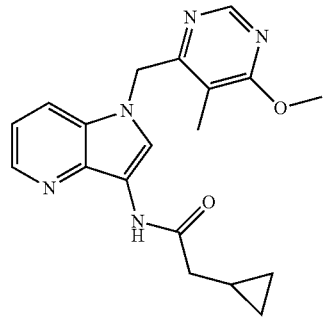 [SMILES: COc1ncnc(Cn2cc(NC(=O)CC3CC3)c3ncccc32)c1C]

See FIG. 22.

3-Nitro-1H-pyrrolo[3,2-b]pyridine (25b)

To a solution of compound 1 (5 g, 0.042 moles) in con.H$_2$SO$_4$ (50 mL), con.HNO$_3$ (3 mL, 0.063 mole) was added at –10° C. At this temperature the reaction mixture was stirred for 5 h. Then the mixture was poured into ice cold water (100 mL), neutralized with aq. NaOH (10%) and extracted with ethylacetate (2×100 mL). The combined organic layer was washed with brine and the solvent was evaporated under reduced pressure to yield 3-Nitro-1H-pyrrolo[3,2-b]pyridine (25b) 3 g (43.4%).

1-((6-methoxy-5-methylpyrimidin-4-yl)methyl)-3-nitro-1H-pyrrolo[3,2-b]pyridine (25c)

To a stirred suspension of 3-Nitro-1H-pyrrolo[3,2-b]pyridine (25b) (0.5 g, 3.04 mmol) and K$_2$CO$_3$ (0.5 g, 9.12 mmol) in DMF (10 mL) was added 4-(chloromethyl)-6-methoxy-5-methylpyrimidine (0.7 g, 6.09 mmol) and the resulting mixture was stirred for 16 h at room temperature. Then the reaction mixture was poured in to water (50 mL) and extracted with dichloromethane (2×50 mL). The combined organic layer was washed with brine and the solvent was evaporated under reduced pressure to yield 1-((6-methoxy-5-methylpyrimidin-4-yl)methyl)-3-nitro-1H-pyrrolo[3,2-b]pyridine (25c) [300 mg (33%)] as a pale yellow solid.

1-((6-methoxy-5-methylpyrimidin-4-yl)methyl)-1H-pyrrolo[3,2-b]pyridin-3-amine (25d)

To a solution of 1-((6-methoxy-5-methylpyrimidin-4-yl)methyl)-3-nitro-1H-pyrrolo[3,2-b]pyridine (0.15 g, 0.58 mmol) in ethanol (5 mL) was added Pd/C (0.03 g). The reaction mixture was hydrogenated under balloon pressure for 16 h at RT. The solvent was filtered and evaporated under the reduced pressure to yield 1-((6-methoxy-5-methylpyrimidin-4-yl)methyl)-1H-pyrrolo[3,2-b]pyridin-3-amine (25d) 0.1 g (74%).

2-cyclopropyl-N-(1-((6-methoxy-5-methylpyrimidin-4-yl)ethyl)-1H-pyrrolo[3,2-b]pyridin-3-yl)acetamide To a stirred solution of 1-((6-methoxy-5-methylpyrimidin-4-yl)methyl)-1H-pyrrolo[3,2-b]pyridin-3-amine (25d) (0.1 g, 0.37 mmol) in dichloromethane (10 mL) were added triethylamine (0.15 mL, 1.11 mmol), T3P (0.35 g, 1.11 mmol) and 2-cyclopropylacetic acid (0.037 g, 0.37 mmol and the mixture was stirred for 16 h at room temperature. Then the reaction mixture was poured into water (20 mL) and extracted with dichloromethane (2×50 mL). The combined organic layer was washed with brine and the solvent was evaporated under reduced pressure. The crude product was purified by silica gel column chromatography using 50% ethylacetate in hexane to afford 2-cyclopropyl-N-(1-((6-methoxy-5-methylpyrimidin-4-yl)methyl)-1H-pyrrolo[3,2-b]pyridin-3-yl)acetamide as off-white solid; yield: 25 mg (19%). ES+MS m/z: 352 (M+1). $^1$H NMR (400 MHz, DMSO-d$_6$): δ ppm 2.25 (s, 3H), 3.67-3.69 (m, 1H), 3.73-3.76 (m, 1H), 4.50-4.52 (m, 1H), 4.62-4.64 (m, 1H), 5.49 (s, 2H), 6.94-6.96 (m, 3H), 7.27-7.30 (m, 1H), 8.08 (d, J=8.2 Hz), 8.45 (s, 1H), 8.50 (d, J=3.88 Hz), 8.92 (t, J=5.6 Hz).

Example 26

1-((5-fluoro-2,6-dimethylpyridin-3-yl)methyl)-N-(2-fluoroethyl)-6-methyl-1H-pyrrolo[3,2-b]pyridine-3-carboxamide

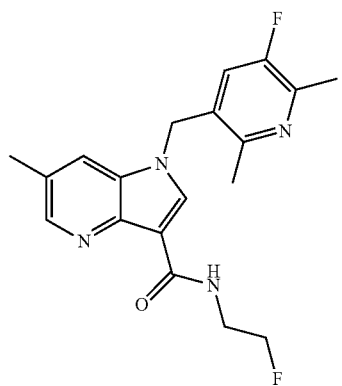

See FIG. 23(a). In a 25 mL thermal vial was charged with 1-((5-fluoro-2,6-dimethylpyridin-3-yl)methyl)-6-methyl-1H-pyrrolo[3,2-b]pyridine-3-carboxylic acid (100 mg, 0.32 mmol) and HATU (146 mg, 0.38 mmol) were taken in NMP (4 mL) and stirred for 10 min at rt. Then 2-fluoroethanamine (20.13 mg, 0.32 mmol) and Triethyl amine (133 mL, 0.96 mmol) were added and stirred for 1 h at rt. The LCMS showed completion of the reaction. The reaction mixture was poured into water and extracted with chloroform. The organic layer was dried and concentrated and crude was submitted to reverse phase purification. The pure fractions were concentrated to get 1-((5-fluoro-2,6-dimethylpyridin-3-yl)methyl)-N-(2-fluoroethyl)-6-methyl-1H-pyrrolo[3,2-b]pyridine-3-carboxamide (75 mg, 65.6%) as a solid. ES+MS m/z: 359 (M+1). $^1$H NMR (300 MHz, DMSO-d$_6$) δ ppm 2.37 (d, J=2.64 Hz, 3 H ) 2.42 (s, 6 H ) 3.66 (d, J=5.46 Hz, 1 H ) 3.75 (d, J=5.27 Hz, 1 H ) 4.49 (t, J=4.90 Hz, 1 H ) 4.65 (t, J=4.99 Hz, 1 H ) 5.52 (s, 2 H ) 6.85 (d, J=10.17 Hz, 1 H ) 7.86 (s, 1 H ) 8.15 (s, 1 H ) 8.34-8.46 (m, 1 H ) 8.89 (t, J=5.84 Hz, 1 H ).

Example 27

N-(2-hydroxyethyl)-6-methyl-1-((3-methyl-4-(2,2,2-trifluoroethoxy)pyridin-2-yl)methyl)-1H-pyrrolo[3,2-b]pyridine-3-carboxamide

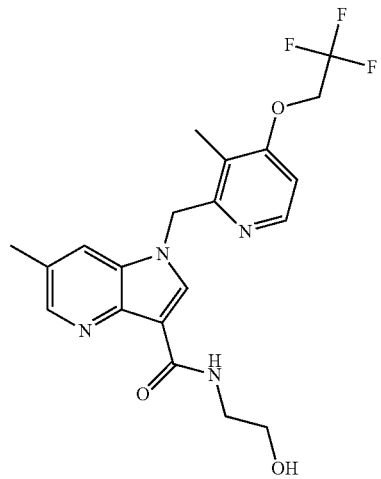 [SMILES: Cc1cnc2c(C(=O)NCCO)cn(Cc3nccc(OCC(F)(F)F)c3C)c2c1]

See FIG. 23(b). 6-methyl-1-((3-methyl-4-(2,2,2-trifluoroethoxy)pyridin-2-yl)methyl)-1H-pyrrolo[3,2-b]pyridine-3-carboxylic acid (55 mg, 0.14 mmol) and NMP (13.95 μl, 0.14 mmol) was taken in a 50 ml single necked flask equipped with an air condenser connected to nitrogen source. HATU (66.2 mg, 0.17 mmol) was added to get a suspension. Added ethanol amine (17.50 μl, 0.29 mmol) followed by the addition of triethyl amine (60.6 μl, 0.43 mmol). The reaction mass was stirred at RT for 5 minutes. LCMS showed completion of the reaction. The crude compound was purified by Gilson Prep HPLC to get pure N-(2-hydroxyethyl)-6-methyl-1-((3-methyl-4-(2,2,2-trifluoroethoxy)pyridin-2-yl)methyl)-1H-pyrrolo[3,2-b]pyridine-3-carboxamide (15.00 mg, 24.49%). ES+MS m/z: 423 (M+I). $^1$H NMR (300 MHz, DMSO-d6) δ ppm 2.23 (s, 3 H ) 2.39 (s, 3 H ) 3.45 (br. s., 2 H ) 3.53 (br. s., 2 H ) 4.83 (s, 1 H ) 4.90 (J=9.04 Hz, 2 H ) 5.62 (s, 2 H ) 7.06 (d, J=5.65 Hz, 1 H ) 7.75 (s, 1 H ) 8.07 (s, 1 H ) 8.17 (d, J=5.09 Hz, 1 H ) 8.32 (s, 1H ) 8.79 (s, 1 H ).

Example 28

(R)—N-(2-hydroxypropyl)-1-((6-methoxy-5-methylpyrimidin-4-yl)methyl)-6-methyl-1H-pyrrolo[3,2-b]pyridine-3-carboxamide

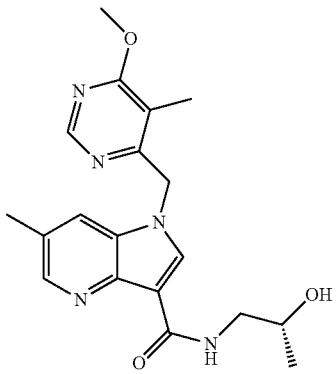 [SMILES: COc1ncnc(Cn2cc(C(=O)NC[C@@H](C)O)c3ncc(C)cc32)c1C]

See FIG. 23(c). 1-((6-methoxy-5-methylpyrimidin-4-yl)methyl)-6-methyl-1H-pyrrolo[3,2-b]pyridine-3-carboxylic acid (75 mg, 0.24 mmol) was taken in a thermal reactor. DCM (5 mL) was added to get a suspension. Added triethyl amine (0.067 mL, 0.48 mmol) followed by the addition of 1-Propanephosphonic acid cyclic anhydride (0.286 mL, 0.48 mmol). (R)-1-aminopropan-2-ol (36.1 mg, 0.48 mmol) was added and stirred at RT for ON. After completion of the reaction, reaction mixture was concentrated and dissolved in DCM:MeOH. This crude compound was subjected for reverse phase purification to obtain (R)—N-(2-hydroxypropyl)-1-((6-methoxy-5-methylpyrimidin-4-yl)methyl)-6-methyl-1H-pyrrolo[3,2-b]pyridine-3-carboxamide (35.0 mg, 39.5%) as a off-white solid. ES+MS m/z: 370 (M+I). $^1$H NMR (300 MHz, DMSO-d6) δ ppm 1.10 (d, J=5.84 Hz, 3 H ) 2.24 (s, 3 H ) 2.39 (s, 3 H ) 3.16-3.29 (m, 1 H ) 3.37-3.48 (m, 1 H ) 3.77 (br. s., 1H ) 3.93 (s, 3 H ) 4.85 (d, J=4.33 Hz, 1 H ) 5.63 (s, 2 H ) 7.74 (s, 1 H ) 8.12 (s, 1 H ) 8.33 (s, 1 H ) 8.41 (s, 1 H ) 8.82 (br. s., 1 H ).

Example 29

1-((6-(dimethylamino)-5-methylpyrimidin-4-yl)methyl)-N-(2-fluoroethyl)-6-methyl-1H-pyrrolo[3,2-b]pyridine-3-carboxamide

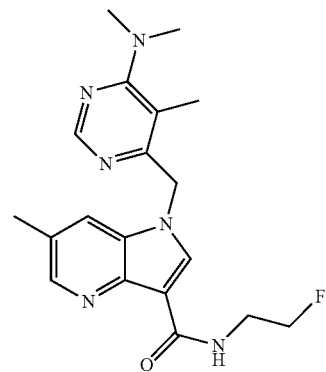 [SMILES: Cc1cnc2c(C(=O)NCCF)cn(Cc3ncnc(N(C)C)c3C)c2c1]

See FIG. 23(d). 1-((6-(dimethylamino)-5-methylpyrimidin-4-yl)methyl)-6-methyl-1H-pyrrolo[3,2-b]pyridine-3-carboxylic acid (75 mg, 0.23 mmol) was taken in a thermal reactor. DCM (5 mL) was added to get a suspension. Triethyl amine (0.064 mL, 0.46 mmol) was added followed by the addition of 1-Propanephosphonic acid cyclic anhydride (0.274 mL, 0.46 mmol). 2-fluoroethanamine hydrochloride (22.94 mg, 0.23 mmol) was added and stirred at RT for ON. After the completion of the reaction, reaction mixture was concentrated and dissolved in DCM:MeOH. This crude compound was subjected for reverse phase purification. The final compound obtained 1-((6-(dimethylamino)-5-methylpyrimidin-4-yl)methyl)-N-(2-fluoroethyl)-6-methyl-1H-pyrrolo[3,2-b]pyridine-3-carboxamide (12.00 mg, 14.05%) as a white solid. ES+MS m/z: 371 (M+). $^1$H NMR (300 MHz, DMSO-d6) δ ppm 2.27 (s, 3 H ) 2.40 (s, 3 H ) 2.95 (s, 6 H ) 3.66 (d, J=5.46 Hz, 1 H ) 3.75 (d, J=5.27 Hz, 1 H ) 4.49 (t, J=4.99 Hz, 1 H ) 4.65 (t, J=4.99 Hz, 1 H ) 5.54 (s, 2 H ) 7.75 (s, 1 H ) 8.13 (s, 1 H ) 8.22 (s, 1 H ) 8.34 (s, 1 H ) 8.88 (t, J=5.84 Hz, 1 H ).

Example 30

N-(2,2-difluoroethyl)-1-((6-methoxy-5-methylpyrimidin-4-yl)methyl)-6-methyl-1H-pyrrolo[3,2-b]pyridine-3-carboxamide

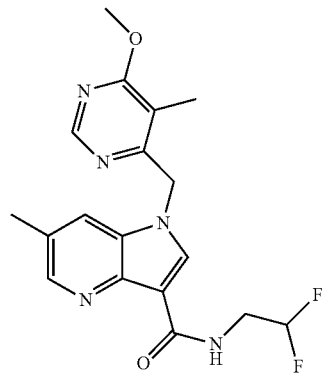 [SMILES: COc1ncnc(Cn2cc(C(=O)NCC(F)F)c3ncc(C)cc32)c1C]

See FIG. 24(a). 1-((6-methoxy-5-methylpyrimidin-4-yl)methyl)-6-methyl-1H-pyrrolo[3,2-b]pyridine-3-carboxylic acid (100 mg, 0.32 mmol) was taken in a thermal reactor. DCM (3 mL) was added to get a suspension. Triethyl amine (0.089 mL, 0.64 mmol) was added followed by the addition of 1-Propanephosphonic acid cyclic anhydride (0.381 mL, 0.64 mmol). 2,2-difluoroethanamine (26.0 mg, 0.32 mmol) was added and stirred at RT for ON. After the completion of the reaction, reaction mixture was concentrated and dissolved in DCM:MeOH. This crude compound was subjected for reverse phase purification to obtain N-(2,2-difluoroethyl)-1-((6-methoxy-5-methylpyrimidin-4-yl)methyl)-6-methyl-1H-pyrrolo[3,2-b]pyridine-3-carboxamide (20.00 mg, 16.64%) as a off white solid. ES+MS m/z: 376 (M-1). $^1$H NMR (300 MHz, DMSO-d6) δ ppm 2.24 (s, 4 H ) 2.40 (s, 3 H ) 3.77-3.89 (m, 2 H ) 3.93 (s, 4 H) 5.65 (s, 2 H ) 7.77 (s, 1 H ) 8.20 (s, 1 H ) 8.40 (s, 1 H ) 8.36 (s, 1 H ) 8.91 (br. s., 1 H ).

Example 31

1-(2,4-dimethylbenzyl)-N-(2-fluoroethyl)-1H-pyrrolo[3,2-b]pyridine-3-carboxamide

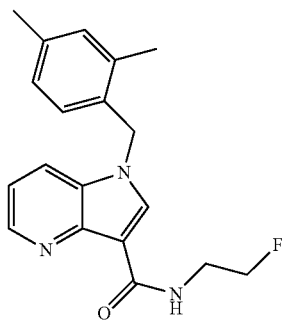 [SMILES: Cc1ccc(Cn2cc(C(=O)NCCF)c3ncccc32)c(C)c1]

See FIG. 24(b). 1-(2,4-dimethylbenzyl)-1H-pyrrolo[3,2-b]pyridine-3-carboxylic acid (200 mg, 0.71 mmol) was taken in a 100 ml single necked flask equipped with an air condenser connected to nitrogen source. Added CH$_2$Cl$_2$ (10 mL) to get a clear solution. Triethylamine (5 mL, 35.87 mmol) was added followed by the addition of 1-Propylphosphonic acid cyclic anhydride (2 mL, 1.43 mmol) and 2-Fluoroethylamine hydrochloride (142 mg, 1.43 mmol). The reaction mass was stirred at RT for overnight. This crude compound was subjected for reverse phase purification to obtain 1-(2,4-dimethylbenzyl)-N-(2-fluoroethyl)-1H-pyrrolo[3,2-b]pyridine-3-carboxamide (50.00 mg, 22%) as a off white solid. ES+MS m/z: 326 (M+1). $^1$H NMR (300 MHz, DMSO-d6) δ ppm 2.21 (s, 3 H ) 2.24 (s, 3 H ) 3.57-3.86 (m, 2 H ) 4.50 (t, J=4.99 Hz, 1 H ) 4.66 (t, J=4.99 Hz, 1 H ) 5.41-5.60 (m, 2 H ) 6.72 (d, J=7.72 Hz, 1 H ) 6.94 (d, J=7.54 Hz, 1 H ) 7.05 (s, 1 H ) 7.28 (dd, J=8.29, 4.71 Hz, 1 H ) 7.98 (dd, J=8.38, 1.04 Hz, 1 H ) 8.13 (s, 1 H ) 8.51 (dd, J=4.62, 1.04 Hz, 1 H ) 8.94 (t, J=5.84 Hz, 1 H ).

Example 32

N-(cyclopropylmethyl)-1-(2-fluoro-6-methoxybenzyl)-1H-pyrrolo[3,2-b]pyridine-3-carboxamide

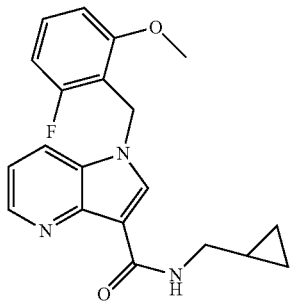 [SMILES: COc1cccc(F)c1Cn1cc(C(=O)NCC2CC2)c2ncccc21]

See FIG. 24(c). In a 50 mL round-bottomed flask 1-(2-fluoro-6-methoxybenzyl)-1H-pyrrolo[3,2-b]pyridine-3-carboxylic acid (0.130 g, 0.43 mmol), cyclopropylmethanamine (0.040 g, 0.56 mmol) and TEA (0.181 mL, 1.30 mmol) was taken DCM (10 mL) under N2. To this 1-Propanephosphonic acid cyclic anhydride (0.317 g, 1.00 mmol) was added. The resulting reaction was stirred at RT for 50 min. LCMS analysis showed formation of required product. Reaction was diluted with DCM and water. DCM layer was extracted and washed with brine and dried over sodium sulphate and concentrated. Purification was done on Waters RP system to get product N-(cyclopropylmethyl)-1-(2-fluoro-6-methoxybenzyl)-1H-pyrrolo[3,2-b]pyridine-3-carboxamide (0.060 g, 39.2%). ES+MS m/z: 354 (M+1). $^1$H NMR (300 MHz, DMSO-d6) δ ppm 0.24 (q, J=4.90 Hz, 2 H ) 0.38-0.50 (m, 2 H ) 1.03 (t, J=7.06 Hz, 1H ) 3.25 (t, J=6.22 Hz, 2 H) 3.88 (s, 3 H ) 5.47 (s, 2 H ) 6.83-6.99 (m, 2 H ) 7.26-7.46 (m, 2 H ) 8.02 (s, 1H ) 8.07 (d, J=8.10 Hz, 1 H ) 8.49 (d, J=3.96 Hz, 1 H ) 8.75 (t, J=5.65 Hz, 1 H ).

Example 33

N-(2,2-difluoroethyl)-1-((6-methoxy-5-methylpyrimidin-4-yl)methyl)-6-methyl-1H-pyrrolo[3,2-b]pyridine-3-carboxamide ES+MS m/z: 376
$^1$H NMR (300 MHz, DMSO-d6) δ ppm 2.18-2.31 (m, 3 H ) 2.40 (s, 3H ) 3.84-3.97 (m, 5 H ) 5.62-5.70 (m, 2 H ) 6.01-6.22 (tt, 1 H ) 7.78 (s, 1 H ) 8.20 (s, 1 H ) 8.38-8.41 (d, J=14.51 Hz, 2 H ) 8.87-8.96 (m, 1 H ).

Example 34

1-((6-(dimethylamino)-5-methylpyrimidin-4-yl)methyl)-N-(2-hydroxy ethyl)-6-methyl-1H-pyrrolo[3,2-b]pyridine-3-carboxamide ES+MS m/z: 369
$^1$H NMR (300 MHz, DMSO-d6) δ ppm 2.27 (s, 3 H ) 2.40 (s, 3 H ) 2.95 (s, 6 H ) 3.41-3.58 (m, 4 H ) 4.84 (t, J=4.99 Hz, 1 H ) 5.53 (s, 2 H ) 7.73 (s, 1 H ) 8.10 (s, 1 H ) 8.22 (s, 1 H ) 8.33 (s, 1 H ) 8.80 (t, J=5.46 Hz, 1 H ).

Example 35

1-((6-(Difluoromethoxy)-5-methylpyrimidin-4-yl)methyl)-N-(2-hydroxyethyl)-6-methyl-1H-pyrrolo[3,2-b]pyridine-3-carboxamide ES+MS m/z: 392
$^1$H NMR (400 MHz, DMSO-d6) δ ppm 2.32 (s, 3H), 2.40 (s, 3H), 3.46 (d, J=5.6 Hz, 2H), 3.56 (d, J=5.1 Hz, 2H), 5.75 (s, 2H), 4.83 (brs, 1H), 8.02-7.53 (m, 2H), 8.21-8.04 (m, 1H), 8.35 (s, 1H), 8.52 (s, 1H), 8.81 (br s, 1H).

Example 36

N-(2-fluoroethyl)-6-methoxy-1-((6-methoxy-5-methylpyrimidin-4-yl)methyl)-1H-pyrrolo[3,2-b]pyridine-3-carboxamide ES+MS m/z: 374
$^1$H NMR (300 MHz, DMSO-d6) δ ppm 2.14-2.32 (m, 3 H ) 3.64-3.86 (m, 5 H ) 3.94 (s, 3 H ) 4.49 (t, J=4.99 Hz, 1 H ) 4.65 (t, J=4.90 Hz, 1 H ) 5.64 (s, 2 H ) 7.63 (d, J=2.45 Hz, 1 H) 8.07 (s, 1 H ) 8.26 (d, J=2.45 Hz, 1 H ) 8.43 (s, 1 H ) 8.76 (t, J=5.93 Hz, 1 H ).

Example 37

N-(2,2-difluoroethyl)-6-methoxy-1-((6-methoxy-5-methylpyrimidin-4-yl)methyl)-1H-pyrrolo[3,2-b]pyridine-3-carboxamide ES+MS m/z: 392
$^1$H NMR (300 MHz, DMSO-d6) δ ppm 2.18-2.31 (m, 3 H ) 3.77-3.97 (m, 8 H ) 5.62-5.69 (m, 2 H ) 6.00-6.38 (tt, 1 H ) 7.64 (d, J=2.45 Hz, 1 H ) 8.11 (s, 1 H ) 8.27 (d, J=2.45 Hz, 1 H ) 8.43 (s, 1 H ) 8.74-8.84 (m, 1 H ).

Example 38

N-(2-hydroxyethyl)-6-methoxy-1-((6-methoxy-5-methylpyrimidin-4-yl)methyl)-1H-pyrrolo[3,2-b]pyridine-3-carboxamide ES+MS m/z: 372
$^1$H NMR (300 MHz, DMSO-d6) δ ppm 2.23 (s, 3 H ) 3.31-3.43 (m, 4 H ) 3.81 (s, 3 H ) 3.94 (s, 3 H ) 4.83 (t, J=4.99 Hz, 1 H ) 5.63 (s, 2 H ) 7.61 (d, J=2.45 Hz, 1 H ) 8.03 (s, 1 H ) 8.25 (d, J=2.45 Hz, 1 H ) 8.43 (s, 1 H ) 8.64-8.74 (m, 1 H ).

Example 39

1-((6-(Dimethylamino)-5-methylpyrimidin-4-yl)methyl)-N-(2-fluoroethyl)-6-methoxy-1H-pyrrolo[3,2-b]pyridine-3-carboxamide ES+MS m/z: 387
$^1$H NMR (400 MHz, DMSO-d6) δ ppm 2.28 (s, 3H), 2.96 (s, 6H), 3.67 (q, J=5.2 Hz, 1H), 3.74 (q, J=5.4 Hz, 1H), 3.83 (s, 3H), 4.51 (t, J=5.0 Hz, 1H), 4.63 (t, J=5.0 Hz, 1H), 5.55 (s, 2H), 7.62 (d, J=2.4 Hz, 1H), 8.05 (s, 1H), 8.27-8.25 (m, 2H), 8.77 (t, J=6.0 Hz, 1H).

Example 40

N-(2,2-Difluoroethyl)-1-((6-(dimethylamino)-5-methylpyrimidin-4-yl)methyl)-6-methoxy-1H-pyrrolo[3,2-b]pyridine-3-carboxamide ES+MS m/z: 405
$^1$H NMR (400 MHz, DMSO-d6) δ ppm 2.27 (s, 3H), 2.95 (s, 6H), 4.00-3.84 (m, 5H), 5.55 (s, 2H), 6.32-6.04 (m, 1H), 7.62 (d, J=2.3 Hz, 1H), 8.08 (s, 1H), 8.27-8.24 (m, 2H), 8.79 (t, J=6.0 Hz, 1H).

Example 41

1-((6-(Dimethylamino)-5-methylpyrimidin-4-yl)methyl)-N-(2-hydroxyethyl)-6-methoxy-1H-pyrrolo[3,2-b]pyridine-3-carboxamide ES+MS m/z: 385
$^1$H NMR (400 MHz, DMSO-d6) δ ppm 2.28 (s, 3H), 2.96 (s, 6H), 3.46-3.43 (m, 2H), 3.55-3.54 (m, 2H), 3.82 (s, 3H), 4.82 (br. s., 1H), 5.54 (s, 2H), 7.60 (d, J=2.4 Hz, 1H), 8.01 (s, 1H), 8.37-8.17 (m, 2H), 8.69 (t, J=5.7 Hz, 1H).

Example 42

1-((6-(Difluoromethoxy)-5-methylpyrimidin-4-yl)methyl)-N-(2-fluoroethyl)-6-methoxy-1H-pyrrolo[3,2-b]pyridine-3-carboxamide ES+MS m/z: 410
$^1$H NMR (400 MHz, DMSO-d6) δ ppm 2.31 (s, 3H), 3.68-3.67 (m, 1H), 3.77-3.71 (m, 1H), 3.82 (s, 3H), 4.52 (t, J=4.9 Hz, 1H), 4.64 (t, J=4.9 Hz, 1H), 5.75 (s, 2H), 7.99-7.63 (m, 2H), 8.09 (s, 1H), 8.27 (d, J=2.2 Hz, 1H), 8.54 (s, 1H), 8.78 (t, J=5.7 Hz, 1H).

Example 43

N-(2,2-Difluoroethyl)-1-((6-(difluoromethoxy)-5-methylpyrimidin-4-yl)methyl)-6-methoxy-1H-pyrrolo[3,2-b]pyridine-3-carboxamide ES+MS m/z: 428
$^1$H NMR (400 MHz, DMSO-d6) δ ppm 2.32 (s, 3H), 3.90-3.82 (m, 5H), 5.76 (s, 2H), 6.34-6.05 (m, 1H), 7.99-7.63 (m, 2H), 8.13 (s, 1H), 8.29 (d, J=2.4 Hz, 1H), 8.81 (t, J=6.2 Hz, 1H), 8.54 (s, 1H), 8.81 (t, J=6.2 Hz, 1 H).

Example 44

1-((6-(difluoromethoxy)-5-methylpyrimidin-4-yl)methyl)-N-(2-hydroxyethyl)-6-methoxy-1H-pyrrolo[3,2-b]pyridine-3-carboxamide ES+MS m/z: 408
$^1$H NMR (400 MHz, DMSO-d6) δ ppm 2.30 (s, 3H), 3.46-3.42 (m, 2H), 3.56-3.52 (m, 2H), 3.82 (s, 3H) 4.81 (t, J=5.0 Hz, 1H), 5.73 (s, 2 H), 7.97-7.61 (m, 2H), 8.04 (s, 1H), 8.25 (d, J=2.3 Hz, 1H), 8.53 (s, 1H), 8.69 (t, J=5.6 Hz, 1H).

Example 45

1-((3,5-dimethylpyrazin-2-yl)methyl)-N-(2-fluoroethyl)-6-methyl-1H-pyrrolo[3,2-b]pyridine-3-carboxamide ES+MS m/z: 342
$^1$H NMR (300 MHz, DMSO-d6) δ ppm 2.40 (d, J=0.94 Hz, 6 H ) 2.58 (s, 4 H ) 3.63-3.70 (m, 1 H ) 3.75 (q, J=5.53 Hz, 1 H ) 4.49 (t, J=4.99 Hz, 1 H ) 4.65 (t, J=5.18 Hz, 1 H ) 5.67 (s, 2 H ) 7.75-7.79 (m, 1 H ) 8.12-8.17 (m, 2 H ) 8.33-8.37 (m, 1 H ) 8.87 (t, J=5.93 Hz, 1 H ).

Example 46

N-(2,2-difluoroethyl)-1-((3,5-dimethylpyrazin-2-yl)methyl)-6-methyl-1H-pyrrolo[3,2-b]pyridine-3-carboxamide ES+MS m/z: 360
$^1$H NMR (300 MHz, DMSO-d6) δ ppm 2.39 (s, 6 H ) 2.58 (s, 3 H ) 3.76-3.95 (m, 2 H) 5.68 (s, 2 H ) 5.98-6.05 (m, 1 H ) 6.15-6.22 (m, 1 H ) 6.35-6.40 (m, 1 H ) 7.78 (s, 1 H ) 8.14 (s, 1 H ) 8.19 (s, 1 H ) 8.36 (s, 1 H ) 8.85-8.97 (m, 1 H ).

Minimal Inhibitory Concentration (MIC) and Minimal Bactericidal Concentration (MBC)

*Mycobacterium tuberculosis* (Mtb) H37Rv ATCC 27294 used for MIC determination was grown as reported in Jayaram et. al. (2003). The inoculum used for all the experiments was derived from a single seed lot that had been maintained at −70° C. Briefly, Mtb was grown in roller bottles at 37° C. for 7 to 10 days in Middlebrook 7H9 broth supplemented with 0.2% glycerol, 0.05% Tween 80 (Sigma), and 10% albumin dextrose catalase (Difco Laboratories, Detroit, Mich.); referred to as 7H9 broth in the remainder of the document. The cells were harvested by centrifugation, washed twice in 7H9 broth, and resuspended in fresh 7H9 broth. Aliquots of 0.5 ml were dispensed, and the seed-lot suspensions were stored at −70° C. After 24 hours at −70° C., one vial was thawed and plated for colony forming unit (CFU) enumeration. All test compound stocks and dilutions were prepared in DMSO.

Mtb MICs of test compounds were determined in 7H9 broth by a standard microdilution method (Balganesh et. al. 2010) with some modifications. Briefly, 1 µl of serial two-fold dilutions of test compound were put in 384 well plate, with the final concentrations ranging from 100 µM-0.19 µM. Control wells included media and culture controls. 40 µl (3–7× $10^5$ CFU/ml) of the bacterial culture was added to all the wells except the media control wells. The plates were packed in gas permeable polythene bags and incubated at 37° C. for 5 days. Following this incubation period, 8 µl of a freshly prepared 1:1 mixture of Resazurin (0.020% in water), and 10% Tween 80 was added to all the wells. The plates were re-incubated for an additional 24 hours at 37° C. and the colour conversion of all wells recorded. A blue colour in the well was interpreted as no growth, and a pink colour was scored as growth. Minimum Inhibitory Concentration (MIC) was defined as the lowest drug concentration which prevented the colour change from blue to pink. Absorbance at 575 nm & 610 nm was monitored and their ratio calculated. The least concentration which yielded 80% inhibition was considered as MIC. Isoniazid is used as reference drug for this assay.

Aliquots from sample wells (MIC and higher) from the MIC plates were diluted 1:10 and plated on 7H10 agar plates. Plates were incubated at 37° C. for 3-4 weeks, CFU was enumerated. The least compound concentration that resulted in a reduction of two $\log_{10}$ CFU from the start CFU was considered as MBC.

MIC for Drug Sensitive and Single Drug Resistant *M. tuberculosis* Isolates

This assay was set up using the same protocol as above, however the incubation period was extended to 2-3 weeks. Cell growth was monitored by turbidometrically and the least concentration which showed no growth was identified as MIC. With the single drug resistant strains, the respective resistance marker drug was included as positive control.

Method for MIC Determination for Other Bacteria (Gram Positives & Gram Negatives):

MIC values for different bacterial strains (*Staphylococcus aureus* ARC517, *Streptococcus pneumoniae* ARC548, *Haemophilus influenzae* ARC446, *Haemophilus influenzae* ARC158, *Escherichia coli* ARC523, *Escherichia coli* ARC524, *Pseudomonas aeruginosa* ARC545, *P. aeruginosa* ARC546, *Klebsiella pneumoniae* ARC 1865, *Mycobacterium smegmatis* (Msm) ATCC607, Msm mc$^2$155 and *Candida albicans* ARC526 were determined according to Clinical Laboratory Standards Institute (CLSI) guidelines (National Committee for Clinical Laboratory Standards. 2009) using 384 well format in cation adjusted Muller Hinton broth media. Media control, culture control and appropriate reference drug controls were included. Growth is monitored by checking absorbance at 600 nm. Minimum inhibitory concentration (MIC) was taken as the concentration that resulted in a growth inhibition of >80%.

Killing Kinetics in 7H9 Broth and Human THP-1 Macrophages

The killing kinetics assay in 7H9 broth was performed in a 200 µL volume using 96-well plates with Middlebrook 7H9 medium. Serial two-fold dilutions of compounds were made in DMSO separately, with the concentrations ranging from 128 to 0.25 mg/L. From each of these dilutions, 4 µL was added respective wells in a 96-well plate which contained approximately $3 \times 10^7$ CFU/mL of Mtb H37Rv. The plates were incubated at 37° C. and on days 0, 3, 7, 10, 14 aliquots were diluted in Middlebrook 7H9 broth and plated on Middlebrook 7H11 agar plates. Bacterial colonies were enumerated after 21-28 days. Data were expressed as the $\log_{10}$ CFU for each drug treatment.

Intracellular Efficacy of 1,4-Azaindoles in THP-1 Macrophages

THP-1 cells (ATCC) were cultured in 75 cm$^2$ flask to confluence using RPMI 1640 with 10% fetal calf serum (Sigma, St. Louis, Mo.) supplemented with 2 mM L-glutamine. The cells were grown in a 37° C. incubator with 5% CO2 and 95% air till they reach a density of 500,000 cells/mL. From the culture, cells at a density of $1-2 \times 10^5$ cells/mL were infected with *M. tuberculosis* H37Rv at a multiplicity of infection (MOI) of 1:10 (macrophage:bacteria) for 2 hours at 37° C. (batch infection). After 2 hours, the cells were washed twice with pre-warmed phosphate buffered saline to remove extracellular bacteria and then resuspended in complete RPMI11640. Phorbol myristate acetate (Sigma) at 40 nM concentration was used to differentiate the cells to macrophage and were allowed adhere to 96-well plate for 24 hours at 37° C. After 24 hours, varying concentrations of the test compounds are added to the monolayers and incubated for 7 days. The macrophage monolayers were periodically observed under a microscope to monitor adverse changes in the cell morphology due to drug toxicity. At the start of drug treatment and at 7 days post-treatment, the monolayers were gently washed and lysed with 0.04% SDS and plated on Middlebrook 7H11 agar plates. Bacterial colonies were enumerated after 21-28 days. Data were expressed as the $\log_{10}$ CFU for each drug treatment.

Antimicrobial Activity Against Hypoxia Induced Non-Replicating Persistent (NRP) Mtb Cells

*M. tuberculosis* H37Rv cultures were adapted to hypoxic conditions as described in Wayne and Hayes (1996) with minor modifications. Briefly, Mtb cells were grown in Dubos Tween broth in McCartney bottles with a magnetic bead using a defined head-space ratio (HSR) of 0.5. Methylene blue was added as a redox indicator (final concentration of 1.5 µg/mL) to all bottles to monitor oxygen depletion. The MacCartney bottles were placed on a magnetic stirrer set at 180 rpm, inside a 37° C. incubator. The methylene blue indicator started to fade by day 8 and completely decolorized by 12 days. The antimicrobial activity of various compounds against NRP Mtb cells was determined in 96-well microtiter plates using a 14-day old hypoxia adapted culture as described above under the MIC determination section. The entire assay was performed in a hypoxic chamber (DuPoy) by exposing hypoxic cells to varying concentrations of compounds for 7 days at 37° C. An anaerobic indicator strip was placed inside the chamber to visually confirm the removal of oxygen during the entire process. Bacterial enumeration was performed on Middlebrook 7H11 agar plates. Isoniazid and nigericin were used as controls in the assay. Isoniazid showed no reduction in the bacterial CFU even at 10 g/mL concentration indicating a strict NRP state. Data are expressed as the $\log_{10}$ CFU for each drug treatment.

A549 Cytotoxicity

The in vitro cytotoxicity of compounds were measured against A549 human lung carcinoma cells as describedin Eakin et. al (2012). Briefly, A549 cells (ATCC) were grown in RPMI medium (GIBCO-BRL) containing 10% heat-inactivated fetal bovine serum (GIBCO-BRL) and 1 mM L-glutamine (GIBCO-BRL) at a density of 1,000 cells/well. After incubation of the cells with compound in a CO$_2$ atmosphere at 37° C. for 72 hours, cell viability was determined following addition of 10 µM of resazurin solution (Sigma), by measuring fluorescence (excitation at 535 nm, emission at 590 nm) using a fluorimeter. The concentration at which growth is inhibited by 50% is taken as IC$_{50}$ value.

Mutant Generation, Resistance Frequency & Whole Genome Sequencing & Analysis

Generation of Resistant Mutant Strains and Resistance Frequency

Spontaneous resistant mutants were raised against compound 31 & 32 using a single step selection method. Briefly, a mid-logarithmic phase culture of Mtb H37Rv was centrifuged and concentrated 100-fold to achieve a bacterial number of ~$10^{10}$ CFU/mL. Varying dilutions of the bacterial culture were plated onto compound containing plates (concentration corresponding to 4×, 8× and 16×MIC cone. Appropriate dilutions of the bacterial culture were also plated on drug-free Middlebrook 7H11 agar to enumerate the bacterial numbers in the culture. Plates were incubated for 4 weeks at 37° C. and the CFUs in drug-free plates were enumerated. The drug-containing plates were incubated for up to 6 weeks at 37° C. to confirm the final number of spontaneously resistant colonies. The spontaneous rate of resistance was calculated by dividing the number of colonies on drug-containing plates (at a given concentration) divided by the total number of viable bacteria estimated on drug-free plates. Resistant colonies were randomly picked from the drug containing plates and grown in complete 7H9 broth to determine their level of resistance against the specific, compound as well as, other standard TB drugs with different mechanisms of action.

Whole Genome Sequencing

Total DNA for whole genome sequencing was extracted from resistant Mtb cells using standard Phenol-chloroform method. Yield was quantitated on a Qubit 2.0 fluorometer using the dsDNA broad range assay kit (Life Technologies, Grand Island, N.Y.). Library generation was carried out using the Nextera XT DNA sample preparation kit and Nextera XT index primers (Illumina, San Diego, Calif.). The recommended procedure was followed with the following exceptions; a high initial starting concentration of DNA was used and the library normalization step at the end was omitted in favour of qPCR library quantification. qPCR was performed on a BioRad CFX96 cycler using the Kapa BioSytems (Woburm, Mass.) Library quantification kit (KK4824). Libraries where diluted to a standard concentration of 4 nM and 2.5 µl of each sample (8-12 samples depending) were combined and denatured with 1N NaOH (final concentration 0.1N NaOH) for 5 minutes. Sufficient sample was diluted to 600 µl to provide a multiplexed sample of 15-20 pmol. Samples were sequenced on an Illumina MiSeq V2 instrument as 2×150 paired-end single index reads. All sequencing was targeted at ~50-fold coverage.

Assembly and analysis of sequence reads was performed off-instrument using CLCBio Genomics Workbench v 6.0 (Cambridge, Mass.). Fastq files were processed and analyzed as follows; duplicate sequence reads were removed and remaining reads were trimmed for quality and minimum length (50 bp). Reads were then de novo assembled under high stringency (fraction length=0.9, similarity fraction=0.99) using default mismatch/insertion/deletion costs. Detection of SNPs/indels in mutant isolates was accomplished by mapping the processed reads to a reference parent assembly using the same assembly conditions. Quality based SNPs were detected at a minimum frequency of 80% using default criteria. Relevant SNPS/indels were verified by BLAST comparison of the region against the de novo assembly to help eliminate possible errors due to the directed mapping assembly.

Pharmacokinetics (PK) of Azaindole Compounds:

PK of azaindoles compounds was performed in mice (healthy and infected) and rats. Mice were pretreated with 100 mg/kg ABT two hours prior to the compound administration. PK data from healthy mice was used to design the dosing regimen for the efficacy study while, information from infected mice was used for the PK-PD analysis.

BALB/c mice or Wistar rats were administered test compounds 3, 4, 8 and 17 in separate groups, via oral gavage. All oral administration was performed as suspensions in 0.5% HPMC, and 0.1% Tween 80. In a separate groups test compound 3 (0.5 mg/kg) and 17 (2 mg/kg) were administered intravenously as a solution (20% v/v DMA in phosphate buffered saline). All blood samples were collected via sapheneous vein into Microvette CB300® (Starstedt, Germany) tubes coated with Lithium-Heparin, and plasma was prepared from the collected blood by centrifugation.

Single mouse infected POPK: Compounds and reference drugs were formulated in 0.5% HPMC (hydroxypropyl methyl cellulose) and 0.1% Tween80 suspensions. BALB/c mice (3 mice/group) were administered via oral gavage at 50, 100 and 200 mg/kg. Pharmacokinetics was performed on infected mice on $24^{th}$ day of dosing (Rennard, 1986). Blood samples were collected from each mouse at 0.5, 1.5, 3, 5, 7 and 24 hours post compound administration. About 30 µL blood samples were collected by serial sampling from all groups via sapheneous vein into Microvette CB300® (Starstedt, Germany) tubes coated with Lithium-Heparin and plasma (10 µL) was prepared following centrifugation. Plasma samples were stored at −20° C. until analysis using LC-MS/MS.

Epithelial Lining Fluid (ELF) PK:

ELF PK was performed in healthy mice (three mice/group) as described previously (Solapure et. al, 2013) after administration of a single oral dose of 100 mg/kg compound formulated in 0.5% HPMC, and 0.1% Tween 80 suspensions. After 0.5, 1.5, 3, 5, 7, 17 and 24 h of dosing, mice were anesthetized using isoflourane and blood was collected through Retro-Orbital Plexus puncture. Broncho-Alveolar Lavage (BAL) was performed after tracheotomy using 0.7 mL of ice-cold PBS. Urea estimation kit, DIUR-500 (Bioassay Systems, U.S.A) was used for urea estimation in plasma and BAL samples. Volume of ELF was calculated after normalizing the urea concentration in BAL with that of plasma as described in Marry et. al, 2011. Plasma and BAL samples were stored at −20° C. until analysis using LC-MS/MS.

Plasma and BAL Sample Analysis:

One mg/mL stock solution of each compound was prepared in Dimethylsulfoxide (DMSO) and diluted two-fold with acetonitrile. A sixteen point calibration curve was utilized for each analyte, and the standard curves ranged from 0.001 to 40 µg/mL. Plasma/BAL samples were precipitated by adding chilled acetonitrile (1:10 v/v) containing carbamazepine as internal standard (250 ng/mL). Samples were vortexed, and centrifuged at 4000 rpm for 30 min at 10° C. The resulting supernatant was mixed with mobile phase (50% acetonitrile in water with 0.1% formic acid). 10 L of sample was injected on to a liquid chromatographic system (Waters-ACQUTY UPLC) coupled to triple quadrupole mass spectrometer (Waters-ACQUTY-TQD; MS/MS). Samples were acquired in positive ion mode and detected by multiple reaction monitoring (MRM). Concentrations of the analyte were determined from a standard curve obtained by plotting known concentrations of the analyte against peak area ratios (analyte/internal standard peak response).

Healthy and Infected PK Data Analysis:

PK analysis of the plasma concentration-time relationships were performed with WinNonlin *Phoenix* Software (version 6.2; Pharsight, USA). A Non-compartmental analysis program, model 200, was used to calculate PK parameters. The maximum concentration of drug in plasma ($C_{max}$), time to $C_{max}$ ($T_{max}$), elimination half-life ($t_{1/2}$), and AUC from time zero to infinity ($AUC_{0-\infty}$) were estimated. AUC was computed using trapezoidal rule (linear up and log down) and $AUC_{0-\infty}$ value was considered only when AUC extrapolated was not more than 20% of original value. Minimum of three sample points in the terminal slope were used to estimate to calculate half-life.

Analysis of ELF PK

Volume of ELF in the BAL samples was calculated as volume of BAL multiplied by the ratio of urea concentrations in BAL and plasma as described (Solapure et. al, 2013; Marry et. al, 2011) The compound concentration in ELF was calculated by multiplying concentration in BAL samples by the ratio of BAL volume to the ELF volume. AUC0-∞ in plasma and ELF were calculated by Non-compartmental analysis WinNonlin *Phoenix* Software (version 6.2; Pharsight, USA). Free plasma AUC was calculated after multiplying concentrations at each time point by the free fraction in plasma. Lung ELF penetration ratio was calculated as a ratio of $AUC_{0-\infty}$ in ELF to free $AUC_{0-\infty}$ in free plasma/total plasma during the same time interval. This ratio, measured in healthy mice after single dose administration, was assumed to remain constant during multiple dose efficacy study in the infected mice. Sparse sample analysis in WinNonlin was used for estimating standard error (SE) associated with AUC estimate.

In Vivo Efficacy Studies

Mycobacterium Tuberculosis Infection Inoculums:

Mtb H37Rv (ATCC 27294), sensitive to all the standard antimycobacterial agents, was grown as mentioned above. After 7-10 days, cells were harvested by centrifugation, washed twice in 7H9 broth and re-suspended in fresh 7H9 broth. One mL aliquots were dispensed and stored at −70° C. The frozen stocks were thawed on the day of animal infection and used as inoculums.

Ethics Statement and Animals:

All animal experiment protocols and usage was approved by Institutional Animal Ethics Committee (IAEC), registered with the Committee for the Purpose of Control and Supervision (CPCSEA), Government of India. Male BALB/c mice were purchased from RCC Hyderabad, and Rats from Bioneeds, Bangalore, India. Mice and rats (6-8 weeks) 8 were randomly assigned into groups of three or four per cage, and were kept for one week acclimatization before initiating the study. Animals were housed under standard conditions with a 12 hr day-night cycle. Feed (Nutrilab®) and water were given ad libitum. Infected mice were maintained in individually ventilated cages (Allentown Technologies, USA) in biosafety level 3 (BSL-3) facility. All procedures including dosing and blood sampling for pharmacokinetics on infected mice were performed under strict bio-containment.

Aerosol Infection:

Mice and rats were infected with *M. tuberculosis* via inhalation procedure using modified Madison aerosol equipment (Jayaram et. al. 2003). Acute infection model was established by high dose aerosol infection that instilled ~$10^4$ CFU/lung in mice and the drug treatment started three days post infection (Schroeder et. al, 2003; Jayaram et al. 2003). In contrast, the chronic infection model (mice and rats) (Schroeder et. al, 2003; Jayaram et al. 2003; Kumar et al. 2014) was developed with low dose Mtb aerosol infection, that delivered ~50-100 bacilli/lung and the drug treatment started 28 days post infection. Bacterial numbers present in the lungs at the beginning of drug treatment was determined. At the end of the treatment, mice was euthanized, lungs were aseptically removed, and homogenized in 3.0 mL gel saline using Wheaton Teflon-Glass tissue grinders. Lung homogenates were serially diluted in 10-fold steps and plated onto Middlebrook 7H11 agar plates supplemented with 10% ADC. Plates were incubated at 370 C with 5% $CO_2$ for 3 weeks to obtain isolated colonies.

In Vivo Dose-Response Studies in Mice:

Infected mice were pre-treated with daily oral doses of 100 mg/kg of Aminobenzotriazole (ABT) two hours prior to compound administration, to block P450 metabolism enzymes. Azaindole compounds 3 & 4 were formulated in 0.5% (w/v) HPMC and 0.1% Tween 80 (Sigma chemical co. USA) suspensions and delivered by oral gavages. In acute mice model, animals were dosed with 50, 100 mg/kg of compound 3 & 4 and with Isoniazid at 3 mg/kg as a positive control. In chronic model 30 and 100 mg/kg doses of compound 3 & 4 were used. Rifampicin at 10 mg/kg was used as reference drug control. Two separate vehicle control groups with and without ABT were used to rule out any adverse effect of ABT on Mtb infection. All drugs and test compounds were administered orally for four weeks, on a 6/7 day per week dosing format. Forty eight hours after completion of dosing period, animals were euthanized with $CO_2$, lungs were aseptically removed and CFU enumerated following plating as described above.

In Vivo Dose-Response Studies in Rats:

Azaindole compounds 8, 17, 30 & 34 were formulated in 0.5% (w/v) HPMC and 0.1% Tween 80 (Sigma chemical co. USA) suspensions and delivered by oral gavages. In chronic rat model, animals were dosed with 30, 100 mg/kg of compounds 8, 17, 30 & 34. Rifampicin at 10 mg/kg was used as reference drug control. All drugs and test compounds were administered orally for four weeks, on a 6/7 day per week dosing format. Forty eight hours after completion of dosing period, animals were euthanized with $CO_2$, lungs were aseptically removed and CFU enumerated following plating as described above.

Statistical Analysis:

The colony counts obtained from plating were transformed to Log 10 (X+1), where x equals the total number of viable bacilli present in a given sample. Prism software version 4 (Graph Pad Software, Inc., San Diego, Calif.) was used for plotting pharmacodynamic effects. Dunnet's multiple-comparison test was used to differentiate statistical differences in lung CFU in treated versus untreated mice.

Solubility Assay

Solubility of the compounds in 0.1M phosphate buffer, pH 7.4 was determined as described, Glyburide was used as QC standard in the assay. Briefly, compounds were diluted in ACN/water (40:60) to desired concentration, samples were dried using Genevac for 4 hrs and subsequently 800 µl of buffer was added. Compound containing plates were stirred for 24 hrs at 25° C. on Eppendorf Thermomix R at 750 rpm. Finally, compound concentration was estimated using UV and MS analysis.

Plasma Protein Binding Assay

Protein binding is measured using the equilibrium dialysis technique. Compound is added to 10% plasma giving a concentration of 20 µM and dialysed with isotonic buffer for 18 hours at 37° C. The plasma and buffer solutions are analysed using generic LCUVMS and the first apparent binding constant for the compound derived. The binding constant is then used to determine the % free in 100% plasma.

Metabolic Stability Assay (Mouse/Human Microsomal $Cl_{int}$)

1 µM compound was incubated with 1 mg/mL of microsomes (Pooled HLM/MLM with 20 mg/ml protein cone.) at 37° C. in 166 µL of buffer (100 mM phosphate buffer, pH-7.4) containing 2 mM NADPH solution. 20 µL of incubation mix was quenched with 4 volumes chilled acetonitrile at different time points i.e. 0, 2, 5, 10, 20 and 30 min in a fresh 96 well plate. The quench plate was centrifuged at 4000 rpm for 15 min. 30 µL of supernatant was diluted to 300 µL with 50% acetonitrile in water and substrate depletion was analyzed using LC-MS/MS.

Metabolic Stability Assay (Rat/Human Hepatocyte $Cl_{int}$)

Viability of cryopreserved hepatocytes was determined using trypan blue and the cell conc. was adjusted to $10^6$ cells per mL with buffer (KHB buffer). 1 µM compound (in Acetonitrile; 0.01% DMSO) was incubated with 500 µL of hepatocyte cells (1 million cells per mL) in a NUNC plate. Reaction was stopped at different time points (0, 5, 15, 30, 60, 90 and 120 min) by addition of 3 volumes of chilled acetonitrile to 100 µL of reaction mixture and centrifuged at 4° C. for 15 min. Supernatants were analyzed using LC-MS/MS for substrate depletion.

Log D

Octanol-water partition coefficient (Log D) based on the shake-flask principle has been measured as follows. The aqueous solution used was 10 mM sodium phosphate buffer pH 7.4. 20 µL of 10 mM compound dissolved in DMSO was taken in glass vial plate. DMSO was removed using GeneVac. 435 µL of octanol was added using Tomtec, stirred for 5 min to dissolve. Further mixing was done by inversion for 5 h at 25° C., subsequently centrifuged for 30 min at 3000 RPM. LC/UV/APPI/MS quantitation of both aqueous and octanol layers was carried out. Log D value was determined according to the following equation.

$$\mathrm{Log}D = \mathrm{Log}\left(\frac{|\mathrm{Octanol/Octanol}\ inj\ \mathrm{volume}|}{\mathrm{Buffer/Buffer}\ inj\ \mathrm{volume}}\right)$$

The method has been validated for log D ranging from −2 to 5.0.

hERG Assay

Compounds were tested on voltage-gated ion channels using the medium-throughput electrophysiology IonWorks™ device. Detailed methods regarding the running of IonWorks™ have been published (Schroeder 2013). For carrying out the experiment, a boat in the "Cells" position of the IonWorks™ instrument was loaded with the cell suspension, and a 96-well PBS destination plate was placed in the "Plate 1" position. A 384-well PatchPlate™ was placed in the IonWorks™ plenum and held in position using the plenum clamp. From this point the experiment progress is automated and ultimately reports a non-cumulative concentration-effect curve for test compound.

SUMMARY

Figure 1A:
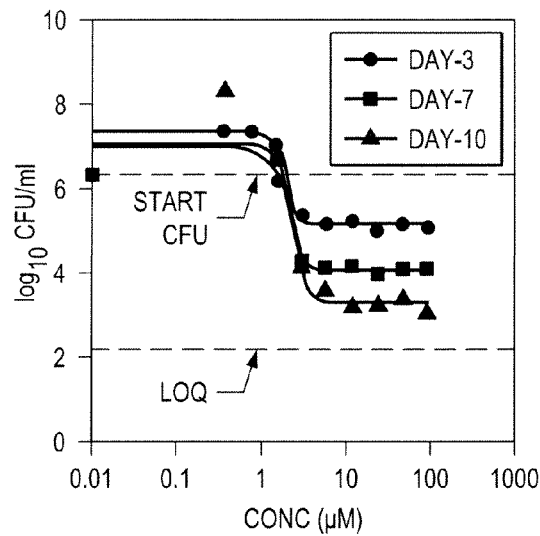
FIG. 1 illustrates the in vitro cell cidality and in vivo efficacy of (a) kinetic of cell cidality for compound 3, (b) kinetic of cell cidality for compound 4, (c) acute efficacy in mouse TB model (d) chronic efficacy in mouse TB model.
Figure 1B:
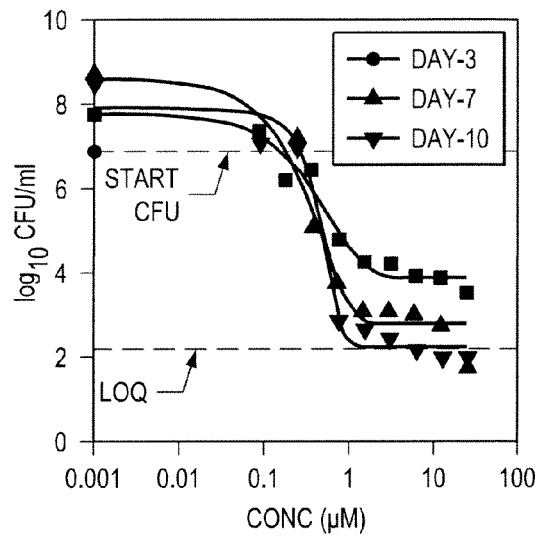
Figure 1C:
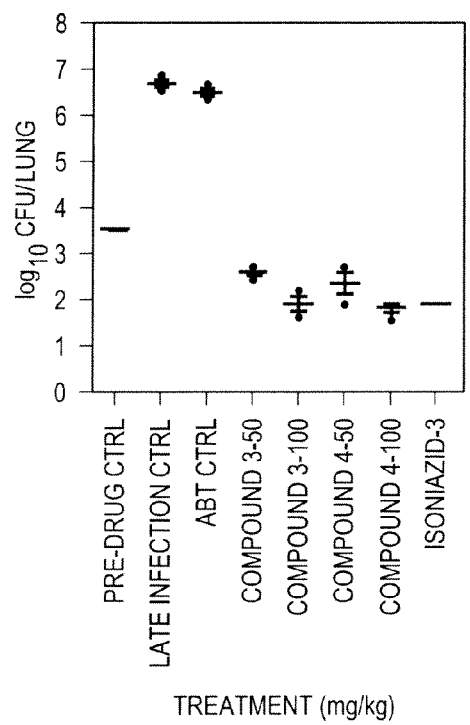
Figure 1D:
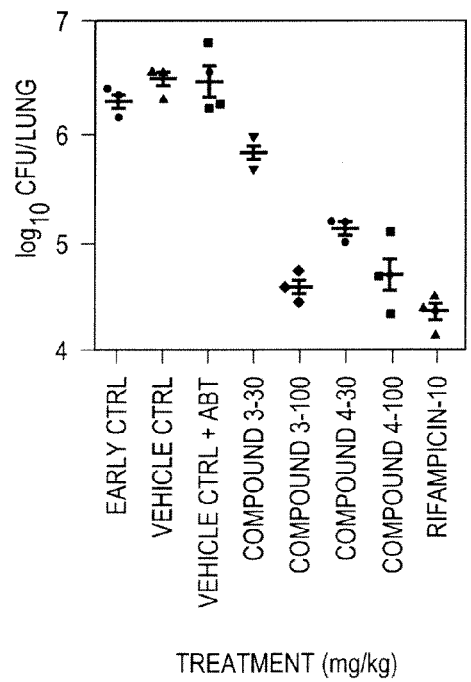
Figure 2:
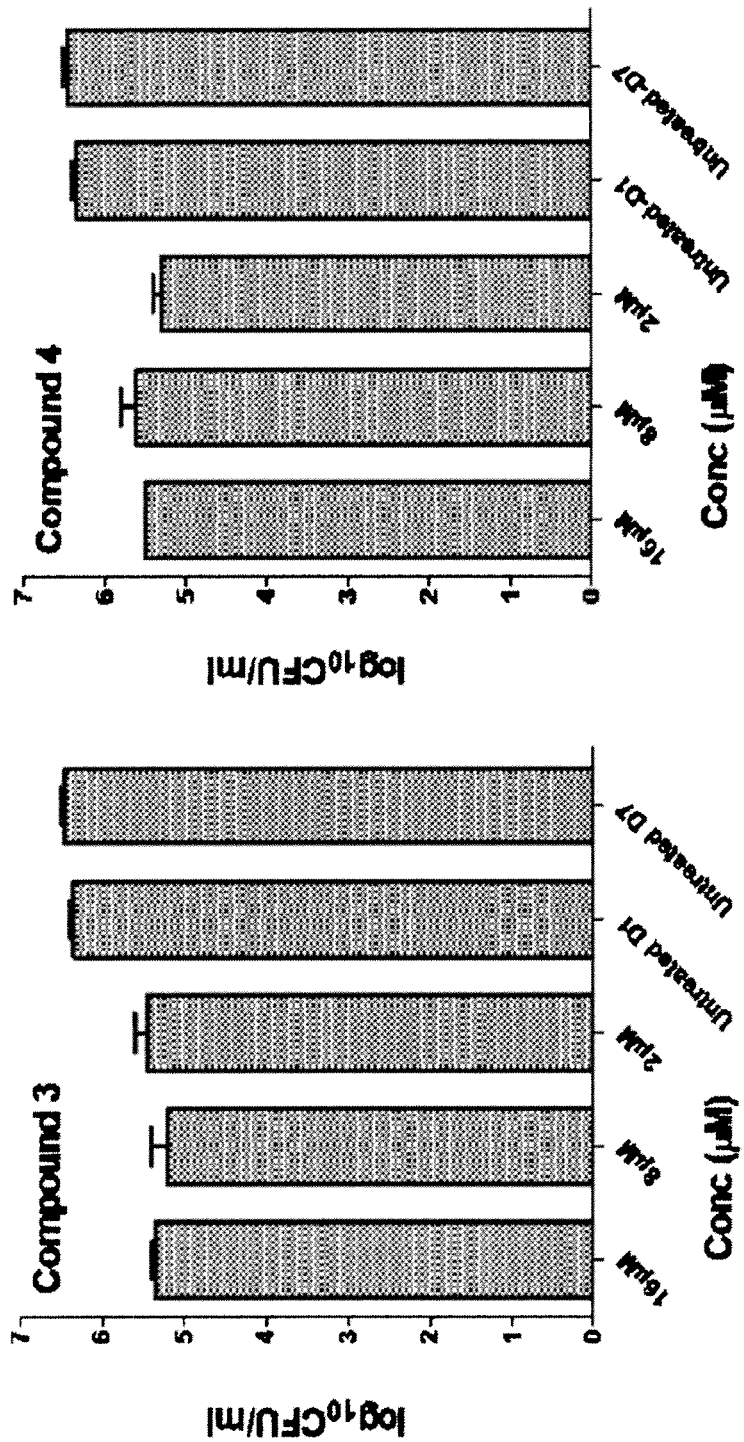
FIG. 2 illustrates the intracellular efficacy of compounds 3 and 4 in THP1 model.

The disclosed compounds, although cidal for Mtb and *Mycobacterium smegmatis* (Msm), did not show activity against broad-spectrum pathogens, thus suggesting excellent target pathogen specificity (Table 2, FIG. 25). The compounds in the series retain MIC for drug sensitive and single drug resistant clinical isolates of Mtb (Table 3, FIG. 26), suggesting their potential for drug sensitive and MDR TB therapy. The compounds exhibited time dependent kill kinetics against replicating Mtb, with ~4 log 10 reductions in colony forming units (CFU) by day 10 at a concentration of 1-4 fold of MIC (FIG. 1). The compounds were also active on intracellular Mtb, with ~1 log 10 reduction in CFU at concentrations 1- to 4-fold greater than the MIC in THP1 cells infected with Mtb (FIG. 2). In addition to their potent activity on replicating bacteria, a subset of molecules in the series show moderate activity against non-replicating Mtb under hypoxic conditions (cidality measured as HBC in Wayne model) represented by compound 3 (Table 4). The compound in the series were found to be non-cytotoxic on A549 human lung adenocarcinoma epithelial cell line post 72 hours treatment (MMIC>100 M, Table 4). We have also observed >95% THP-1 macrophage viability following 7 days of compound exposure at maximum of 32 µM (Table 4).

FIG. 25 shows Table 2, Pathogen specificity.

FIG. 26 shows Table 3, Activity against drug sensitive and drug resistant Mtb.

TABLE 4

Microbiological properties of Compounds

| Compound No | Mtb MIC (µM) | Mtb MBC (µM) | Mtb HBC (µM) | MMIC (A549) (µM) |
|---|---|---|---|---|
| 3 | 1.56-3.12 | 1.56-3.12 | 50 | >100 |
| 4 | 0.39-1.56 | 0.78-1.56 | >100 | >100 |
| 8 | <0.39 | <0.39 | 100 | >100 |
| 17 | 1.56-3.12 | 0.78-1.56 | >100 | >100 |

Spontaneous resistant mutants with reduced susceptibility to 1,4-azaindoles arose at a frequency of $2.9 \times 10^{-9}$ at 8×MIC concentration (Table 5). Whole genome sequencing of the resistant Mtb mutants revealed a single nucleotide change in dprE1 (Rv 3790), resulting in an amino acid substitution at 314 position (Tyr→ His) with no significant secondary target observed. While the compounds in the series were cross-resistant to mutant strain (Tyr314His), resistance was not observed for reference drugs including BTZ043. The cystein387 DprE1 mutations (Cys→ Ser, Cys→ Gly) that impart resistance to BTZ043 (Makarov, V. et al. *Science*, 324, 801-804 (2009), did not show cross resistance to 1,4-azaindoles (Table 6). Furthermore, target specificity was re-confirmed by MIC modulation on over-expression of DprE1, as also seen for BTZ043 (Table 6).

TABLE 5

Resistance frequency

| | Mtb H37Rv MIC (µM) | Mtb H37Rv MBC (µM) | Mtb H37Rv HBC (µM) | MMIC (A549) (µM) |
|---|---|---|---|---|
| Compound 31 | 1.56-3.12 | 3.12-6.25 | 12.5-25 | >82 |
| Compound 32 | 1.56-3.12 | 1.56-6.25 | >200 | >100 |

| | Mtb DprE1 OE MIC (µM) | Mtb DprE1 C387S | Mtb DprE1 C387G MIC (µM) | Mtb DprE1 Y314H MIC (µM) |
|---|---|---|---|---|
| Compound 31 | 25 | 0.78 | 0.78 | 25 |
| Compound 32 | 50 | 0.39 | 0.39 | 200 |

TABLE 6

Cross-resistance within series and reference compounds

| Values in µM | Mtb H37Rv | Mtb DprE1 OE | Mtb DprE1 C387S | Mtb DprE1 C387G | Mtb DprE1 Y314H |
|---|---|---|---|---|---|
| Compound 3 | 3.12 | 50 | 3.12 | 0.78 | >100 |
| Compound 4 | 0.39 | 25 | 0.39 | 0.39 | >200 |

TABLE 6-continued

Cross-resistance within series and reference compounds

| Values in μM | Mtb H37Rv | Mtb DprE1 OE | Mtb DprE1 C387S | Mtb DprE1 C387G | Mtb DprE1 Y314H |
|---|---|---|---|---|---|
| Compound 8 | 0.39 | 6.25 | 0.39 | 0.39 | >200 |
| Compound 17 | 1.56 | 100 | 0.39 | 0.78 | >200 |
| BTZ043 | 0.003 | 50 | >0.1 | >0.1 | 0.0015-0.003 |
| Isoniazid | 0.06 | 0.03 | 0.06 | 0.06 | 0.06 |
| Ethambutol | 2 | 2 | 2 | 4 | 2.0-4.0 |
| Rifampicin | 0.01 | 0.003 | 0.003 | 0.003 | 0.006 |
| TMC207 | 0.6 | 0.15 | 0.3 | 0.15 | 0.15-0.3 |
| Moxifloxacin | 0.125 | 0.06 | 0.06 | 0.06 | 0.06 |
| Ofloxacin | 1 | 0.5 | 0.5 | 0.5 | 0.5 |
| D-cycloserine | 8 | 8 | 8 | 8 | 8.0-16.0 |
| Clofazimine | 0.125 | 0.06 | 0.03 | 0.03 | 0.125 |

The compounds in the series were profiled for in vitro drug metabolism and pharmacokinetics (DMPK) properties, representative compounds are shown in Table 7. The dried DMSO solubility for compounds 3, 4 and 8 was lower than compound 17; the improved solubility may be attributed to hydroxyethyl amide side chain. The protein binding (0% free) values for compounds 3-4, 8 and 17 was between 5% and 22%. The predicted clearance for compounds 3-4, 8 and 17 ranged from 4 to 18° % of liver blood flow (% LBF), estimated by using human microsomes, human hepatocytes and rat hepatocytes. In contrast, the predicted clearance was higher from mouse microsomes (Table 8), suggesting species specific clearance mechanisms. The permeability measured by Caco-2 assay suggested that these compounds are highly permeable with no significant efflux observed. The compounds in the series did not show inhibition of CYP enzymes at 50 μM (Table 7), suggesting their potential for combination therapy. In vitro safety profiling of compounds 3-4, 8 and 17 against a panel of human targets and cardiac channels revealed no major safety liabilities associated with this series (Table 7).

TABLE 7

DMPK and Safety properties of compounds

| | Compound | | | |
|---|---|---|---|---|
| | 3 | 4 | 8 | 17 |
| logD | 2.1 | 3.0 | 2.6 | 1.8 |
| Solubility (μM) | 8[a] | 5[a] | 4[a] | 124 |
| Human CL$_{pred}$ microsomes (% LBF) | 10.4 | 15.6 | 10.1 | 16.1 |
| Human CL$_{pred}$ hepatocytes (% LBF) | 6.0 | 4.3 | 4.3 | 9.2 |
| Rat CL$_{pred}$ hepatocytes (% LBF) | 13 | 13 | 14.9 | 17.9 |
| Human PPB (% free) | 9.8 | 5 | 5 | 22 |
| Caco-2 A-B/B-A (1E−6 · cm/s) | 25/17 | 38/24 | 33/17 | 11/30 |
| CYP[b] inhibition (μM) | >50 | >50 | >50 | >50 |

TABLE 7-continued

DMPK and Safety properties of compounds

| | Compound | | | |
|---|---|---|---|---|
| | 3 | 4 | 8 | 17 |
| hERG (μM) | >33 | >33 | >33 | >33 |
| Secondary pharmacology hits IC$_{50}$ (μM) | No significant hits | | | |

[a]Kinetic solubility in test media >100 μM, [b]: CYP1A2, CYP2C9, CYP2C19, CYP2D6, CYP3A4.

TABLE 8

High intrinsic clearance for mouse microsomes

| | Compound | | | |
|---|---|---|---|---|
| | 3 | 4 | 8 | 17 |
| Mo micrsomal Cl$_{int}$ (μl/min/mg) | 104 | 180 | 108 | 25 |

Figure 3A:
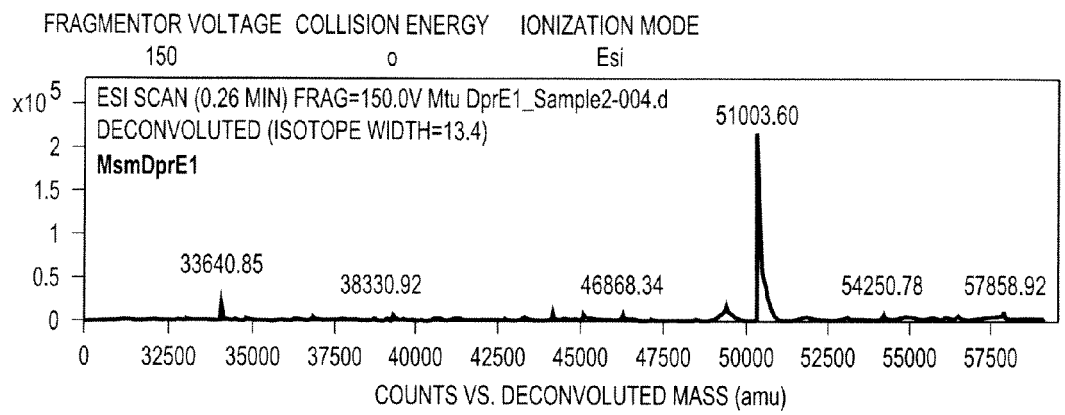
FIG. 3 illustrates mass spectroscopy data of the DprE1 enzyme from *Mycobacterium smegmatis* (a) untreated, (b) treated with BTZ0043, and (c) treated with an inhibitor compound of the present disclosure.
Figure 3B:
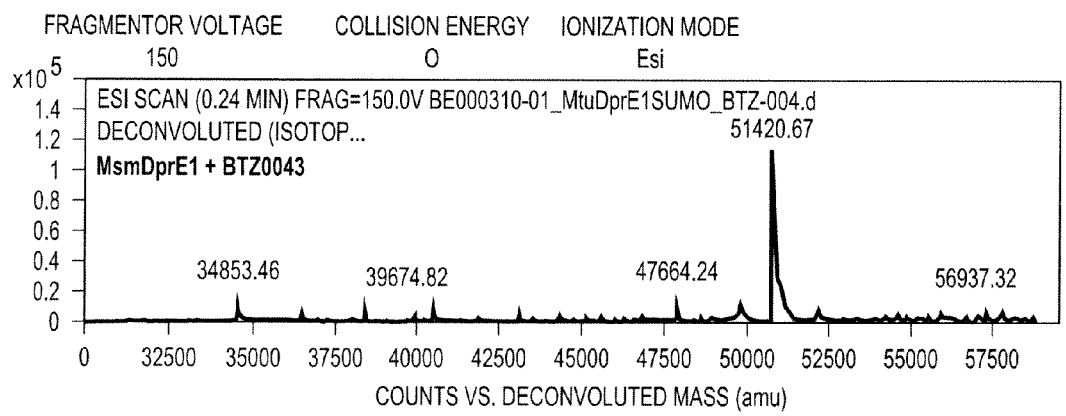
Figure 3C:
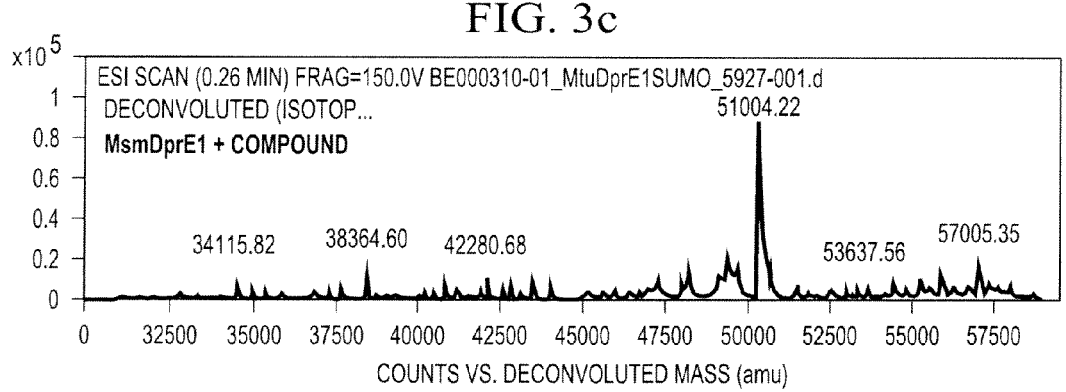

Based on in vitro properties, compounds 3-4, 8 and 17 were profiled for in vivo PK in mouse and rat to assess oral exposures. The PK exposures in mouse were measured in the presence of aminobenzotriazole (ABT), a Pan-inhibitor of CYP isoforms was used to block mouse specific clearance. Significant oral exposures were observed for compounds 3-4, 8 and 17 in both rat and mouse (FIG. 3, Table 9). In the rat, a good correlation was observed between in vitro and in vivo clearance with 92% bioavailability for compound 17 (Table 9). The in vivo efficacy of two representative compounds (3 & 4) was assessed in BALB/c mice in "acute" and "chronic TB models" (Jayaram et al. 2003: Marry et al. 2011; Kumar et al. 2014). In the acute model, treatment was started 3 days post infection, whereas treatment was started on day 28 in the chronic model. Four weeks of treatment of compounds 3 & 4 reduced the bacterial burden in the lungs by >1.5 log 10 CFU and statistically significant dose dependent efficacy was observed (FIG. 1). The oral exposures of compound 3 & 4, assessed from infected animals showed AUCs ranging from 200-700 μM.h and concentrations were maintained above the MIC for ~10 h after each dose (% T>MIC of ~10 hrs), resulting into efficacy in chronic mouse model (FIG. 4; Table 10). Interestingly, the levels of compounds 3 & 4 measured in healthy mouse lung epithelial lining fluid (ELF PK) was comparable to free plasma levels for both the compounds (FIG. 4, Table 11), demonstrating significant exposures at the target site. Thus, a good correlation was observed between plasma and/or ELF levels and pharmacodynamic effect. In the acute and chronic mouse model, the animals tolerated the administered doses for one month, and no adverse effects were observed in terms of body weight and gross pathology.

TABLE 9

Pharmacokinetic parameters of compounds in healthy BALB/c mice and Wistar rats following single dose administration (data are mean ± S.D., n = 3 unless otherwise stated).

| | | Compound | | | |
|---|---|---|---|---|---|
| | | 3 | 4 | 8[a] | 17[b] |
| Mouse POPK (+ABT) | Dose (mg/kg) | 100 | 100 | 30 | 50 |
| | AUC$_{0-\infty}$ (μM · h) | 521.50 ± 19.60 | 346.73 ± 42.75 | 64.19 | 420.30 ± 23.5 |

TABLE 9-continued

Pharmacokinetic parameters of compounds in healthy BALB/c mice and Wistar rats following single dose administration (data are mean ± S.D., n = 3 unless otherwise stated).

|  |  | Compound | | | |
|---|---|---|---|---|---|
|  |  | 3 | 4 | 8[a] | 17[b] |
| Rat IVPK | $T_{max}$ (h) | 6.33 ± 1.15 | 4.67 ± 1.15 | 2 | 1.33 ± 0.58 |
|  | $C_{max}$ (µM) | 66.01 ± 11.17 | 44.12 ± 13.0 | 13.36 | 74.79 ± 15.61 |
|  | $T_{1/2}$ (h) | 1.91 ± 0.11 | 3.63 ± 1.46 | 4.15 | 1.78 ± 0.10 |
|  | Dose (mg/kg) | 0.5 | ND | ND | 2 |
|  | CL (µl/min/kg) | 15.50 ± 3.21 |  |  | 27.35 |
|  | $V_{ss}$ (L/kg) | 1.05 ± 0.28 |  |  | 7.34 |
|  | $AUC_{0-t}$ (µM · h) | 1.60 ± 0.29 |  |  | 3.46 |
|  | $T_{1/2}$ (h) | 2.22 ± 2.51 |  |  | 2.06 |
|  | $C_{0h}$ (µM) | 1.76 ± 0.42 |  |  | 2.64 |
| Rat POPK[c] | Dose (mg/kg) | 30 | 30 | 30 | 20 |
|  | $AUC_{0-\infty}$ (µM · h) | 101.38 | 22.86 | 29.29 | 59.82 |
|  | $T_{max}$ (h) | 2.0 | 3.0 | 4.5 | 0.5 |
|  | $C_{max}$ (µM) | 15.01 | 2.35 | 3.69 | 17.84 |
|  | $T_{1/2}$ (h) | 2.01 | 3.64 | 3.58 | 2.74 |
|  | F | 96% | ND | ND | 100% |

ND: not determined;
[a]compound 5 (n = 2);
[b]compound 6 for Rat IVPK (n = 2);
for all compounds (n = 2)

TABLE 10

ELF penetration ratio of 1,4-aaindoles in healthy BALB/c mice following oral single dose administration (data are mean ± S.D., n = 3 unless otherwise stated).

|  | Compound | | | | | |
|---|---|---|---|---|---|---|
|  | 3 | | | 4 | | |
| Matrix | ELF | Plasma | fPlasma | ELF | Plasma | fPlasma |
| Dose (mg/kg) |  | 100 |  |  | 100 |  |
| $C_{max}$ (µM) | 74.0 ± 3.77 | 63.84 ± 7.37 | 4.85 ± 0.56 | 39.92 ± 13.71 | 38.09 ± 5.86 | 1.52 ± 0.07 |
| $AUC_{0-\infty}$ (h * µM) | 712.85 ± 176.16 | 573.27 ± 78.76 | 43.46 ± 5.96 | 410.37 ± 91.52 | 406.81 ± 44.56 | 12.97 ± 2.78 |
| ELF penetration ratio (based on free plasma AUC)* |  | 7.29-26.10 |  |  | 12.4-50.9 |  |
| ELF penetration ratio (based on total plasma AUC) |  | 0.60-1.97 |  |  | 0.52-1.51 |  |

*calculated based on Hu PPB % free; ELF penetration ratio calculated at 95% confidence interval

TABLE 11

Pharmacokinetic parameters of 1,4-azaindoles in infected BALB/c mice following multiple oral doses (data are mean ± S.D., n = 3 unless otherwise stated).

|  |  | Compound | | | |
|---|---|---|---|---|---|
|  |  | 3 | | 4 | |
| Mouse infected POPK from acute efficacy (+ABT) | Dose (mg/kg) | 50 | 100 | 50 | 100 |
|  | $C_{max}$ (µM) | 17.79 ± 5.61 | 41.28 ± 10.28 | 38.91 ± 15.16 | 72.62 ± 8.31 |
|  | $AUC_{0-\infty}$ (µM * h) | 106.08 ± 3.04 | 332.15 ± 152.51 | 199.62 ± 101.21 | 529.03 ± 85.07 |
|  | $T_{max}$ (h) | 4.33 ± 1.15 | 3.83 ± 2.84 | 4.50 ± 2.78 | 5.67 ± 2.31 |
|  | $T_{1/2}$ (h) | 2.38 ± 0.19 | 3.02 ± 1.99 | 2.23 ± 0.35 | 2.02 ± 0.09 |
|  | % fT > MIC | 23 | 41 | 39 | 50 |
|  | % T > MIC | 58 | 66 | 75 | 83 |
| Mouse infected | Dose (mg/kg) | 30 | 100[a] | 30 | 100[b] |

TABLE 11-continued

Pharmacokinetic parameters of 1,4-azaindoles in infected BALB/c mice following multiple oral doses (data are mean ± S.D., n = 3 unless otherwise stated).

| | | Compound | | | |
|---|---|---|---|---|---|
| | | 3 | | 4 | |
| POPK from chronic efficacy (+ABT) | $C_{max}$ (μM) | 32.78 ± 14.41 | 71.24 | 17.36 ± 1.76 | 43.17 |
| | $AUC_{0-\infty}$ (μM * h) | 251.94 ± 64.01 | 695.76 | 226.98 ± 28.87 | 772.33 |
| | $T_{max}$ (h) | 2.00 ± 0.87 | 3 | 5.67 ± 2.31 | 5 |
| | $T_{1/2}$ (h) | 4.46 ± 0.16 | 4.4 | 3.85 ± 0.54 | 4.21 |
| | % fT > MIC | 29 | 63 | 29 | 100 |
| | % T > MIC | 92 | 100 | 100 | 100 |

[a]compound 3 (n = 2);
[b]compound 4 (n = 1)

TABLE 12

Pharmacokinetic parameters (Mean ± SD) of 1,4-azaindole compounds following multiple oral dose (100 mg/kg) administration in Mtb infected male Wistar rats.

| | Compound | | | |
|---|---|---|---|---|
| | 8 | 17 | 30 | 34 |
| Dose (mg/kg) | | 100 | | |
| $C_{max}$ (μM) | 11.9 ± 3.0 | 46.1 ± 7.7 | 3.4 ± 2.0 | 31.5 ± 3.0 |
| $T_{max}$ (h) | 1.5 ± 0.6 | 5.3 ± 1.2 | 3.3 ± 2.3 | 2.0 ± 0.0 |
| $AUC_{0-\infty}$ (μM * h) | 98.4 ± 31.9 | 986.4 ± 274.3 | 23.3 ± 11.7 | 166.1 ± 43.9 |
| $T_{1/2}$ (h) | 7.2 ± 1.3 | 3.8 ± 0.6 | 3.3 ± 1.1 | 4.6 ± 0.0 |

REFERENCES

Jayaram et. al. *Antimicrob. Agents Chemother.* 47, 2118-2124 (2003).

Balganesh et. al. *Antimicrob. Agents Chemother.* 54, 5167-5172 (2010).

National Committee for Clinical Laboratory Standards. 2009. Volume 29, Number 2. National Committee for Clinical Laboratory Standards, Wayne, Pa.

Wayne and Hayes *Infect. Immun.* 64, 2062-2069 (1996).

Eakin et. al, *Antimicrob. Agents Chemother* 56, 1240-1246 (2012).

Reddy et. al. *Eur. J. Pharm. Sci.* 47, 444-450 (2012).

Louie et. al. *Antimicrob. Agents Chemother.* 53, 3325-30 (2009).

Rennard, S. I. et. al. *J. Appl. Physiol.* 60, 532-538 (1986).

Solapure et. al, *Antimicrob. Agents Chemother.* 57, 2506-2510 (2013).

Marry et. al, *Antimicrob. Agents Chemother.* 55, 1237-1247 (2011).

Schroeder et. al, *J. Biomol. Screen.* 8, 50-64 (2003).

Marry et al. *Antimicrob. Agents Chemother.* 55, 1237-1247 (2011).

Kumar et al. *Tuberculosis.* (2014).

What is claimed is:

1. A compound of formula (I):

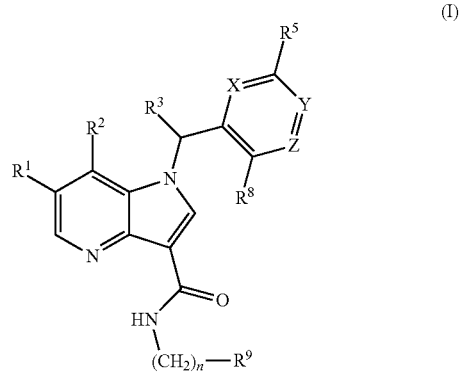

wherein $R^1$ is selected from hydrogen, fluorine, bromine, —$OCH_3$ and methyl;

$R^2$ is hydrogen or methyl;

$R^3$ is hydrogen or methyl;

X is N or $CR^4$;

$R^4$ is selected from hydrogen, fluorine and —$OCH_3$;

$R^5$ is selected from hydrogen, fluorine, —$CF_3$ and —CN;

Y is N or $CR^6$;

$R^6$ is hydrogen or methyl:

Z is N or $CR^7$;

$R^7$ is selected from hydrogen, fluorine, —$OCH_3$, —$OCHF_2$, —$OCH_2CF_3$, and —$N(CH_3)_2$;

$R^8$ is selected from hydrogen, fluorine, methyl and —$OCH_3$;

n is 1 or 2:

$R^9$ is selected from fluorine, cyclopropyl, —$OCH_3$, —OH, —$OCF_3$, $CHF_2$, —CH(F)$CH_3$ and —CH(OH)$CH_3$, or a pharmaceutically acceptable salt thereof.

2. The compound of claim 1, wherein the compound is selected from:

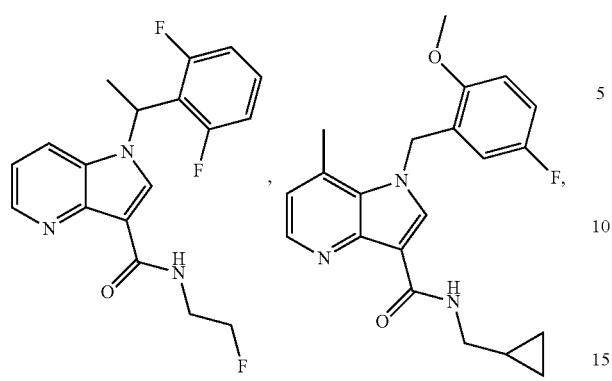
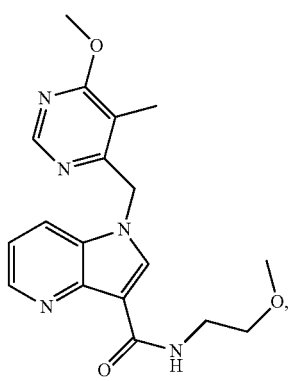
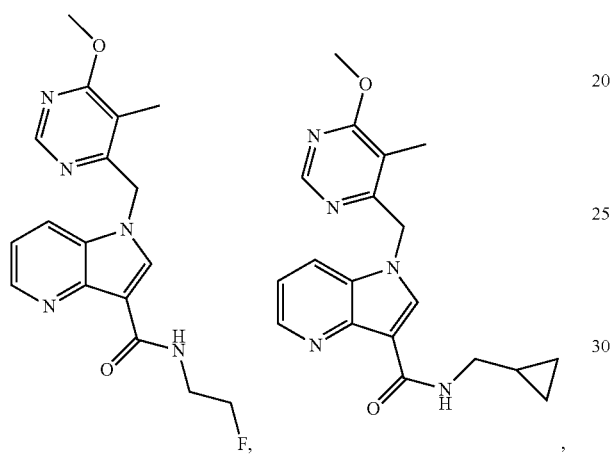
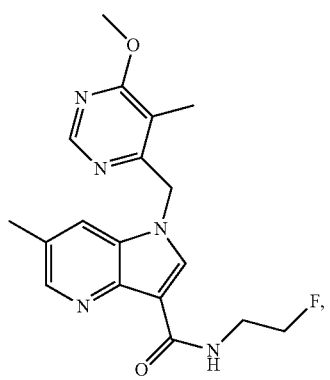
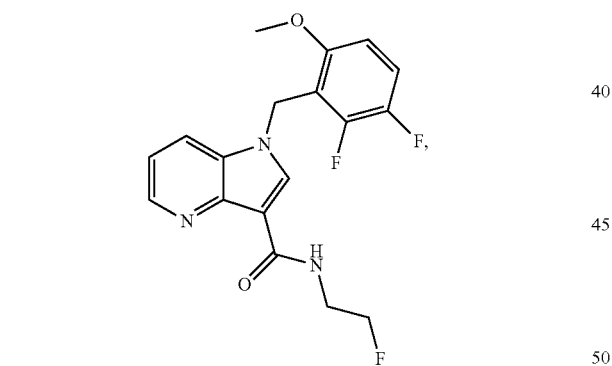
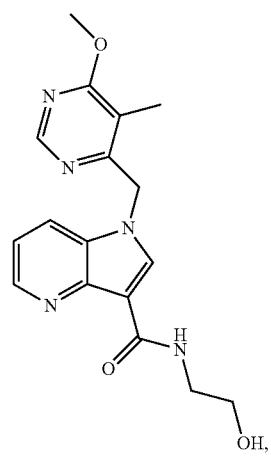
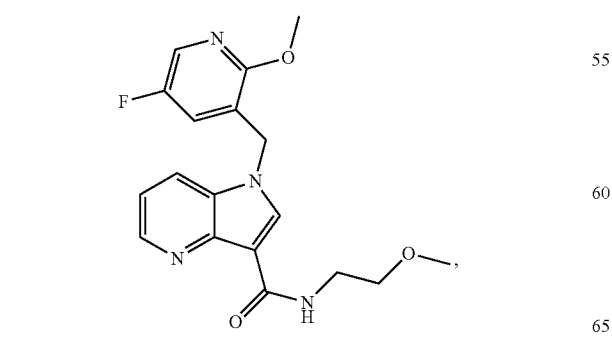
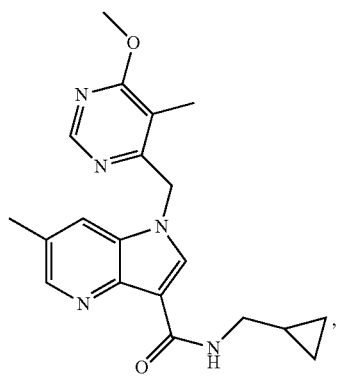

75
-continued
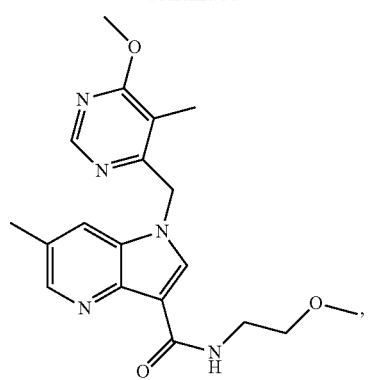
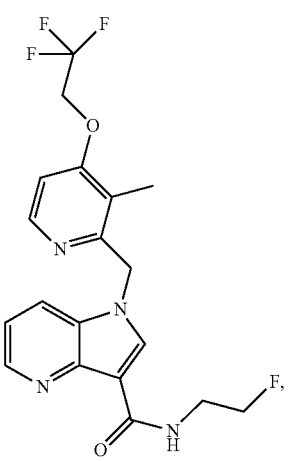
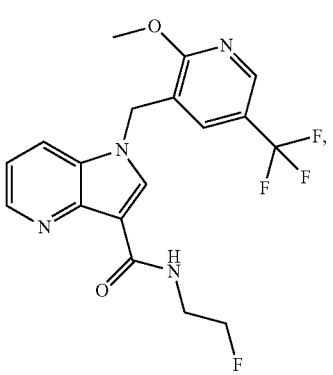
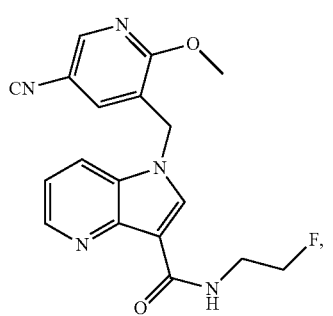
76
-continued
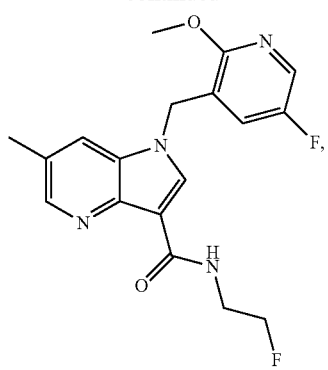
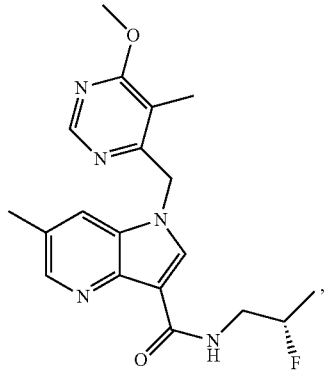
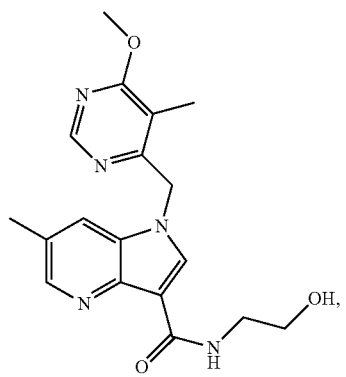
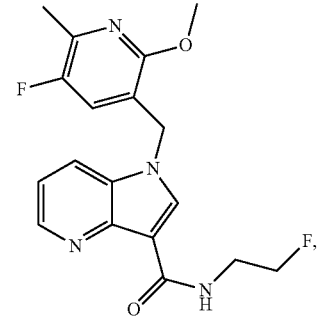

77
-continued

78
-continued

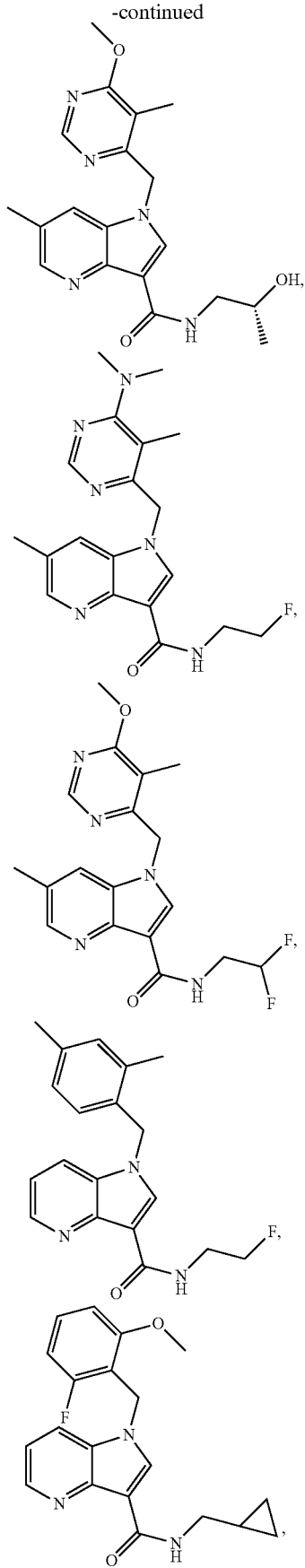
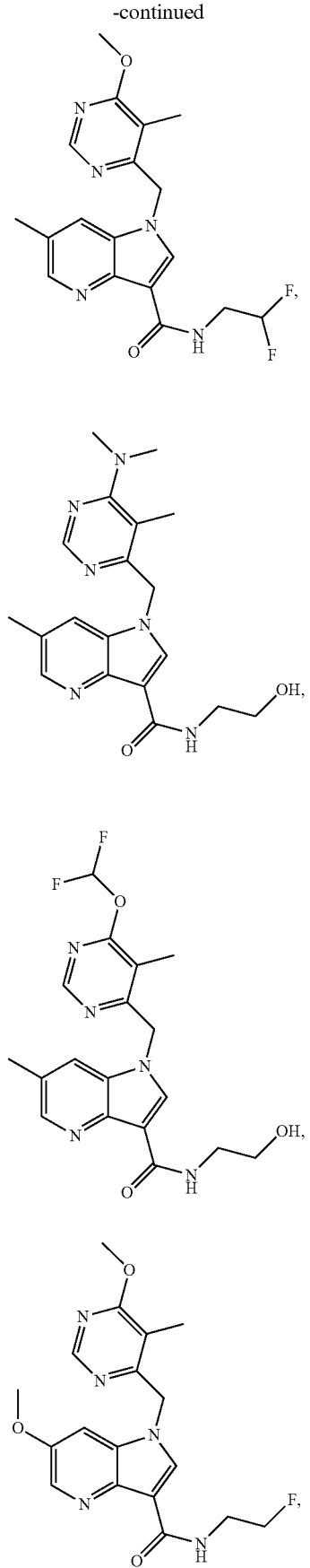

81
-continued
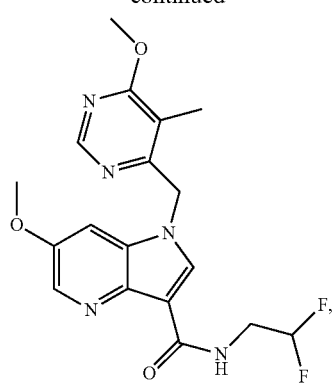
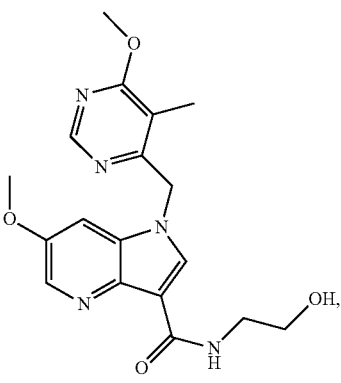
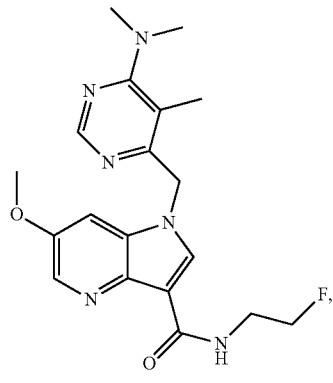
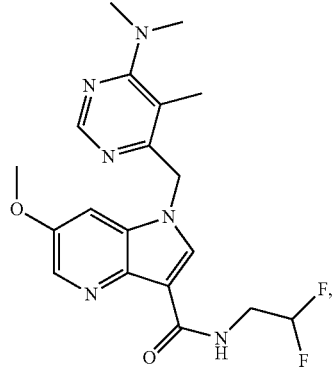
82
-continued
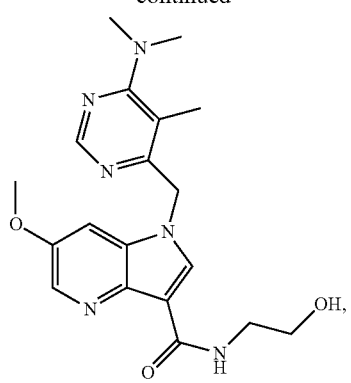
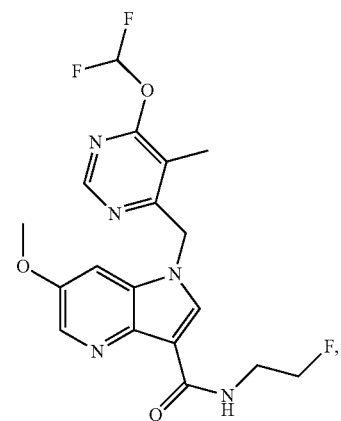
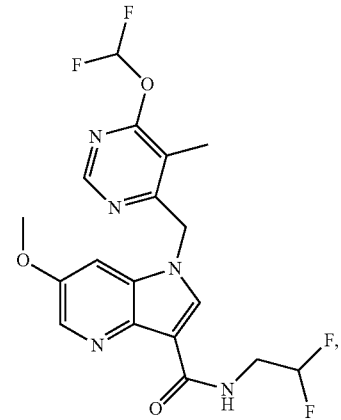
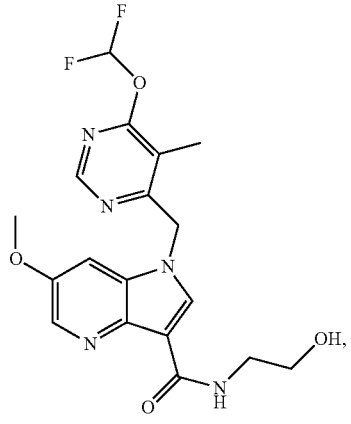

-continued

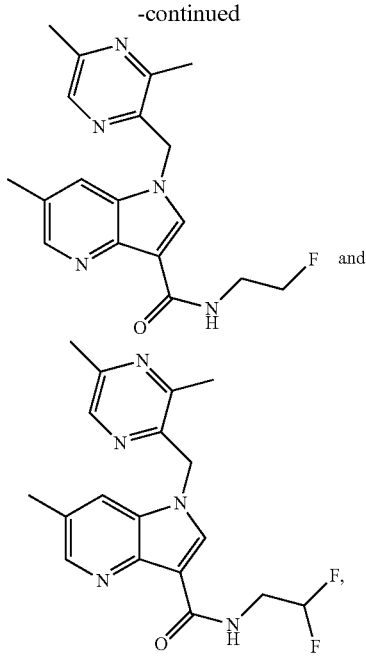

or a pharmaceutically acceptable salt thereof.

3. A pharmaceutical composition comprising a compound of claim 1, or a pharmaceutically acceptable salt thereof, and a pharmaceutically acceptable carrier or diluent.

4. A pharmaceutical composition comprising a compound of claim 2, or a pharmaceutically acceptable salt thereof, and a pharmaceutically acceptable carrier or diluent.

5. A method of treating tuberculosis or a *Mycobacterium* infection comprising administering to a subject in need thereof a therapeutically effective amount of a compound of claim 1, or a pharmaceutically acceptable salt thereof.

6. A method of treating tuberculosis or a *Mycobacterium* infection comprising administering to a subject in need thereof a therapeutically effective amount of a compound of claim 2, or a pharmaceutically acceptable salt thereof.

7. A pharmaceutical composition comprising a compound of claim 1, or a pharmaceutically acceptable salt thereof, for treatment of tuberculosis or a *Mycobacterium* infection in an animal.

8. A pharmaceutical composition comprising a compound of claim 2, or a pharmaceutically acceptable salt thereof, for treatment of tuberculosis or a *Mycobacterium* infection in an animal.

9. A compound of claim 1, or a pharmaceutically acceptable salt thereof, for inhibition of DprE1 in an animal.

10. A compound of claim 2, or a pharmaceutically acceptable salt thereof, for inhibition of DprE1 in an animal.

11. A method of inhibiting DprE1 comprising administering to a subject suffering from infection by *Mycobacterium* expressing DprE1 a therapeutically effective amount of a compound of claim 1, or a pharmaceutically acceptable salt thereof.

12. A method of inhibiting DprE1 comprising administering to a subject suffering from infection by *Mycobacterium* expressing DprE1 a therapeutically effective amount of a compound of claim 2, or a pharmaceutically acceptable salt thereof.

13. A pharmaceutical composition comprising a compound of claim 1, or a pharmaceutically acceptable salt thereof, for inhibiting DprE1.

14. A pharmaceutical composition comprising a compound of claim 2, or a pharmaceutically acceptable salt thereof, for inhibiting DprE1.

15. A compound of the formula:

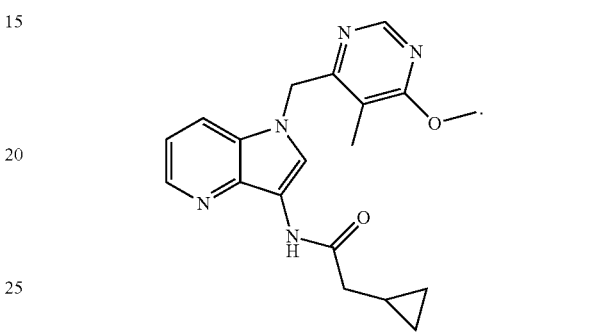

16. A pharmaceutical composition comprising the compound of claim 15, or a pharmaceutically acceptable salt thereof, and a pharmaceutically acceptable carrier or diluent.

17. A method of treating tuberculosis or a *Mycobacterium* infection comprising administering to a subject in need thereof a therapeutically effective amount of a compound of claim 15, or a pharmaceutically acceptable salt thereof.

18. The method of claim 17, wherein the tuberculosis or *Mycobacterium* infection is drug resistant.

19. A method of inhibiting DprE1 comprising administering to a subject suffering from infection by *Mycobacterium* expressing DprE1 a therapeutically effective amount of a compound of claim 15, or a pharmaceutically acceptable salt thereof.

20. The method of claim 19, wherein the infection is drug resistant.

21. The method of claim 5, wherein the tuberculosis or *Mycobacterium* infection is drug resistant.

22. The method of claim 6, wherein the tuberculosis or *Mycobacterium* infection is drug resistant.

23. The method of claim 11, wherein the infection is drug resistant.

24. The method of claim 12, wherein the infection is drug resistant.

25. The pharmaceutical composition of claim 7, wherein the animal is a human.

26. The compound of claim 9, wherein the animal is a human.

* * * * *